United States Patent
Kano et al.

(10) Patent No.: US 6,908,913 B2
(45) Date of Patent: Jun. 21, 2005

(54) CARBAPENEM DERIVATIVES

(75) Inventors: Yuko Kano, Yokohama (JP); Yasuo Yamamoto, Yokohama (JP); Takahisa Maruyama, Yokohama (JP); Takehiko Sawabe, Yokohama (JP); Eiki Shitara, Yokohama (JP); Kazuhiro Aihara, Yokohama (JP); Kunio Atsumi, Yokohama (JP); Takashi Ida, Yokohama (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 0 days.

(21) Appl. No.: 10/344,729

(22) PCT Filed: Nov. 22, 2001

(86) PCT No.: PCT/JP01/10252

§ 371 (c)(1),
(2), (4) Date: Feb. 14, 2003

(87) PCT Pub. No.: WO02/42312

PCT Pub. Date: May 30, 2002

(65) Prior Publication Data

US 2004/0038967 A1 Feb. 26, 2004

(30) Foreign Application Priority Data

Nov. 24, 2000 (JP) ........................ 2000-356997

(51) Int. Cl.[7] ............... A61K 31/429; C07D 519/06
(52) U.S. Cl. .................. 514/210.09; 540/302
(58) Field of Search ............ 514/210.09; 540/302

(56) References Cited

U.S. PATENT DOCUMENTS 6,458,780 B1 * 10/2002 Kano et al. ............ 514/210.09
6,677,331 B2 * 1/2004 Ida et al. ................ 514/210.09

FOREIGN PATENT DOCUMENTS

| AU | 9948024 A1 | 2/2000 |
| EP | 1022279 A1 | 7/2000 |
| WO | 01/55154 A1 | 8/2001 |
| WO | 01/55155 A1 | 8/2001 |

OTHER PUBLICATIONS

Wermuth "The practice of medicinal chemistry" Acad. Press, p. 203–237 (1996).*

* cited by examiner

*Primary Examiner*—Celia Chang
(74) *Attorney, Agent, or Firm*—Wenderoth, Lind & Ponack, L.L.P.

(57) ABSTRACT

An objective of the present invention is to provide carbapenem derivatives which have strong antibiotic activity also against MRSA, PRSP, Influenzavirus, and β-lactamase producing bacteria and are stable to DHP-1. The carbapenem derivatives according to the present invention are compounds represented by formulae (I) and (II) or pharmaceutically acceptable salts thereof:

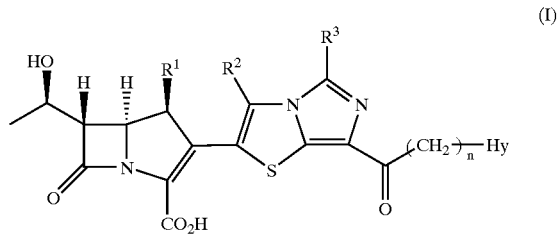

(I)

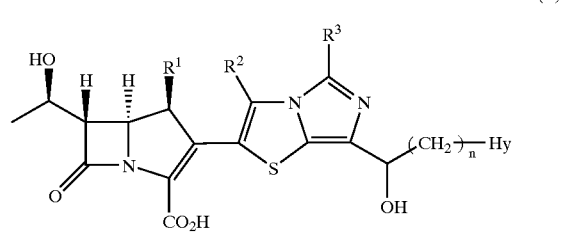

(II)

wherein $R^1$ represents H or methyl, $R^2$ and $R^3$ each independently represent H; halogen; substituted or unsubstituted alkyl; cycloalkyl; substituted or unsubstituted alkylcarbonyl; carbamoyl; substituted or unsubstituted aryl; substituted or unsubstituted alkylthio; morpholinyl; alkylsulfonyl; or formyl, n is 0 (zero) to 4, and Hy represents a substituted or unsubstituted monocyclic or bicyclic heterocyclic group.

9 Claims, No Drawings

US 6,908,913 B2

CARBAPENEM DERIVATIVES

BACKGROUND OF THE INVENTION

1. Field of the Invention

The present invention relates to carbapenem compounds which have excellent antibiotic activity and a broad antibiotic spectrum. More particularly, the present invention relates to novel carbapenem derivatives having a substituted imidazo[5,1-b]thiazole group at the 2-position on the carbapenem ring, or a salt thereof.

2. Related Art

Carbapenem derivatives have potent antibiotic activity and a broad antibiotic spectrum and thus have been energetically studied as a highly useful β-lactam agent, and Imipenem, Panipenem, and Meropenem have already been clinically used.

At the present time, however, both Imipenem and Panipenem, are used as a mixture due to instability against renal dehydropeptidase-1 (hereinafter referred to as "DHP-1") in the case of Imipenem and in order to reduce nephrotoxicity in the case of Panipenem. On the other hand, Meropenem, by virtue of the presence of a methyl group at the 1β-position, has increased stability to DHP-1 and thus can be used alone. The stability of Meropenem to DHP-1, however, is still unsatisfactory. Further, antibiotic activities against methicillin resistant *Staphylococcus aureus* (hereinafter referred to as "MRSA") which has recently caused serious clinical problems, as well as against penicillin resistant *Streptococcus pneumoneae* (hereinafter referred to as "PRSP"), resistant *Pseudomonas aeruginosa*, enterococci, and Influenzavirus, are not always satisfactory. Drugs effective for these bacteria which induce infectious diseases have been dedired in the art.

For example, carbapenem derivatives in which a carbon atom on an imidazo[5,1-b]thiazole group is attached to the 2-position of the carbapenem ring are disclosed in WO 98/32760 and WO 00/06581.

SUMMARY OF THE INVENTION

The present inventors have now found that a certain group of carbapenem derivatives having an imidazo[5,1-b]thiazole group have high antibiotic activities against a wide spectrum of Gram-positive bacteria and Gram-negative bacteria and, at the same time, have high antibiotic activities against MRSA, PRSP, Influenzavirus, and β-lactamase producing bacteria and are also highly stable to DHP-1. The present invention is based on such finding.

Accordingly, an object of the present invention is to provide carbapenem derivatives which have high antibiotic activities also against MRSA, PRSP, Influenzavirus, and β-lactamase producing bacteria and are stable to DHP-1.

According to the present invention, there is provided a compound represented by formula (I) or a pharmaceutically acceptable salt thereof:

(I)

wherein
R$^1$ represents a hydrogen atom or methyl,
R$^2$ and R$^3$, which may be the same or different, each represent
a hydrogen atom;
a halogen atom;
lower alkyl optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino;
lower cycloalkyl;
lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino;
carbamoyl;
aryl optionally substituted by amino optionally substituted by one or two lower alkyl groups;
lower alkylthio wherein the alkyl portion of lower alkylthio is optionally substituted by amino, hydroxyl, azide, a halogen atom, cyano, carbamoyl, formylamino, lower alkylcarbonylamino, aminosulfonylamino, or lower alkylthio;
morpholinyl;
lower alkylsulfonyl; or
formyl;
n is an integer of 0 to 4, and
Hy represents a four- to seven-membered monocyclic or nine- or ten-membered bicyclic saturated or unsaturated heterocyclic group having one to four hetero-atoms selected from the group consisting of nitrogen, oxygen, and sulfur atoms,
the saturated or unsaturated heterocyclic group represented by Hy is optionally substituted by
a halogen atom;
cyano;
lower alkyl wherein one or more hydrogen atoms on the lower alkyl group are optionally substituted by groups selected from the group consisting of a halogen atom; hydroxyl; carbamoyl; carboxylmethyl-substituted carbamoyl; amino; N,N-di-lower alkylamino; aryl optionally substituted by amino; a monocyclic or bicyclic heterocyclic group containing one or more hetero-atoms selected from the group consisting of nitrogen, oxygen, and sulfur atoms, optionally substituted by aminosulfonyl or carboxyl, preferably a four- to seven-membered monocyclic or nine- or ten-membered bicyclic saturated or unsaturated heterocyclic group containing one to four hetero-atoms selected from the group consisting of nitrogen, oxygen, and sulfur atoms, more preferably pyridinyl, morpholinyl, pyrrolidinyl, or piperidinyl; carboxyl; imino; lower alkoxycarbonyl; lower alkylcarbonyl; aminosulfonylamino; amino lower alkylthio; lower alkylsulfonyl; (N,N-di-lower alkylamino)

sulfonylamino; N'-(N,N-di-lower alkylamino)sulfonyl-N'-lower alkylamino; halogenated lower alkylcarbonyl; N-aminosulfonylpiperidinyl; and cyano;

lower alkylthio wherein one or more hydrogen atoms on the alkyl group are optionally substituted by a group selected from the group consisting of a halogen atom, hydroxyl, carbamoyl, amino, and aryl;

lower alkylsulfonyl wherein one or more hydrogen atoms on the alkyl group are optionally substituted by a group selected from the group consisting of a halogen atom, hydroxyl, carbamoyl, amino, 1-iminoethylamino, and aryl;

hydroxyl;
lower alkoxy;
hydroxyaminophenyl-substituted lower alkoxy;
halogenated lower alkoxy;
aminophenyl-substituted lower alkoxy;
formyl;
lower alkylcarbonyl;
arylcarbonyl;
carboxyl;
lower alkoxycarbonyl;
carbamoyl;
N-lower alkylcarbamoyl;
N,N-di-lower alkylaminocarbonyl;
amino;
N-lower alkylamino;
N,N-di-lower alkylamino;
formylamino;
lower alkylcarbonylamino;
aminosulfonylamino;
(N-lower alkylamino)sulfonylamino;
(N,N-di-lower alkylamino)sulfonylamino;
aryl; or a monocyclic or bicyclic heterocyclic group containing one or more hetero-atoms selected from the group consisting of nitrogen, oxygen, and sulfur atoms, optionally substituted by aminosulfonyl or carboxyl, preferably an optionally substituted four- to seven-membered monocyclic or nine- or ten-membered bicyclic saturated or unsaturated heterocyclic group containing one to four hetero-atoms selected from the group consisting of nitrogen, oxygen, and sulfur atoms.

Further, according to the present invention, there is provided a compound represented by formula (II) or a pharmaceutically acceptable salt thereof:

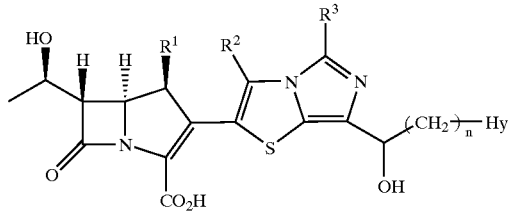

(II)

wherein $R^1$, $R^2$, $R^3$, n, and Hy are as defined in formula (I).

The compounds according to the present invention have high antibiotic activities against a wide spectrum of Gram-positive bacteria and Gram-negative bacteria. In particular, the compounds according to the present invention have high antibiotic activities also against MRSA, PRSP, Influenzavirus, and β-lactamase producing bacteria. Accordingly, the compounds according to the present invention are useful as antibiotic preparations.

Further, according to the present invention, there is provided a pharmaceutical composition comprising a compound according to the present invention as active ingredient. This pharmaceutical composition is useful for the therapy and/or prophylaxis of infectious diseases.

Furthermore, according to the present invention, there is provided use of a compound according to the present invention, for the manufacture of the pharmaceutical composition according to the present invention.

Furthermore, according to the present invention, there is provided a method for the therapy and/or prophylaxis of infectious diseases, comprising the step of administering a therapeutically and/or prophylactically effective amount of a compound according to the present invention to mammals including humans.

DETAILED DESCRIPTION OF THE INVENTION

The term "lower alkyl" and the term "lower alkoxy" as used herein as a group or a part of a group respectively mean straight chain or branched chain alkyl and alkoxy having 1 to 6, preferably 1 to 4 carbon atoms.

Examples of lower alkyl include methyl, ethyl, n-propyl, isopropyl, n-butyl, i-butyl, s-butyl, t-butyl, n-pentyl, and n-hexyl.

Examples of lower alkoxy include methoxy, ethoxy, n-propoxy, i-propoxy, n-butoxy, s-butoxy, and t-butoxy.

The term "lower cycloalkyl" means monocyclic alkyl having 3 to 6 carbon atoms, preferably cyclopropyl.

The term "halogen atom" means a fluorine, chlorine, bromine, or iodine atom.

The term "aryl" as a group or a part of a group means a five- to seven-membered aromatic monocyclic carbocyclic ring and a nine- to twelve-membered aromatic bicyclic carbocyclic ring, preferably phenyl or naphthyl, more preferably phenyl.

The term "monocyclic or bicyclic heterocyclic group containing one or more hetero-atoms selected from the group consisting of nitrogen, oxygen, and sulfur atoms" preferably means a four- to seven-membered monocyclic or nine- or ten-membered bicyclic saturated or unsaturated heterocyclic group containing one to four hetero-atoms selected from the group consisting of nitrogen, oxygen, and sulfur atoms. When a plurality of hetero-atoms are contained in the heterocyclic group, the hetero-atoms may be the same or different.

Preferred heterocyclic groups represented by Hy include a heterocyclic group containing one or two nitrogen atoms with the remaining ring atoms being carbon atoms, a heterocyclic group containing one nitrogen atom and one sulfur atom with the remaining ring atoms being carbon atoms, and a heterocyclic group containing one sulfur atom with the remaining ring atoms being carbon atoms. More preferred are pyridinyl, pyridinium-yl, tetrahydropyridinyl, thiazolyl, pyrimidinyl, thienyl, quinolinyl, quinolinium-yl, isoquinolinyl, dihydroisoquinolinyl, piperazinyl, piperidinyl, indolyl, thiomorpholinyl, imidazolyl, and pyrrolidinyl. Most preferred are pyridinyl, pyridinium-yl, tetrahydropyridinyl, thiazolyl, pyrimidinyl, thienyl, quinolinyl, quinolinium-yl, and pyrrolidinyl.

The substituent on the lower alkyl and lower alkylcarbonyl groups optionally represented by $R^2$ and $R^3$ is preferably hydroxyl, lower alkoxy, N,N-di-lower alkylamino, or N-carbamoyl lower alkyl-N,N-di-lower alkylammonino.

The substituent on the aryl group optionally represented by $R^2$ and $R^3$ is preferably N,N-dialkylamino.

The substituent on the lower alkylthio group optionally represented by $R^2$ and $R^3$ is preferably amino, hydroxyl, or azide.

The substituent on the heterocyclic group represented by Hy is preferably lower alkyl optionally substituted by carboxylmethyl-substituted carbamoyl, carbamoyl, phenyl, aminophenyl, N,N-di-lower alkylamino, amino, hydroxyl, morpholinyl, pyrrolidinyl, carboxyl, imino, amino lower alkylthio, lower alkoxycarbonyl, lower alkylcarbonyl, aminosulfonylamino, piperidinyl, lower alkylsulfonyl, (N,N-di-lower alkylamino)sulfonylamino, N'-(N,N-di-lower alkylamino)sulfonyl-N'-lower alkylamino, halogenated lower alkylcarbonyl, N-aminosulfonylpiperidinyl, or cyano; carbamoyl; pyridinyl; Naminosulfonylpyrrolidinyl; 2-carboxypyrrolidinyl; phenyl; hydroxyl; lower alkoxy; hydroxyaminophenylsubstituted lower alkoxy; lower alkoxy substituted by a halogen atom; aminophenyl-substituted lower alkoxy; amino; carboxyl; lower alkylthio optionally substituted by amino; amino lower alkylthio; amino lower alkylsulfonyl; or 1-iminoethylamino lower alkylsulfonyl. More preferred are lower alkyl substituted by a group selected from the group consisting of carbamoyl, carboxyl, and aminosulfonylamino; and lower alkylthio substituted by amino.

The heterocyclic group represented by Hy may be bonded to carbonyl, —CH(—OH)—, or $C_{1-4}$ alkylene at any position on the heterocyclic ring. When Hy represents pyridinyl, bonding at the 3-position is preferred. When Hy represents pyrrolidinyl, bonding at the 2-position is preferred.

When the heterocyclic group represented by Hy has a nitrogen atom on its ring, the nitrogen atom may have a substituent to form a quaternary ammonium atom. Preferred substituents usable herein include carbamoylmethyl, carboxylmethyl, and aminosulfonylaminoethyl.

$R^1$ preferably represents methyl.

$R^2$ and $R^3$ are preferably a hydrogen atom, a halogen atom, optionally substituted lower alkyl, lower cycloalkyl, lower alkylcarbonyl, carbamoyl, aryl, optionally substituted lower alkylthio, morpholinyl, formyl, or lower alkylsulfonyl, more preferably a hydrogen atom.

n is preferably an integer of 0 (zero) to 2, more preferably 0.

Hy preferably represents optionally substituted
(pyridin-3-yl),
(pyridinium-3-yl),
[1,4,5,6-tetrahydropyridin-3-yl],
(pyridin-4-yl),
(pyridinium-4-yl),
(thiazol-5-yl),
(pyrrolidin-2-yl),
(pyrimidin-5-yl),
(thiophen-2-yl),
(quinolin-3-yl),
(quinolinium-3-yl),
(isoquinolin-4-yl),
(1,2-dihydroisoquinolin-4-yl),
(piperidin-2-yl),
(piperazin-1-yl),
(piperazinium-4-yl),
(piperidin-4-yl),
(indol-3-yl),
(pyrrolidin-1-yl),
(piperazinium-1-yl),
(pyrrolidinium-1-yl),
(piperidin-3-yl),
[1,2-dihydropyridin-3-yl],
(imidazol-1-yl), or
(thiomorpholin-4-yl).

More preferably, Hy represents optionally substituted (pyridin-3-yl), optionally substituted (pyridinium-3-yl), or optionally substituted ((2S)pyrrolidin-2-yl).

A group of preferred compounds represented by formulae (I) and (II) are those wherein $R^1$ represents a hydrogen atom or methyl, $R^2$ and $R^3{}_1$ which may be the same or different, each represent
a hydrogen atom;
a halogen atom;
lower alkyl optionally substituted by a halogen atom, cyano, hydroxyl, carbamoyl, amino, formylamino, lower alkylcarbonylamino, aminosulfonylamino, or lower alkylthio;
lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, or lower alkylthio;
carbamoyl;
aryl; or
lower alkylthio wherein the alkyl portion of lower alkylthio is optionally substituted by a halogen atom, cyano, hydroxyl, carbamoyl, amino, formylamino, lower alkylcarbonylamino, aminosulfonylamino, or lower alkylthio, n is an integer of 0 (zero) to 4, and Hy represents a four- to seven-membered monocyclic or nine- or ten-membered bicyclic saturated or unsaturated heterocyclic group containing one to four hetero-atoms selected from the group consisting of nitrogen, oxygen, and sulfur atoms, the saturated or unsaturated heterocyclic group represented by Hy is optionally substituted by
a halogen atom;
cyano;
lower alkyl wherein one or more hydrogen atoms on the lower alkyl group are optionally substituted by a group selected from the group consisting of a halogen atom, hydroxyl, carbamoyl, amino, aryl, and a monocyclic or bicyclic heterocyclic group containing one or more hetero-atoms selected from the group consisting of nitrogen, oxygen, and sulfur atoms, preferably a four- to seven-membered monocyclic or nine- or ten-membered bicyclic saturated or unsaturated heterocyclic group containing one to four hetero-atoms selected from the group consisting of nitrogen, oxygen, and sulfur atoms, more preferably pyridinyl, morpholinyl, pyrrolidinyl, or piperidinyl;
lower alkylthio wherein one or more hydrogen atoms on the alkyl group are optionally substituted by a group selected from the group consisting of a halogen atom, hydroxyl, carbamoyl, amino, and aryl;
lower alkylsulfonyl wherein one or more hydrogen atoms on the alkyl group are optionally substituted by a group selected from the group consisting of a halogen atom, hydroxyl, carbamoyl, amino, and aryl;
hydroxyl;
lower alkoxy;
formyl;
lower alkylcarbonyl;
arylcarbonyl;
carboxyl;
lower alkoxycarbonyl;
carbamoyl;
N-lower alkylcarbamoyl;
N,N-di-lower alkylaminocarbonyl;
amino;
N-lower alkylamino;
N,N-di-lower alkylamino;
formylamino;

lower alkylcarbonylamino;
aminosulfonylamino;
(N-lower alkylamino)sulfonylamino;
(N,N-di-lower alkylamino)sulfonylamino;
aryl; or
a monocyclic or bicyclic heterocyclic group containing one or more hetero-atoms selected from the group consisting of nitrogen, oxygen, and sulfur atoms, preferably an optionally substituted four- to seven-membered monocyclic or nine- or ten-membered bicyclic saturated or unsaturated heterocyclic group containing one to four hetero-atoms selected from the group consisting of nitrogen, oxygen, and sulfur atoms.

Another group of preferred compounds represented by formulae (I) and (II) are those wherein
$R^1$ represents a hydrogen atom or methyl,
$R^2$ and $R^3$, which may be the same or different, each represent
a hydrogen atom,
a halogen atom,
optionally substituted lower alkyl,
lower cycloalkyl,
lower alkylcarbonyl,
carbamoyl,
optionally substituted aryl,
optionally substituted lower alkylthio,
morpholinyl,
lower alkylsulfonyl, or
formyl,
n is an integer of 0 (zero) to 2, and
Hy represents a group selected from the group consisting of optionally substituted pyridinyl, optionally substituted pyridinium-yl, optionally substituted tetrahydropyridinyl, optionally substituted thiazolyl, optionally substituted pyrimidinyl, optionally substituted thienyl, optionally substituted quinolinyl, optionally substituted quinolinium-yl, optionally substituted isoquinolinyl, optionally substituted dihydroisoquinolinyl, optionally substituted piperazinyl, optionally substituted piperidinyl, optionally substituted indolyl, optionally substituted thiomorpholinyl, optionally substituted imidazolyl, and optionally substituted pyrrolidinyl.

A further group of preferred compounds represented by formulae (I) and (II) are those wherein
$R^1$ represents a hydrogen atom or methyl,
$R^2$ and $R^3$, which may be the same or different, each represent
a hydrogen atom,
a halogen atom,
optionally substituted lower alkyl,
optionally substituted lower alkylcarbonyl,
carbamoyl,
aryl, or
optionally substituted lower alkylthio,
n is an integer of 0 (zero) to 4, and
Hy represents a group selected from the group consisting of optionally substituted pyridinyl, optionally substituted pyridinium-yl, optionally substituted tetrahydropyridinyl, optionally substituted thiazolyl, optionally substituted pyrimidinyl, optionally substituted thienyl, optionally substituted quinolinyl, optionally substituted quinolinium-yl, and optionally substituted pyrrolidinyl.

A group of preferred compounds represented by formula (II) are those wherein
$R^1$ represents methyl,
$R^2$ and $R^3$ each represent a hydrogen atom,
n is 0 (zero), and
Hy represents an optionally substituted six-membered saturated heterocyclic group containing one to four heteroatoms.

A group of more preferred compounds represented by formulae (I) and (II) are those wherein
$R^1$ represents a hydrogen atom or methyl,
$R^2$ and $R^3$ represent a hydrogen atom,
n is 0 (zero), and
Hy represents pyridinium-yl having carbamoylmethyl at its 1-position.

Another group of preferred compounds represented by formulae (I) and (II) are those wherein n is 0 (zero).

A further group of preferred compounds represented by formulae (I) and (II) are those wherein $R^1$ represents methyl and $R^2$ and $R^3$ represent a hydrogen atom.

Another group of more preferred compounds represented by formulae (I) and (II) are those wherein
$R^1$ represents methyl,
$R^2$ and $R^3$ represent a hydrogen atom,
n is 0 (zero), and
Hy represents pyridinium-yl which optionally has carbamoyl lower alkyl, carboxyl lower alkyl, or aminosulfonylamino lower alkyl at its 1-position and amino lower alkylthio at its position other than the 1-position.

A further group of more preferred compounds represented by formula (I) are those wherein $R^1$ represents methyl, $R^2$ and $R^3$ represent a hydrogen atom, n is 0 (zero), and Hy represents pyridin-3-yl.

Particularly preferred compounds represented by formulae (I) and (II) include
compounds wherein $R^1$ represents methyl, $R^2$ and $R^3$ represent a hydrogen atom, n is 0 (zero), and Hy represents 1-carbamoylmethylpyridinium-3-yl,
compounds wherein $R^1$, $R^2$, and $R^3$ represent a hydrogen atom, n is 0 (zero), and Hy represents 1-carbamoylmethylpyridinium-3-yl,
compounds wherein $R^1$ represents methyl, $R^2$ and $R^3$ represent a hydrogen atom, n is 0 (zero), and Hy represents 1-carbamoylmethyl-5-phenylpyridinium-3-yl,
compounds wherein $R^1$ represents methyl, $R^2$ and $R^3$ represent a hydrogen atom, n is 0 (zero), and Hy represents (2S)-pyrrolidin-2-yl,
compounds wherein $R^1$ represents methyl, $R^2$ and $R^3$ represent a hydrogen atom, n is 0 (zero), and Hy represents 1-carboxymethylpyridinium-3-yl, and
compounds wherein $R^1$ represents methyl, $R^2$ and $R^3$ represent a hydrogen atom, n is 0 (zero), and Hy represents 1-(2-aminosulfonylaminoethyl)pyridinium-3-yl.

The compounds according to the present invention may form pharmaceutically acceptable salts. Examples of such salts include: inorganic salts such as lithium salts, sodium salts, potassium salts, calcium salts, or magnesium salts; ammonium salts; organic base salts such as triethylamine salts or diisopropylethylamine salts; mineral acid salts such as hydrochloric acid salts, sulfuric acid salts, phosphoric acid salts, or nitric acid salts; and organic acid salts such as acetic acid salts, carbonic acid salts, citric acid salts, malic acid salts, oxalic acid salts, or methanesulfonic acid salts. Preferred are intramolecular salts, sodium salts, potassium salts, or hydrochloric acid salts.

Specific examples of carbapenem derivatives represented by formulae (I) and (II) according to the present invention include compounds 1 to 175 described in working examples below.

Compounds represented by formula (I) according to the present invention are preferably produced according to scheme 1.

Scheme 1

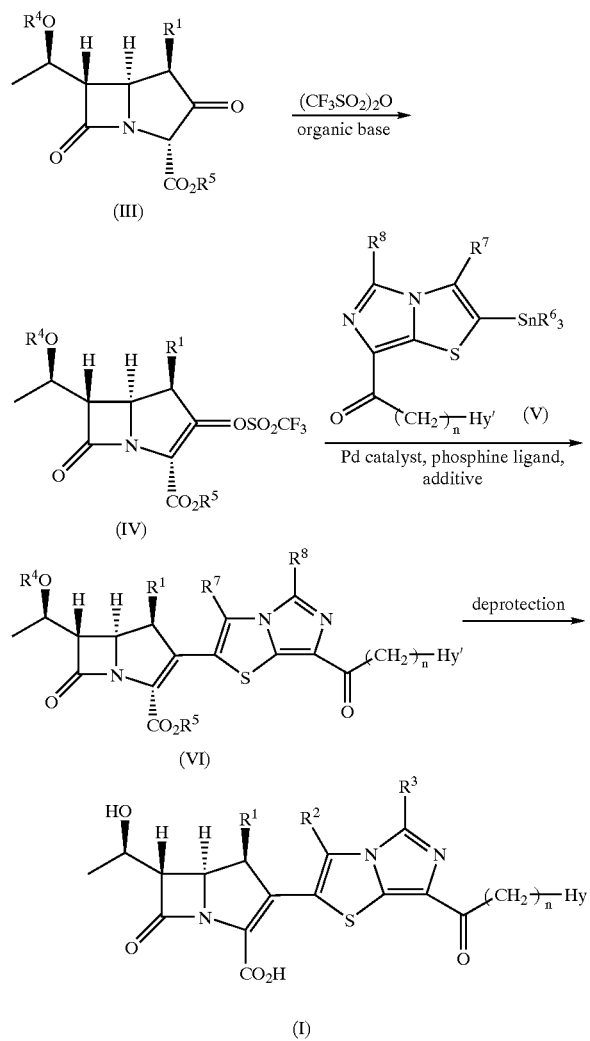

In the above scheme, $R^1$, $R^2$, $R^3$, n, and Hy are as defined in formula (I); $R^4$ represents a hydrogen atom or a protective group of hydroxyl, for example, t-butyldimethylsilyl, trimethylsilyl, triethylsilyl, 4-nitrobenzyloxycarbonyl, 4-methoxybenzyloxycarbonyl, or allyloxycarbonyl; $R^5$ represents a protective group of carboxyl, for example, 4-nitrobenzyl, 4-methoxybenzyl, diphenylmethyl, t-butyldimethylsilyl, or allyl; $R^6$ represents lower alkyl, preferably n-butyl or methyl; $R^7$ and $R^8$ have the same meaning as $R^2$ and $R^3$ or represent a group formed by protecting a functional group contained in $R^2$ and $R^3$, for example, hydroxyl, amino, or carboxyl, by a conventional protective group; and Hy' has the same meaning as Hy or represents a group formed by protecting a functional group contained in Hy, for example, hydroxyl, amino, or carboxyl by a conventional protective group. The conventional protective group is described in Protective Groups in Organic Synthesis (Theodora W. Greene, Peter G. M. Wuts, published by John Wiley & Sons, Inc.).

The compound of formula (III) in the first step shown in the scheme can be synthesized by a conventional method, and the tin compound of formula (V) in the second step shown in the scheme can be synthesized according to the method described in WO 98/32760.

In the first step, the compound of formula (III) can be converted to the compound of formula (IV) by the following method. Specifically, the compound of formula (IV) can be prepared by reacting the compound of formula (III) with one (1) equivalent or an excessive amount of trifluoromethanesulfonic anhydride in the presence of an organic base, preferably diisopropylethylamine, in an amount of one (1) equivalent or an excessive amount relative to trifluoromethanesulfonic anhydride in an inert solvent, such as acetonitrile, tetrahydrofuran, dichloromethane, or toluene, or a mixed solvent composed of two or more of these inert solvents at −50° C. to +50° C. for 10 min to 24 hr and then subjecting the reaction mixture to the conventional separation and purification procedure.

In the second step, the compound of formula (IV) can be converted to the compound of formula (VI) by the following method. Specifically, the compound of formula (VI) can be prepared by reacting the compound of formula (IV) with one (1) equivalent or an excessive amount of the compound of formula (V) in the presence of 0.001 to one (1) equivalent of a palladium catalyst, for example, tetrakis(triphenylphosphine)palladium(0), tris(dibenzylideneacetone)dipalladium(0), or a tris(dibenzylideneacetone)dipalladium(0)-chloroform adduct, 0.01 to one (1) equivalent of a phosphine ligand, for example, triphenylphosphine, tri-2-furylphosphine, tri-2-thienylphosphine, or tris(2,4,6-trimethoxyphenyl) phosphine, and 1 to 10 equivalents of an additive, for example, zinc chloride, lithium chloride, or cesium fluoride either alone or in combination, in an inert solvent, for example, tetrahydrofuran, dimethoxyethane, dioxane, acetonitrile, acetone, ethanol, dimethyl sulfoxide, sulfolane, N,N-dimethylformamide, N,N-dimethylacetamide, N-methylpyrrolidinone, or hexamethylphosphoric triamide, or a mixed solvent composed of two or more of these inert solvents at 0° C. to 100° C. for 10 min to 7 days and then subjecting the reaction mixture to the conventional post-treatment.

Finally, in the third step, the compound of formula (I) according to the present invention can be prepared by deprotecting the compound of formula (VI) by a deprotection reaction in one step or plural steps depending on the kinds of the protective groups.

In this case, the deprotection reactions, which vary depending upon the kinds of the protective groups used, can be carried out according to the conventional methods commonly known in the art. When any or all of the protective groups can be removed under acidic conditions, for example, a mineral acid such as hydrochloric acid, an organic acid such as formic acid, acetic acid or citric acid, or a Lewis acid such as aluminum chloride is used. When the protective groups are removed under reducing conditions, catalytic reduction with a variety of catalysts, or a metallic reducing agent such as zinc or iron may be used. When $R^4$ represents a silyl type protective group, for example, a t-butyldimethylsilyl group, a trimethylsilyl group or a triethylsilyl group, the protective group can be easily removed with the use of a fluorine ion reagent, for example, tetrabutylammonium fluoride. When $R^4$ represents allyloxycarbonyl and $R^5$ represents allyl, the protective groups can be easily removed with the use of a variety of palladium complexes, for example, tetrakis(triphenylphosphine)palladium(0).

The compound of formula (I) thus obtained can be isolated and purified, for example, by crystallization or by chromatography with a nonionic macro-high porous resin, gel filtration with Sephadex or the like, or reverse phase silica gel column chromatography.

Compounds of formula (I), wherein Hy has a quaternary ammonium atom, can be prepared according to scheme 2.

Scheme 2

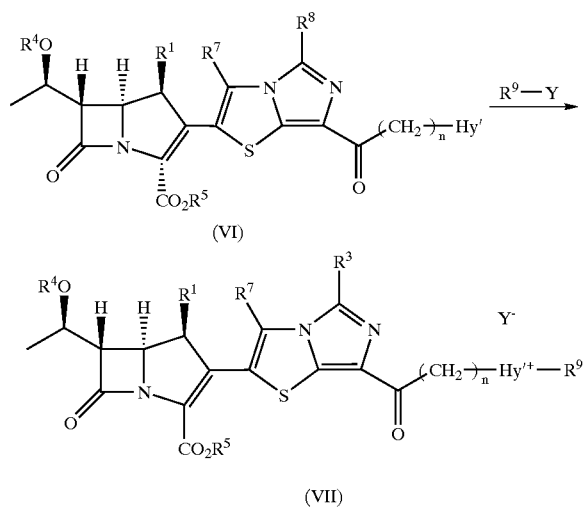

In the above scheme, $R^1$ and n are as defined in formula (I); $R^4$, $R^5$, $R^7$, $R^8$, and Hy' are as defined in scheme 1; $R^9$ represents optionally substituted lower alkyl; and Y represents a suitable leaving group, for example, Cl, Br, I, —OSO₂CF₃, —OSO₂CH₃, or —OSO₂PhCH₃.

Specifically, the compound of formula (VII) can be prepared by adding one (1) equivalent or an excessive amount of $R^9$—Y, for example, methyl iodide, carbamoylmethyl iodide, methyl trifluoromethanesulfonate, benzyl bromide, or 3-azidopropyl trifluoromethanesulfonate, to the compound of formula (VI) in the absence or presence of an inert solvent, for example, acetonitrile, acetone, tetrahydrofuran, dichloromethane, toluene, N,N-dimethylformamide, N,N-dimethylacetamide, or dimethylsulfoxide, either alone or as a mixture of two or more of the inert solvents, and allowing a reaction to proceed at −80° C. to +60° C. for 15 min to one week, and then subjecting the reaction mixture to the conventional post-treatment.

The compound of formula (VII) can be led to the compound of formula (I) in the same manner as in the compound of formula (VI).

Compounds of formula (II) according to the present invention can be produced according to scheme 3.

Scheme 3

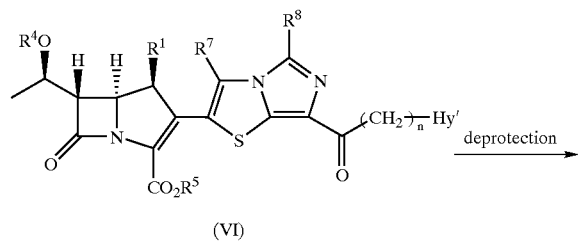

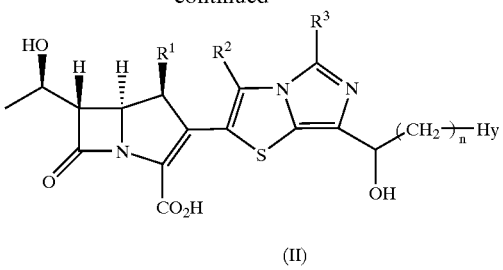

In the above scheme, $R^1$, $R^2$, $R^3$, n, and Hy are as defined in formula (I); and $R^4$, $R^5$, $R^7$, $R^8$, and Hy' are as defined in scheme 1.

Specifically, the compound of formula (II) according to the present invention can be prepared depending upon the kind of Hy by deprotecting the compound of formula (VI) by a deprotection reaction in one step or plural steps depending on the kinds of the protective groups in the same manner as described above.

The compound of formula (II) thus obtained can be isolated and purified, for example, by crystallization or by chromatography with a nonionic macro-high porous resin, gel filtration with Sephadex or the like, or reverse phase silica gel column chromatography.

The compounds according to the present invention have high antibiotic activities against a wide spectrum of Gram-positive bacteria and Gram-negative bacteria and, at the same time, have high antibiotic activities against MRSA, PRSP, Influenzavirus, and β-lactamase producing bacteria. Further, they have low toxicity and are also stable to DHP-1. Therefore, the compounds according to the present invention can be used for the treatment of infectious diseases caused by various pathogenic bacteria in animals including humans. The pharmaceutical composition comprising the compound according to the present invention or a pharmacologically acceptable salt thereof as active ingredient can be administered orally or parenterally by administration routes, for example, intravenous injection, intramuscular injection, or subcutaneous, rectal or percutaneous administration to human and non-human animals.

The pharmaceutical composition comprising the compound according to the present invention as active ingredient may be formed into appropriate dosage forms depending on administration routes. Specifically, the compounds according to the present invention may be mainly formulated into, for example, injections such as intravenous injections and intramuscular injections; oral preparations such as capsules, tablets, granules, powders, pills, fine subtilaes, and troches; preparations for rectal administrations; and oleaginous suppositories.

These preparations may be prepared by conventional methods with commonly used adjuvants for preparations, for example, excipients, extenders, binders, humidifiers, disintegrants, surface active agents, lubricants, dispersants, buffers, preservatives, dissolution aids, antiseptics, flavoring agents, analgesic agents, and stabilizers.

Non-toxic adjuvants usable herein include, for example, lactose, fructose, glucose, starch, gelatin, magnesium carbonate, synthetic magnesium silicate, talc, magnesium stearate, methylcellulose or a salt thereof, gum arabic, polyethylene glycol, syrup, petrolatum, glycerin, ethanol, propylene glycol, citric acid, sodium chloride, sodium sulfite, and sodium phosphate.

The dose may be appropriately determined depending on various conditions, for example, the purpose of treatment or prevention and the age, sex, and severity of condition of patients. The dose for the treatment of infectious diseases is generally about 25 to 2,000 mg, preferably 50 to 1,000 mg per day per adult. This dose may be administered at a time daily or divided doses of several times daily.

EXAMPLES

The present invention is further illustrated by the following Synthesis Examples, Examples, and Test Examples that are not intended as a limitation of the invention.

Synthesis Example 1

7-(Pyridin-3-yl)carbonyl-2-(tri-n-butylstannyl)imidazo[5,1-b]thiazole a) 7-[(Pyridin-3-yl)hydroxymethyl]imidazo[5,1-b]thiazole A solution of 2.50 g of 7-iodoimidazo[5,1-b]thiazole in 50 ml of dry THF was cooled in ice, and 11.3 ml of a 0.93 M methylmagnesium bromide/THF solution was added to the cooled solution under an argon atmosphere. The mixture was stirred at that temperature for 20 min. Pyridine-3-aldehyde (1.04 ml) was then added thereto, and the mixture was stirred at that temperature for 40 min and then at room temperature for 4 hr. Water was added to the reaction solution, and the mixture was extracted five times with dichloromethane. The organic layer was dried over anhydrous magnesium sulfate and was then concentrated under the reduced pressure. The residue was purified by column chromatography on silica gel (dichloromethane:methanol= 20:1) to give 1.925 g of 7-[(pyridin-3-yl)hydroxymethyl] imidazo[5,1-b]thiazole.

NMR (CDCl$_3$) δ: 6.05 (1H, s), 6.72 (1H, d, J=4.2 Hz), 7.3–7.4 (2H, m), 7.8–7.9 (1H, m), 7.99 (1H, s), 8.55–8.65 (1H, m), 8.7–8.75 (1H, m)

b) 7-(Pyridin-3-yl)carbonylimidazo[5,1-b]thiazole

Manganese dioxide (1.0 g) was added to a solution of 1.02 g of 7-[(pyridin-3-yl)hydroxymethyl]imidazo[5,1-b]thiazole in 40 ml of dichloromethane, and the mixture was stirred at room temperature for 5 hr. The reaction solution was filtered through Celite, followed by washing with dichloromethane. The filtrate was concentrated under the reduced pressure to give 1.10 g of 7-(pyridin-3-yl)carbonylimidazo[5,1-b]thiazole.

NMR (CDCl$_3$) δ: 7.20 (1H, d, J=4.2 Hz), 7.4–7.5 (1H, m), 7.63 (1H, d, J=4.2 Hz), 8.10 (1H, s), 8.75–8.85 (2H, m), 9.7–9.75 (1H, m)

c) 7-(Pyridin-3-yl)carbonyl-2-(tri-n-butylstannyl)imidazo[5,1-b]thiazole

Tri-n-butylstannyl chloride (0.841 ml) and 2.95 ml of a 1.0 N lithium bis(trimethylsilyl)amide/THF solution were added to a solution of 520 mg of 7-(pyridin-3-yl)carbonylimidazo[5,1-b]thiazole in 25 ml of THF at −60° C. under an argon atmosphere, and the mixture was stirred for 20 min. The temperature of the mixture was raised to −50° C., 1.0 ml of a 1.0 N lithium bis(trimethylsilyl)amide/THF solution was added thereto, and the mixture was stirred for 30 min. The temperature of the mixture was raised to −40° C., 0.5 ml of a 1.0 N lithium bis(trimethylsilyl)amide/THF solution was added thereto, and the mixture was stirred for 30 min. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=2:1→ethyl acetate only) to give 712 mg of the title compound.

NMR (CDCl$_3$) δ: 0.92 (9H, t, J=7.2 Hz), 1.2–1.3 (6H, m), 1.3–1.45 (6H, m), 1.55–1.65 (6H, m), 7.36 (1H, s), 7.4–7.45 (1H, m), 8.03 (1H, s), 8.75–8.85 (2H, m), 9.65–9.7 (1H, m)

Synthesis Example 2

7-(Pyridin-4-yl)carbonyl-2-(tri-n-butylstannyl)imidazo[5,1-b]thiazole a) 7-[(Pyridin-4-yl)hydroxymethyl]imidazo[5,1-b]thiazole 7-[(Pyridin-4-yl)hydroxymethyl]imidazo[5,1-b]-thiazole (1.32 g) was prepared in the same manner as in step a) of Synthesis Example 1, except that 2.50 g of 7-iodoimidazo [5,1-b]thiazole and 1.05 ml of pyridine-4-aldehyde were used as the starting compounds.

NMR (DMSO-d$_6$) δ: 5.76 (1H, d, J=4.8 Hz), 6.19 (1H, d, J=4.8 Hz), 7.11 (1H, d, J=4.5 Hz), 7.35–7.45 (2H, m), 7.80 (1H, d, J=4.5 Hz), 8.11 (1H, s), 8.5–8.55 (2H, m)

b) 7-(Pyridin-4-yl)carbonylimidazo[5,1-b]thiazole 7-(Pyridin-4-yl)carbonylimidazo[5,1-b]thiazole (1.16 g) was prepared in the same manner as in step b) of Synthesis Example 1, except that 1.32 g of 7-[(pyridin-4-yl)hydroxymethyl]imidazo[5,1-b]thiazole was used as the starting compound.

NMR (CDCl$_3$) δ: 7.21 (1H, d, J=4.2 Hz), 7.64 (1H, d, J=4.2 Hz), 8.10 (1H, s), 8.3–8.35 (2H, m), 8.8–8.85 (2H, m)

c) 7-(Pyridin-4-yl)carbonyl-2-(tri-n-butylstannyl)-imidazo[5,1-b]thiazole

The title compound (1.78 g) was prepared in the same manner as in step c) of Synthesis Example 1, except that 1.03 g of 7-(pyridin-4-yl)carbonylimidazo[5,1-b]thiazole was used as the starting compound.

NMR (CDCl$_3$) δ: 0.92 (9H, t, J=7.5 Hz), 1.2–1.3 (6H, m), 1.3–1.45 (6H, m), 1.55–1.65 (6H, m), 7.37 (1H, S), 8.03 (1H, s), 8.25–8.3 (2H, m), 8.8–8.85 (2H, m)

Synthesis Example 3

7-(4-Methylthiazol-5-yl)carbonyl-2-(tri-n-butylstannyl)imidazo[5,1-b]thiazole a) 7-(4-Methylthiazol-5-yl)carbonylimidazo[5,1-b]-thiazole A solution of 1.75 g of 7-iodoimidazo[5,1b]-thiazole in 35 ml of dry THF was cooled in ice, and 8.56 ml of a 0.9 M methylmagnesium bromide/THF solution was added to the cooled solution under an argon atmosphere. The mixture was stirred at that temperature for 20 min, and 923 mg of 4-methylthiazole-5-aldehyde was then added thereto. The mixture was stirred at the same temperature for 20 min and then at room temperature for one hr. Water was added to the reaction solution, and the mixture was extracted five times with dichloromethane. The organic layer was dried over anhydrous magnesium sulfate and was then concentrated under the reduced pressure. The residue was dissolved in 35 ml of dichloromethane to prepare a solution. Manganese dioxide (2.1 g) was added to the solution, and the mixture was stirred at room temperature for 4 hr. The reaction solution was filtered through Celite, followed by washing with dichloromethane. The filtrate was concentrated under the reduced pressure. The residue was recrystallized from dichloromethane-hexane to give 1.50 g of 7-(4-methylthiazol-5-yl)carbonylimidazo[5,1-b]thiazole.

NMR (CDCl$_3$) δ: 2.88 (3H, s), 7.09 (1H, d, J=4.1 Hz), 7.54 (1H, d, J=4.1 Hz), 8.00 (1H, s), 8.81 (1H, s)

b) 7-(4-Methylthiazol-5-yl)carbonyl-2-(tri-n-butylstannyl)imidazo[5,1-b]thiazole The title compound (254 mg) was prepared in substantially the same manner as in step c) of Synthesis Example 1, except that 502 mg of 7-(4-methylthiazol-5-yl)carbonylimidazo[5,1-b]thiazole, 0.598 ml of tri-n- butylstannyl chloride, and 4.0 ml of a 1.0 N lithium bis (trimethylsilyl)amide/THF solution were used as the starting materials.

NMR (CDCl$_3$) δ: 0.90 (9H, t, J=7.3 Hz), 1.18 (6H, m), 1.24 (6H, m), 1.34 (6H, m), 2.93 (3H, s), 7.31 (1H, s), 7.98 (1H, s), 8.84 (1H, s)

Synthesis Example 4

7-[(2S)-1-(4-Nitrobenzyloxycarbonyl)pyrrolidin-2-yl]carbonyl-2-(tri-n-butylstannyl)imidazo[5,1-b] thiazole a) 7-[[(2S)-1-(4-Nitrobenzyloxycarbonyl)pyrrolidin-2-yl] hydroxymethyl]imidazo[5,1-b]thiazole 7-[[(2S)-1-(4-Nitrobenzyloxycarbonyl)pyrrolidin-2-yl] hydroxymethyl]imidazo[5,1-b]thiazole (2.21 g) was prepared in the same manner as in step a) of Synthesis Example 1, except that 2.50 g of 7-iodoimidazo[5,1-b]thiazole and 2.32 g of (2S)-1-(4-nitrobenzyloxycarbonyl)pyrrolidine-2-aldehyde were used as the starting compounds.

NMR (CDCl$_3$) δ: 1.7–2.3 (4H, m), 3.4–3.6 (2H, m), 4.15–4.25 (1H, m), 4.87 (1H, d, J=8.7 Hz), 5.30 (2H, s), 6.82 (1H, d, J=4.5 Hz), 7.37 (1H, d, J=4.5 Hz), 7.56 (2H, d, J=8.7 Hz), 7.93 (1H, s), 8.24 (2H, d, J=8.7 Hz)

b) 7-[(2S)-1-(4-Nitrobenzyloxycarbonyl)pyrrolidin-2-yl] carbonylimidazo[5,1-b]thiazole 7-[(2S)-1-(4-Nitrobenzyloxycarbonyl)pyrrolidin-2-yl] carbonylimidazo[5,1-b]thiazole (1.79 g) was prepared in the same manner as in step b) of Synthesis Example 1, except that 2.21 g of 7-[[(2S)-1-(4-nitrobenzyloxycarbonyl) pyrrolidin-2-yl]hydroxymethyl]-imidazo[5,1-b]thiazole was used as the starting compound.

NMR (CDCl$_3$) δ: 1.9–2.5 (4H, m), 3.55–3.85 (2H, m), 4.9–5.3 (2H, m), 5.45–5.55 (1H, m), 7.05–7.6 (4H, m), 7.9–8.25 (3H, m)

c) 7-[(2S)-1-(4-Nitrobenzyloxycarbonyl)pyrrolidin-2-yl] carbonyl-2-(tri-n-butylstannyl)imidazo[5,1-b]thiazole The title compound (1.82 g) was prepared in the same manner as in step c) of Synthesis Example 1, except that 2.15 g of 7-[(2S)-1-(4-nitrobenzyloxycarbonyl)pyrrolidin-2-yl]carbonylimidazo-[5,1-b]thiazole was used as the starting compound.

NMR (CDCl$_3$) δ: 0.91 (9H, t, J=7.2 Hz), 1.2–1.3 (6H, m), 1.3–1.4 (6H, m), 1.5–1.7 (6H, m), 1.9–2.5 (4H, m), 3.55–3.85 (2H, m), 4.9–5.3 (2H, m), 5.45–5.55 (1H, m), 7.2–7.55 (3H, m), 7.9–8.25 (3H, m)

Synthesis Example 5

7-(Pyrimidin-5-yl)carbonyl-2-(tri-n-butylstannyl) imidazo[5,1-b]thiazole a) 7-[(Pyrimidin-5-yl)hydroxymethyl]imidazo[5,1-b]-thiazole 5-Bromopyrimidine (1.11 g) was dissolved in a solution of 7 ml of tetrahydrofuran and 14 ml of diethyl ether to prepare a solution. Under an argon atmosphere, a 1.6 N n-butyllithium/n-hexane solution (4.56 ml) was added dropwise to the solution at −78° C., and the mixture was stirred for 30 min. Next, 7-formylimidazo[5,1b]-thiazole (608 mg)/ tetrahydrofuran (16 ml) was added dropwise thereto at −78° C. under an argon atmosphere. The mixture was stirred at that temperature for 30 min. The temperature was then raised to room temperature, and 70 ml of ethyl acetate was added thereto. The organic layer was washed twice with semisaturated brine and once with saturated brine. The washed organic layer was dried over anhydrous magnesium sulfate and was filtered. The solvent was removed by distillation under the reduced pressure, and the residue was purified by column chromatography on silica gel (chloroform/methanol=40/1→25/1→10/1) to give 398 mg of 7-[(pyrimidin-5-yl)hydroxymethyl]imidazo[5,1-b] thiazole.

NMR (DMSO-d$_6$) δ: 5.88 (1H, d, J=4.6 Hz), 6.33 (1H, d, J=4.6 Hz), 7.15 (1H, d, J=4.2 Hz), 7.81 (1H, d, J=4.2 Hz), 8.11 (1H, s), 8.79 (2H, s), 9.09 (1H, s)

b) 7-(Pyrimidin-5-yl)carbonyl-2-(tri-n-butylstannyl)-imidazo[5,1-b]thiazole

A ketone compound (217 mg) was prepared in substantially the same manner as in step b) of Synthesis Example 1, except that 398 mg of 7-[(pyrimidin-5-yl)hydroxymethyl] imidazo[5,1-b]thiazole and 400 mg of manganese dioxide were used as the starting compounds. 7-(Pyrimidin-5-yl) carbonyl-2-(tri-n-butylstannyl)-imidazo[5,1-b]thiazole (68 mg) was prepared in substantially the same manner as in step c) of Synthesis Example 1, except that 46 mg of the ketone compound, 0.124 ml of tri-n-butylstannyl chloride, and 0.900 ml of a 1.0 N lithium bis(trimethylsilyl)amide/THF solution were used as the starting materials.

NMR (CDCl$_3$) δ: 0.92 (9H, t, J=7.3 Hz), 1.25–1.33 (6H, m), 1.36–1.49 (6H, m), 1.53–1.62 (6H, m), 7.38 (1H, t, J=7.1 Hz), 8.04 (1H, s), 9.34 (1H, s), 9.78 (1H, s)

Synthesis Example 6

7-(Thiophen-2-yl)carbonyl-2-(tri-n-butylstannyl) imidazo[5,1-b]thiazole a) 7-(Thiophen-2-yl)carbonylimidazo[5,1-b]thiazole 7-(Thiophen-2-yl)carbonylimidazo[5,1-b]thiazole (1.37 g) was prepared in the same manner as in step a) of Synthesis Example 3, except that 1.50 g of 7-iodoimidazo[5,1-b] thiazole and 0.561 ml of thiophene-2-aldehyde were used as the starting compounds.

NMR (CDCl$_3$) δ: 6.98 (1H, d, J=4.1 Hz), 7.05 (1H, m), 7.44 (1H, d, J=4.1 Hz), 7.53 (1H, m), 7.90 (1H, s), 8.50 (1H, m)

b) 7-(Thiophen-2-yl)carbonyl-2-(tri-n-butylstannyl)-imidazo[5,1-b]thiazole

The title compound (923 mg) was prepared in substantially the same manner as in step c) of Synthesis Example 1, except that 550 mg of 7-(thiophen-2-yl)carbonylimidazo[5, 1-b]thiazole, 0.701 ml of tri-n-butylstannyl chloride, and 3.6 ml of a 1.0 N lithium bis(trimethylsilyl)amide/THF solution were used as the starting materials.

NMR (CDCl$_3$) δ: 0.85 (9H, t, J=7.3 Hz), 1.04 (6H, m), 1.11 (6H, m), 1.42 (6H, m), 7.03 (1H, m), 7.18 (1H, s), 7.48 (1H, m), 7.95 (1H, s), 8.47 (1H, s)

Synthesis Example 7

7-[5-(t-Butyldimethylsilyl-oxymethyl)pyridin-3-yl] carbonyl-2-(tri-n-butylstannyl)-imidazo[5,1-b] thiazole a) 7-[[5-(t-Butyldimethylsilyloxymethyl)pyridin-3-yl]-hydroxymethyl]imidazo[5,1-b]thiazole A solution of 2.49 g of 5-bromo-3-(t-butyldimethylsilyloxymethyl)pyridine in 25 ml of dry diethyl ether was cooled to −85° C. under an argon atmosphere, and 5.56 ml of a 1.57 N n-butyllithium/hexane solution was added dropwise to the cooled solution over a period of 10 min. The mixture was stirred at that temperature for 30 min, and a solution of 881 mg of 7-formylimidazo [5,1-b]thiazole in 20 ml of dry THF was then added thereto, followed by further mixing at the same temperature for 30 min. Water was added to the reaction solution. The mixture was extracted three times with chloroform. The organic layer was dried over anhydrous magnesium sulfate and was then concentrated under the reduced pressure. The residue was purified by column chromatography on silica gel (ethyl acetate:methanol=10:1) to give 803 mg of 7-[[5-(t-butyldimethylsilyloxymethyl)pyridin-3-yl]hydroxymethyl] imidazo[5,1-b]thiazole.

NMR (CDCl$_3$) δ: 0.07 (6H, s), 0.99 (9H, s), 4.76 (2H, s), 6.02 (1H, s), 6.71 (1H, d, J=4.1 Hz), 7.32 (1H, d, J=4.1 Hz), 7.77 (1H, s), 7.95 (1H, s), 8.55 (1H, m), 8.61 (1H, m)

b) 7-[5-(t-Butyldimethylsilyloxymethyl)pyridin-3-yl]-carbonylimidazo[5,1-b]thiazole Manganese dioxide (1.43 g) was added to a solution of 803 mg of 7-[[5-(t-butyldimethylsilyloxymethyl)-pyridin-3-yl]hydroxymethyl]imidazo[5,1-b]thiazole in 10 ml of dichloromethane, and the mixture was stirred at room temperature for 16 hr. The reaction solution was filtered through Celite, followed by washing with dichloromethane. The filtrate was concentrated under the reduced pressure to give 712 mg of 7-[5-(t-butyldimethylsilyloxymethyl)pyridin-3-yl]carbonyl imidazo[5,1-b]thiazole.

NMR (CDCl$_3$) δ: 0.10 (6H, s), 0.94 (9H, s), 4.85 (2H, s), 7.16 (1H, d, J=4.0 Hz), 7.58 (1H, d, J=4.0 Hz), 8.08 (1H, s), 8.72 (1H, m), 8.76 (1H, m), 9.60 (1H, m)

c) 7-[5-(t-Butyldimethylsilyloxymethyl)pyridin-3-yl]-carbonyl-2-(tri-n-butylstannyl)imidazo[5,1-b]thiazole The title compound (926 mg) was prepared in substantially the same manner as in step c) of Synthesis Example 1, except that 712 mg of 7-[5-(t-butyldimethylsilyloxymethyl) pyridin-3-yl]carbonyl imidazo[5,1-b]thiazole, 0.572 ml of tri-n-butylstannyl chloride, and 2.9 ml of a 1.0 N lithium bis(trimethylsilyl)amide/THF solution were used as the starting materials.

NMR (CDCl$_3$) δ: 0.10 (6H, s), 0.98 (9H, t, J=7.2 Hz), 1.00 (9H, s), 1.18 (6H, m), 1.32 (6H, m), 1.54 (6H, m), 4.85 (2H, s), 7.31 (1H, s), 7.98 (1H, S), 8.72 (2H, m), 9.58 (1H, m)

Synthesis Example 8

7-(6-Methylpyridin-3-yl)carbonyl-2-(tri-n-butylstannyl)imidazo[5,1-b]thiazole a) 7-(6-Methylpyridin-3-yl)carbonylimidazo[5,1-b]-thiazole 7-(6-Methylpyridin-3-yl)carbonylimidazo[5,1-b]-thiazole (885 mg) was prepared in the same manner as in step a) of Synthesis Example 3, except that 1.10 g of 7-iodoimidazo[5,1-b]thiazole and 532 mg of 2-methylpyridine-5-aldehyde were used as the starting compounds.

NMR (CDCl$_3$) δ: 2.51 (3H, s), 7.02 (1H, d, J=4.1 Hz), 7.18 (1H, m), 7.50 (1H, d, J=4.1 Hz), 7.97 (1H, s), 8.61 (1H, m), 9.48 (1H, m)

b) 7-(6-Methylpyridin-3-yl)carbonyl-2-(tri-n-butylstannyl) imidazo[5,1-b]thiazole The title compound (606 mg) was prepared in substantially the same manner as in step c) of Synthesis Example 1, except that 447 mg of 7-(6-methylpyridin-3-yl) carbonylimidazo[5,1-b]thiazole, 0.552 ml of tri-n-butylstannyl chloride, and 3.2 ml of a 1.0 N lithium bis (trimethylsilyl)amide/THF solution were used as the starting materials.

NMR (CDCl$_3$) δ: 0.85 (9H, t, J=7.3 Hz), 1.10 (6H, m), 1.20 (6H, m), 1.43 (6H, m), 2.46 (3H, s), 7.16 (1H, m), 7.20 (1H, s), 7.85 (1H, s), 8.57 (1H, m), 9.40 (1H, m)

Synthesis Example 9

7-(5-Methylthiopyridin-3-yl)carbonyl-2-(tri-n-butylstannyl)imidazo[5,1-b]thiazole a) 7-[(5-Methylthiopyridin-3-yl)hydroxymethyl]imidazo-[5,1-b]thiazole 7-[(5-Methylthiopyridin-3-yl)hydroxymethyl]imidazo-[5,1-b]thiazole (119 mg) was prepared in substantially the same manner as in step a) of Synthesis Example 5, except that 204 mg of 3-bromo-5-methylthiopyridine, 0.656 ml of a 1.6 N n-butyllithium/n-hexane solution, and 102 mg of 7-formylimidazo[5,1-b]thiazole were used as the starting materials.

NMR (DMSO-d$_6$) δ: 2.49 (3H, s), 5.78 (1H, d, J=4.6 Hz), 6.13 (1H, d, J=4.4 Hz), 7.11 (1H, d, J=4.4 Hz), 7.67 (1H, s), 7.80 (1H, d, J=4.2 Hz), 8.10 (1H, s), 8.36 (2H, s)

b) 7-(5-Methylthiopyridin-3-yl)carbonyl-2-(tri-n-butylstannyl)imidazo[5,1-b]thiazole A ketone compound (408 mg) was prepared in substantially the same manner as in step b) of Synthesis Example 1, except that 430 mg of 7-[(5-methylthiopyridin-3-yl) hydroxymethyl]imidazo[5,1-b]thiazole and 320 mg of manganese dioxide were used as the starting compounds. 7-(5-Methylthiopyridin-3-yl)carbonyl-2-(tri-n-butylstannyl) imidazo[5,1-b]thiazole (179 mg) was prepared in substantially the same manner as in step c) of Synthesis Example 1, except that 138 mg of the ketone compound, 0.300 ml of tri-n-butylstannyl chloride, and 2.25 ml of a 1.0 N lithium bis(trimethylsilyl)amide/THF solution were used as the starting materials.

NMR (CDCl$_3$) δ: 0.93 (9H, t, J=7.3 Hz), 1.15–1.23 (6H, m), 1.27–1.35 (6H, m), 1.56–1.64 (6H, m), 7.35 (1H, t, J=7.3 Hz), 8.02 (1H, s), 8.64 (2H, s), 9.51 (1H, s)

Synthesis Example 10

7-(Quinolin-3-yl)carbonyl-2-(tri-n-butylstannyl) imidazo[5,1-b]thiazole a) 7-[(Quinolin-3-yl)hydroxymethyl]imidazo[5,1-b]-thiazole 7-[(Quinolin-3-yl)hydroxymethyl]imidazo[5,1-b]-thiazole (203 mg) was prepared in substantially the same manner as in step a) of Synthesis Example 1, except that 0.25 g of 7-iodoimidazo[5,1-b]thiazole, 1.17 ml of a 0.93 M methylmagnesium bromide/tetrahydrofuran solution, and 173 mg of 3-quinolinecarboxyaldehyde were used as the starting materials.

NMR (DMSO-d$_6$) δ: 6.01 (1H, d, J=4.4 Hz), 6.26 (1H, d, J=4.4 Hz), 7.09 (1H, d, J=4.1 Hz), 7.58 (1H, t, J=7.8 Hz), 7.71 (1H, t, J=7.9 Hz), 7.80 (1H, d, J=4.1 Hz), 8.00 (2H, d, J=8.0 Hz), 8.10 (1H, s), 8.90 (1H, s)

b) 7-(Quinolin-3-yl)carbonyl-2-(tri-n-butylstannyl)-imidazo [5,1-b]thiazole

A ketone compound (327 mg) was prepared in substantially the same manner as in step b) of Synthesis Example 1, except that 577 mg of 7-[(quinolin-3-yl)hydroxymethyl] imidazo[5,1-b]thiazole and 421 mg of manganese dioxide were used as the starting compounds. 7-(Quinolin-3-yl) carbonyl-2-(tri-n-butylstannyl)imidazo-[5,1-b]thiazole (73 mg) was prepared in substantially the same manner as in step c) of Synthesis Example 1, except that 64 mg of the ketone compound, 0.140 ml of tri-n-butylstannyl chloride, and 1.50 ml of a 1.0 N lithium bis(trimethylsilyl)amide/THF solution were used as the starting materials.

NMR (CDCl$_3$) δ: 0.93 (9H, t, J=7.3 Hz), 1.14–1.24 (6H, m), 1.33–1.42 (6H, m), 1.61–1.68 (6H, m), 7.38 (1H, t, J=7.3 Hz), 7.61 (1H, t, J=8.0 Hz), 7.81 (1H, m), 8.03 (1H, d, J=8.0 Hz), 8.07 (1H, s), 8.16 (1H, d, J=8.6 Hz), 9.57 (1H, s), 9.84 (1H, s)

Synthesis Example 11

7-([3,3']Bipyridinyl-5-yl)carbonylimidazo[5,1-b]thiazole a) 7-[(5-Bromopyridin-3-yl)hydroxymethyl]imidazo[5,1-b]thiazole

7-[(5-Bromopyridin-3-yl)hydroxymethyl]imidazo[5,1-b]thiazole (2.77 g) was prepared in substantially the same manner as in step a) of Synthesis Example 1, except that 2.50 g of 7-iodoimidazo[5,1-b]thiazole, 12.2 ml of a 0.93 M methylmagnesium bromide/tetrahydrofuran solution, and 2.05 g of 3-bromo-5-formylpyridine were used as the starting materials.

NMR (CDCl$_3$) δ: 4.86 (1H, s), 6.04 (1H, s), 6.74 (1H, d, J=4.2 Hz), 7.35 (1H, d, J=4.4 Hz), 7.97 (1H, s), 8.04 (1H, s), 8.62 (2H, s)

b) 7-([3,3']Bipyridinyl-5-yl)carbonylimidazo[5,1-b]thiazole

A ketone compound (1.96 g) was prepared in substantially the same manner as in step b) of Synthesis Example 1, except that 2.77 g of 7-[(5-bromopyridin-3-yl)hydroxymethyl]imidazo[5,1-b]thiazole and 2.00 g of manganese dioxide were used as the starting compounds. The ketone compound (616 mg) was dissolved in 20 ml of N,N-dimethylformamide to prepare a solution. Diethyl(3-pyridyl)borane (588 mg), 232 mg of tetrakis(triphenylphosphine)palladium(0), and 552 mg of potassium carbonate were added to the solution at room temperature under an argon atmosphere. The mixture was stirred at 90° C. for 2.5 hr. Ethyl acetate (200 ml) was added to the reaction solution, and the organic layer was washed four times with 80 ml of water and once with saturated brine. The washed organic layer was dried over anhydrous magnesium sulfate and was filtered. The solvent was removed by distillation under the reduced pressure, and the residue was purified by chromatography on silica gel (chloroform/methanol=20/1 →10/1) to give 428 mg of 7-([3,3']bipyridinyl-5-yl)carbonylimidazo[5,1-b]thiazole.

NMR (CDCl$_3$) δ: 7.21 (1H, d, J=3.9 Hz), 7.45 (1H, m), 7.65 (1H, d, J=4.1 Hz), 8.00 (1H, m), 8.11 (1H, s), 8.68 (1H, d, J=4.9 Hz), 8.95 (1H, s), 9.05 (1H, s), 9.08 (1H, s), 9.76 (1H, s)

Synthesis Example 12

7-(5-Phenylpyridin-3-yl)carbonyl-2-(tri-n-butylstannyl)imidazo[5,1-b]thiazole a) 7-(5-Phenylpyridin-3-yl)carbonylimidazo[5,1-b]-thiazole

A ketone compound (1.96 g) was prepared in substantially the same manner as in step b) of Synthesis Example 1, except that 2.77 g of 7-[(5-bromopyridin-3-yl)hydroxymethyl]imidazo[5,1-b]thiazole and 2.00 g of manganese dioxide were used as the starting compounds. 7-(5-Phenylpyridin-3-yl)carbonylimidazo[5,1-b]thiazole (285 mg) was prepared in substantially the same manner as in step b) of Synthesis Example 11, except that 308 mg of the ketone compound, 240 mg of phenylboronic acid, 116 mg of tetrakis(triphenylphosphine)palladium(0), and 276 mg of potassium carbonate were used as the starting compounds.

NMR (CDCl$_3$) δ: 7.20 (1H, d, J=4.1 Hz), 7.45–7.53 (3H, m), 7.64 (1H, d, J=3.9 Hz), 7.65–7.70 (2H, m), 8.10 (1H, s), 9.01 (2H, s), 9.72 (1H, s)

b) 7-(5-Phenylpyridin-3-yl)carbonyl-2-(tri-n-butylstannyl)imidazo[5,1-b]thiazole 7-(5-Phenylpyridin-3-yl)carbonyl-2-(tri-n-butylstannyl)imidazo[5,1-b]thiazole (297 mg) was prepared in substantially the same manner as in step c) of Synthesis Example 1, except that 275 mg of 7-(5-phenylpyridin-3-yl)carbonylimidazo[5,1-b]thiazole, 0.330 ml of tri-n-butylstannyl chloride, and 1.80 ml of a 1.0 N lithium bis(trimethylsilyl)amide/THF solution were used as the starting materials.

NMR (CDCl$_3$) δ: 0.93 (9H, t, J=7.3 Hz), 1.15–1.22 (6H, m), 1.28–1.34 (6H, m), 1.59–1.64 (6H, m), 7.37 (1H, t, J=7.3 Hz), 7.41–7.45 (3H, m), 7.67–7.70 (2H, m), 8.03 (1H, s), 8.99 (2H, m), 9.69 (1H, s)

Synthesis Example 13

7-(Thiazol-5-yl)carbonyl-2-(tri-n-butylstannyl)imidazo[5,1-b]thiazole a) 7-(Thiazol-5-yl)carbonylimidazo[5,1-b]thiazole 7-(Thiazol-5-yl)carbonylimidazo[5,1-b]thiazole (187 mg) was prepared in the same manner as in step a) of Synthesis Example 3, except that 265 mg of 7-iodoimidazo[5,1-b]thiazole and 119 mg of thiazole-5-aldehyde were used as the starting compounds.

NMR (CDCl$_3$) δ: 7.18 (1H, d, J=4.1 Hz), 7.62 (1H, d, J=4.1 Hz), 8.10 (1H, s), 9.03 (1H, S), 9.33 (1H, s)

b) 7-(Thiazol-5-yl)carbonyl-2-(tri-n-butylstannyl)imidazo[5,1-b]thiazole

The title compound (260 mg) was prepared in substantially the same manner as in step c) of Synthesis Example 1, except that 187 mg of 7-(thiazol-5-yl)carbonylimidazo[5,1-b]thiazole, 0.235 ml of tri-n-butylstannyl chloride, and 1.2 ml of a 1.0 N lithium bis(trimethylsilyl)amide/THF solution were used as the starting materials.

NMR (CDCl$_3$) δ: 0.90 (9H, t, J=7.3 Hz), 1.22 (6H, m), 1.35 (6H, m), 1.58 (6H, m), 7.38 (1H, s), 8.02 (1H, s), 9.02 (1H, s), 9.28 (1H, s)

Synthesis Example 14

7-[(2S,4R)-4-t-Butyldimethylsilyloxy-1-(4-nitrobenzyloxycarbonyl)pyrrolidin-2-yl]carbonyl-2-(tri-n-butylstannyl)imidazo[5,1-b]thiazole a) 7-[[(2S,4R)-4-t-Butyldimethylsilyloxy-1-(4-nitrobenzyloxycarbonyl)pyrrolidin-2-yl]hydroxymethyl]imidazo[5,1-b]thiazole 7-[[(2S,4R)-4-t-Butyldimethylsilyloxy-1-(4-nitrobenzyloxycarbonyl)pyrrolidin-2-yl]hydroxymethyl]-imidazo[5,1-b]thiazole (4.18 g) was prepared in the same manner as in step a) of Synthesis Example 1, except that 3.39 g of 7-iodoimidazo[5,1-b]thiazole and 4.61 g of (2S,4R)-4-t-butyldimethylsilyloxy-1-(4-nitrobenzyloxycarbonyl)pyrrolidine-2-aldehyde were used as the starting compounds.

NMR (CDCl$_3$) δ: 0.01 (6H, s), 0.82 (9H, s), 1.7–2.3 (2H, m), 3.35–3.7 (2H, m), 4.1–4.2 (1H, m), 4.3–4.4 (1H, m), 4.85–4.95 (1H, m), 5.26 (1H, d, J=13.5 Hz), 5.37 (1H, d, J=13.5 Hz), 5.45–5.5 (1H, m), 6.82 (1H, d, J=4.2 Hz), 7.37 (1H, d, J=4.2 Hz), 7.54 (2H, d, J=8.1 Hz), 7.92 (1H, s), 8.24 (2H, d, J=8.1 Hz)

b) 7-[(2S,4R)-4-t-Butyldimethylsilyloxy-1-(4-nitrobenzyloxycarbonyl)pyrrolidin-2-yl]carbonylimidazo[5,1-b]thiazole 7-[(2S,4R)-4-t-Butyldimethylsilyloxy-1-(4-nitrobenzyloxycarbonyl)pyrrolidin-2-yl]carbonylimidazo[5,1-b]thiazole (3.89 g) was prepared in the same manner as in step b) of Synthesis Example 1, except that 4.18 g of 7-[[(2S,4R)-4-t-butyldimethylsilyloxy-1-(4-nitrobenzyloxycarbonyl)pyrrolidin-2-yl]hydroxymethyl]imidazo[5,1-b]thiazole was used as the starting compound.

NMR (CDCl₃) δ: 0.08 (6H, s), 0.89 (9H, s), 2.1–2.2 (1H, m), 2.3–2.5 (1H, m), 3.5–3.6 (1H, m), 3.8–3.9 (1H, m), 4.45–4.55 (1H, m), 4.85–5.35 (2H, m), 5.5–5.7 (1H, m), 7.1–7.15 (1H, m), 7.2–7.55 (3H, m), 7.85–8.2 (3H, m)

c) 7-[(2S,4R)-4-t-Butyldimethylsilyloxy-1-(4-nitrobenzyloxycarbonyl)pyrrolidin-2-yl]carbonyl-2-(tri-n butylstannyl)imidazo[5,1-b]thiazole The title compound (707 mg) was prepared in the same manner as in step c) of Synthesis Example 1, except that 725 mg of 7-[(2S,4R)-4-t-butyldimethylsilyloxy-1-(4-nitrobenzyloxycarbonyl)pyrrolidin-2-yl]carbonyl-imidazo [5,1-b]thiazole was used as the starting compound.

NMR (CDCl₃) δ: 0.07 (6H, s), 0.8–1.0 (18H, m), 1.1–1.4 (12H, m), 1.5–1.7 (6H, m), 2.1–2.25 (1H, m), 2.35–2.45 (1H, m), 3.45–3.6 (1H, m), 3.8–3.9 (1H, m), 4.5–4.6 (1H, m), 4.9–5.3 (2H, m), 5.5–5.7 (1H, m), 7.2–7.55 (3H, m), 7.8–8.25 (3H, m)

Synthesis Example 15

7-[[5-(Morpholin-4-yl)methylpyridin-3-yl] hydroxymethyl]imidazo[5,1-b]-thiazole

7-[[5-(Morpholin-4-yl)methylpyridin-3-yl] hydroxymethyl]imidazo[5,1-b]thiazole (384 mg) was prepared in substantially the same manner as in step a) of Synthesis Example 5, except that 1.05 g of 4-(5-bromopyridin-3-yl)methylmorpholine, 2.70 ml of a 1.59 N nbutyllithium/n-hexane solution, and 426 mg of 7-formylimidazo[5,1-b]thiazole were used as the starting materials.

NMR (DMSO-d₆) δ: 2.46 (4H, t, J=4.6 Hz), 3.54 (2H, s), 3.69 (4H, t, J=4.6 Hz), 6.05 (1H, s), 6.71 (1H, d, J=4.2 Hz), 7.34 (1H, d, J=4.2 Hz), 7.85 (1H, s), 7.99 (1H, s), 8.54 (1H, s), 8.61 (1H, s)

Synthesis Example 16

7-[5-(2-Azidoethylthio)pyridin-3-yl]carbonyl-2-(tri-n-butylstannyl)imidazo[5,1-b]thiazole a) 7-[5-(2-Azidoethylthio)pyridin-3-yl]carbonylimidazo[5,1-b]thiazole 7-[5-(2-Azidoethylthio)pyridin-3-yl]carbonylimidazo[5,1-b]thiazole (667 mg) was prepared in the same manner as in step a) of Synthesis Example 3, except that 650 g of 7-iodoimidazo[5,1-b]thiazole and 570 mg of 3-(2-azidoethylthio)pyridine-5-aldehyde were used as the starting compounds.

NMR (CDCl₃) δ: 3.19 (2H, t, J=7.2 Hz), 3.56 (2H, t, J=7.2 Hz), 7.20 (1H, d, J=4.1 Hz), 7.65 (1H, d, J=4.1 Hz), 8.10 (1H, s), 8.76 (1H, m), 8.91 (1H, m), 9.56 (1H, m)

b) 7-[5-(2-Azidoethylthio)pyridin-3-yl]carbonyl-2-(tri-n-butylstannyl)imidazo[5,1-b]thiazole The title compound (857 mg) was prepared in substantially the same manner as in step c) of Synthesis Example 1, except that 667 mg of 7-[5-(2-azidoethylthio)pyridin-3-yl] carbonylimidazo[5,1-b]-thiazole, 0.603 ml of tri-n-butylstannyl chloride, and 3.7 ml of a 1.0 N lithium bis (trimethylsilyl)amide/THF solution were used as the starting materials.

NMR (CDCl₃) δ: 0.90 (9H, t, J=7.3 Hz), 1.24 (6H, m), 1.38 (6H, m), 1.58 (6H, m), 3.18 (2H, t, J=7.2 Hz), 3.57 (2H, t, J=7.2 Hz), 7.38 (1H, s), 8.04 (1H, s), 8.76 (1H, m), 8.86 (1H, m), 9.56 (1H, m)

Synthesis Example 17

7-[(2S,4S)-4-Azido-1-(4-nitrobenzyloxycarbonyl) pyrrolidin-2-yl]carbonyl-2-(tri-n-butylstannyl) imidazo[5,1-b]thiazole a) 7-[(2S,4R)-4-Hydroxy-1-(4-nitrobenzyloxycarbonyl) pyrrolidin-2-yl]carbonylimidazo[5,1-b]thiazole 7-[(2S,4R)-4-t-Butyldimethylsilyloxy-1-(4-nitrobenzyloxycarbonyl)pyrrolidin-2-yl]carbonyl-2-(tri-n-butylstannyl)imidazo[5,1-b]thiazole (1.15 g) was dissolved in 10 ml of a 1.6 N hydrochloric acid/methanol solution to prepare a solution which was stirred under ice cooling for 30 min. An aqueous potassium carbonate solution was added to the reaction solution, and the mixture was extracted with dichloromethane, followed by washing with brine. The organic layer was dried over anhydrous magnesium sulfate, and the solvent was then removed by distillation to give 853 mg of 7-[(2S,4R)-4-hydroxy-1-(4-nitrobenzyloxycarbonyl) pyrrolidin-2-yl]carbonylimidazo[5,1-b]thiazole.

NMR (CDCl₃) δ: 1.90 (1H, m), 2.22 (1H, m), 2.52 (1H, m), 3.66–3.78 (1H, m), 3.88 (1H, m), 4.59 (1H, br s), 4.88–5.31 (2H, m), 5.66–5.72 (1H, m), 7.13 (1H, m), 7.22–7.57 (1H, m), 7.91–8.23 (1H, m)

b) 7-[(2S,4R)-4-Methanesulfonyloxy-1-(4-nitrobenzyloxycarbonyl)pyrrolidin-2-yl]carbonylimidazo[5,1-b]thiazole 7-[(2S,4R)-4-Hydroxy-1-(4-nitrobenzyloxycarbonyl) pyrrolidin-2-yl]carbonylimidazo[5,1-b]thiazole (850 mg) was dissolved in 20 ml of dichloromethane and 7 ml of DMF under ice cooling to prepare a solution. Triethylamine (0.425 ml) and 0.19 ml of methanesulfonyl chloride were added to the solution, and the mixture was stirred for 30 min. Water was added to the reaction solution, and the mixture was extracted with dichloromethane, followed by washing twice with brine. The organic layer was dried over anhydrous magnesium sulfate, and the solvent was then removed by distillation to give 734 mg of a crude product of 7-[(2S,4R)-4-methanesulfonyloxy-1-(4-nitrobenzyloxycarbonyl) pyrrolidin-2-yl]carbonylimidazo[5,1-b]thiazole.

c) 7-[(2S,4S)-4-Azido-1-(4-nitrobenzyloxycarbonyl) pyrrolidin-2-yl]carbonylimidazo[5,1-b]thiazole Sodium azide (87 mg) was added to a solution of 552 mg of 7-[(2S,4R)-4-methanesulfonyloxy-1-(4-nitrobenzyloxycarbonyl)pyrrolidin-2-yl]carbonylimidazo[5,1-b]thiazole in 5 ml of DMF, and the mixture was stirred at 100° C. for 13 hr. Water was added to the reaction solution, and the mixture was extracted with ethyl acetate, followed by washing three times with brine. The organic layer was dried over anhydrous magnesium sulfate, and the solvent was then removed by distillation to give 474 mg of a crude product of 7-[(2S,4S)-4-azido-1-(4-nitrobenzyloxycarbonyl)pyrrolidin-2-yl]carbonylimidazo[5,1-b]thiazole.

d) 7-[(2S,4S)-4-Azido-1-(4-nitrobenzyloxycarbonyl) pyrrolidin-2-yl]carbonyl-2-(tri-n-butylstannyl)imidazo-[5,1-b]thiazole The title compound (321 mg) was prepared in substantially the same manner as in step c) of Synthesis Example 1, except that 585 mg of 7-[(2S,4S)-4-azido-1-(4-nitrobenzyloxycarbonyl)pyrrolidin-2-yl]carbonylimidazo[5,1-b]thiazole, 0.396 ml of tri-n-butylstannyl chloride, and 2.8 ml of a 1.0 N lithium bis(trimethylsilyl)amide/THF solution were used as the starting materials.

NMR (CDCl₃) δ: 0.92 (9H, t, J=7.3 Hz), 1.24 (6H, m), 1.35 (6H, m), 1.56 (6H, m), 2.31 (1H, m), 2.80 (1H, m), 3.66 (1H, m), 4.20 (1H, m), 4.95–5.31 (2H, m), 5.39–5.52 (1H, m), 7.29 (1H, m), 7.54 (1H, m), 7.88–7.98 (3H, m), 8.23 (1H, m)

Example 1

Sodium (1S,5R,6S)-6-((1R)-1-hydroxyethyl)-1-methyl-2-[7-(pyridin-3-yl)carbonylimidazo[5,1-b] thiazol 2-yl]-1-carbapen-2-em-3-carboxylate (Compound No. 1)

a) 4-Nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate Under an argon atmosphere at −30° C., N,N-diisopropylethylamine (0.343 ml) was added dropwise to a solution of 474 mg of 4-nitrobenzyl (1R,3R,5R,6S)-6-((1R)-1-hydroxyethyl)-1-methyl-2-oxo-1-carbapenam-3-carboxylate in 13 ml of dry acetonitrile, and 0.218 ml of anhydrous trifluoromethanesulfonic acid was then added dropwise thereto. The mixture was stirred at that temperature for 30 min. Ethyl acetate (30 ml) was then added thereto, followed by washing with semisaturated brine, a mixed solution (pH 1.1) composed of semisaturated brine and a 1 N aqueous hydrochloric acid solution, a mixed solution (pH 8.9) composed of semisaturated brine and a saturated aqueous sodium bicarbonate solution, and semisaturated brine in that order. The organic layer was then dried over anhydrous magnesium sulfate and was filtered. The solvent was removed by distillation under the reduced pressure. The residue was dissolved in 6 ml of dry N-methylpyrrolidinone to prepare a solution. Tri-2-furylphosphine (37 mg), 343 mg of zinc chloride, 37 mg of tris(dibenzylideneacetone)dipalladium(0), and 712 mg of 7-(pyridin-3-yl)carbonyl-2-(tri-n-butylstannyl)imidazo[5,1-b]thiazole were added to the solution, and the mixture was stirred at 50° C. under an argon atmosphere for 2 hr. Ethyl acetate (30 ml) and 15 ml of a semisaturated aqueous sodium bicarbonate solution were added to the reaction solution, the mixture was stirred, and the insolubles were removed by filtration. The organic layer was separated from the filtrate, was washed three times with 20 ml of semisaturated brine, and was dried over anhydrous magnesium sulfate. The solvent was removed by distillation under the reduced pressure, and the residue was purified by column chromatography on silica gel (dichloromethane:methanol=20:1 →10:1) to give 388 mg of 4-nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate.

NMR (DMSO-$d_6$) δ: 1.19 (3H, d, J=6.0 Hz), 1.24 (3H, d, J=7.5 Hz), 3.45 (1H, dd, $J_1$=6.3 Hz, $J_2$=3.0 Hz), 3.7–3.85 (1H, m), 4.0–4.1 (1H, m), 4.68 (1H, dd, $J_1$=9.9 Hz, $J_2$=3.0 Hz), 5.17 (1H, d, J=5.4 Hz), 5.41 (1H, d, J=13.8 Hz), 5.55 (1H, d, J=13.7 Hz), 7.55–7.65 (1H, m), 7.74 (2H, d, J=9.0 Hz), 8.22 (2H, d, J=9.0 Hz), 8.47 (1H, s), 8.64 (1H, s), 8.65–8.75 (1H, m), 8.75–8.8 (1H, m), 9.55–9.6 (1H, m)

b) Sodium (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate (128.5 mg) was dissolved in 6.7 ml of THF and 6.7 ml of 1/15 M sodium phosphate buffer (pH 6.6) to prepare a solution, and 130 mg of 10% Pd-C was added to the solution. The air in the reaction vessel was replaced by hydrogen, and the contents of the reaction vessel were stirred at room temperature for 2 hr. The catalyst was removed by filtration through Celite, followed by washing with water. The filtrate was washed with ethyl acetate and was then concentrated under the reduced pressure to a volume of about 2 ml. The concentrate was purified by column chromatography on Cosmosil 40$C_{18}$-PREP (5% aqueous methanol solution) to give 40.9 mg of the title compound.

NMR ($D_2O$) δ (HOD=4.80 ppm): 1.15 (3H, d, J=7.2 Hz), 1.33 (3H, d, J=6.3 Hz), 3.45–3.6 (2H, m), 4.2–4.35 (2H, m), 7.35–7.45 (1H, m), 7.91 (1H, s), 8.07 (1H, s), 8.25–8.3 (1H, m), 8.5–8.55 (1H, m), 8.85–8.9 (1H, m)

Compound Nos. 33, 36, 37, 43, 45, 46, 47, 49, 50, 56, 57, 65, 66, 71, 73, 74, 88, 89, 96, 97, 98, 101, 107, 115, 118, 119, 124, 160, 165, and 172 were synthesized in the same manner as in Example 1.

Example 2

(1S,5R,6S)-2-[7-(1-Carbamoylmethylpyridinium-3-yl)carbonylimidazo[5,1-b]thiazol-2-yl]-6-((1R)-1-hydroxyethyl)-1-methyl-1-carbapen-2-em-3-carboxylate (intramolecular salt) (Compound No. 2)

a) 4-Nitrobenzyl (1S,5R,6S)-2-[7-(1-carbamoylmethylpyridinium-3-yl)carbonylimidazo[5,1-b]thiazol-2-yl]-6-((1R)-1-hydroxyethyl)-1-methyl-1-carbapen-2-em-3-carboxylate iodide 4-Nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate (105.5 mg) was suspended in 2 ml of acetonitrile to prepare a suspension. 2-Iodoacetamide (340 mg) was added to the suspension, and the mixture was stirred at 50° C. for 6 hr. The reaction solution was concentrated under the reduced pressure, 5 ml of ethyl acetate was added to the concentrate, and the insolubles were collected by filtration to give 157 mg of 4-nitrobenzyl (1S,5R,6S)-2-[7-(1-carbamoylmethylpyridinium-3-yl)carbonylimidazo-[5,1-b]thiazol-2-yl]-6-((1R)-1-hydroxyethyl)-1-methyl-1-carbapen-2-em-3-carboxylate iodide.

NMR (DMSO-$d_6$) δ: 1.20 (3H, d, J=6.3 Hz), 1.25 (3H, d, J=7.2 Hz), 3.47 (1H, dd, $J_1$=6.0 Hz, $J_2$=3.3 Hz), 3.75–3.85 (1H, m), 4.0–4.1 (1H, m), 4.38 (1H, dd, $J_1$=10.2 Hz, $J_2$=3.3 Hz), 5.42 (1H, d, J=13.8 Hz), 5.5–5.6 (3H, m), 7.7–7.8 (3H, m), 8.08 (1H, br s), 8.22 (2H, d, J=8.7 Hz), 8.3–8.4 (1H, m), 8.57 (1H, s), 8.69 (1H, s), 9.15–9.2 (1H, m), 9.55–9.6 (1H, m), 9.76 (1H, s)

b) (1S,5R,6S)-2-[7-(1-Carbamoylmethylpyridinium-3-yl)-carbonylimidazo[5,1-b]thiazol-2-yl]-6-((1R)-1-hydroxyethyl)-1-methyl-1-carbapen-2-em-3-carboxylate (intramolecular salt)

The title compound (31.5 mg) was prepared in the same manner as in step b) of Example 1, except that 145 mg of 4-nitrobenzyl (1S,5R,6S)-2-[7-(1-carbamoylmethylpyridinium-3-yl)carbonylimidazo[5,1-b]thiazol-2-yl]-6-((1R)-1-hydroxyethyl)-1-methyl-1-carbapen-2-em-3-carboxylate iodide was used as the starting compound.

NMR ($D_2O$) δ (HOD=4.80 ppm): 1.16 (3H, d, J=7.5 Hz), 1.33 (3H, d, J=6.0 Hz), 3.4–3.55 (2H, m), 4.15–4.35 (2H, m), 5.65 (2H, s), 7.89 (1H, s), 8.03 (1H, s), 8.1–8.2 (1H, m), 8.85–8.95 (1H, m), 9.15–9.2 (1H, m), 9.58 (1H, s)

Compound Nos. 38, 42, 44, 52, 75, 76, 77, 78, 84, 108, 116, 120, 122, 128, 138, 139, 140, 145, 153, 166, 167, and 168 were synthesized in the same manner as in Example 2.

Example 3

(1S,5R,6S)-2-[7-(1-Benzylpyridinium-3-yl)carbonylimidazo[5,1-b]thiazol-2-yl]-6-((1R)-1-hydroxyethyl)-1-methyl-1-carbapen-2-em-3-carboxylate (intramolecular salt) (Compound No. 3)

a) 4-Nitrobenzyl (1S,5R,6S)-2-[7-(1-benzylpyridinium-3-yl)carbonylimidazo[5,1-b]thiazol-2-yl]-6-((1R)-1-hydroxyethyl)-1-methyl-1-carbapen-2-em-3-carboxylate bromide 4-Nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate (78.1 mg) was suspended in 1.5 ml of acetonitrile to prepare a suspension. Benzyl bromide (0.032 ml) was added to the suspension, and the mixture was stirred at room temperature for 10 hr. The reaction solution was concentrated under the reduced pressure to give 4-nitrobenzyl (1S,5R,6S)-2-[7-(1-benzylpyridinium-3-yl)carbonylimidazo[5,1-b]thiazol-2-yl]-6-((1R)-1-hydroxyethyl)-1-methyl-1-carbapen-2-em-3-carboxylate bromide.

NMR (DMSO-d$_6$) δ: 1.19 (3H, d, J=6.0 Hz), 1.24 (3H, d, J=6.9 Hz), 3.45–3.5 (1H, m), 3.75–3.9 (1H, m), 4.0–4.1 (1H, m), 4.35–4.4 (1H, m), 5.15–5.2 (1H, m), 5.41 (1H, d, J=13.8 Hz), 6.01 (2H, s), 7.25–7.65 (5H, m), 7.74 (2H, d, J=8.7 Hz), 8.21 (2H, d, J=8.7 Hz), 8.3–8.4 (1H, m), 8.54 (1H, s), 8.67 (1H, s), 9.3–9.4 (1H, m), 9.45–9.55 (1H, m), 9.98 (1H, s)

b) (1S,5R,6S)-2-[7-(1-Benzylpyridinium-3-yl) carbonylimidazo[5,1-b]thiazol-2-yl]-6-((1R)-1-hydroxyethyl)-1-methyl-1-carbapen-2-em-3-carboxylate (intramolecular salt)

The title compound (5.6 mg) was prepared in the same manner as in step b) of Example 1, except that the whole quantity of 4-nitrobenzyl (1S,5R,6S)-2-[7-(1-benzylpyridinium-3-yl)carbonylimidazo[5,1-b]thiazol-2-yl]-6-((1R)-1-hydroxyethyl)-1-methyl-1-carbapen-2-em-3-carboxylate bromide prepared in step a) just above was used as the starting compound.

NMR (D$_2$O) δ (HOD=4.80 ppm): 1.0–1.15 (3H, m), 1.30 (3H, d, J=6.0 Hz), 3.35–3.5 (2H, m), 4.1–4.3 (2H, m), 5.86 (2H, s), 7.4–7.6 (5H, m), 7.85–8.1 (3H, m), 8.8–9.0 (2H, m), 9.6–9.7 (1H, m)

Example 4

(1S,5R,6S)-2-[7-[1-(3-Aminopropyl)-pyridinium-3-yl]carbonylimidazo[5,1-b]thiazol-2-yl]-6-((1R)-1-hydroxyethyl)-1-methyl-1-carbapen-2-em-3-carboxylate (intramolecular salt, hydrochloride) (Compound No. 4)

a) 4-Nitrobenzyl (1S,5R,6S)-2-[7-[1-(3-azidopropyl)-pyridinium-3-yl]carbonylimidazo[5,1-b]thiazol-2-yl]-6-((1R)-1-hydroxyethyl)-1-methyl-1-carbapen-2-em-3-carboxylate trifluoromethanesulfonate Under an argon atmosphere, 60 mg of 3-azido-1-propanol was dissolved in 3 ml of dichloromethane to prepare a solution which was then cooled to −60° C. 2,6-Lutidine (0.076 ml) and 0.015 ml of trifluoromethanesulfonic anhydride were added to the cooled solution, and the mixture was stirred for 20 min. Water was added to the reaction solution, and the mixture was extracted with dichloromethane, followed by washing with brine. The organic layer was dried over anhydrous magnesium sulfate, and the insolubles were removed by filtration. 4-Nitrobenzyl (1S,5R,6S)-6-((1R)-1-hydroxyethyl)-1-methyl-2-[7-(pyridin-3-yl) carbonylimidazo[5,1-b]thiazol-2-yl]-1-carbapen-2-em-3-carboxylate (310 mg) was added to the filtrate, and the mixture was stirred at room temperature for 3 hr. The reaction solution was added dropwise to 30 ml of diethyl ether, and the resultant precipitate was collected by filtration to give 452 mg of 4-nitrobenzyl (1S,5R,6S)-2-[7-[1-(3-azidopropyl)pyridinium-3-yl]carbonylimidazo[5,1-b] thiazol-2-yl]-6-((1R)-1-hydroxyethyl)-1-methyl-1-carbapen-2-em-3-carboxylate trifluoromethanesulfonate.

NMR (acetone-d$_6$) δ: 1.27 (3H, d, J=6.3 Hz), 1.34 (3H, d, J=7.3 Hz), 2.52 (2H, m), 3.47 (1H, dd, J$_1$=6.4 Hz, J$_2$=3.0 Hz), 3.67 (2H, t, J=7.0 Hz), 3.81 (1H, m), 4.18 (1H, m), 4.27 (1H, d, J=4.9 Hz), 4.47 (1H, dd, J$_1$=10.0 Hz, J$_2$=3.0 Hz), 5.11 (2H, t, J=7.0 Hz), 5.37 (1H, d, J=13.7 Hz), 5.57 (1H, d, J=13.7 Hz), 7.78 (2H, d, J=9.0 Hz), 8.18 (2H, d, J=9.0 Hz), 8.47 (1H, s), 8.59 (1H, s), 9.39 (1H, m), 9.64 (1H, m), 10.15 (1H, s)

b) (1S,5R,6S)-2-[7-[1-(3-Aminopropyl)pyridinium-3-yl] carbonylimidazo[5,1-b]thiazol-2-yl]-6-((1R)-1-hydroxyethyl)-1-methyl-1-carbapen-2-em-3-carboxylate (intramolecular salt, hydrochloride)

A reaction was carried out in the same manner as in step b) of Example 1, except that 450 mg of 4-nitrobenzyl (1S,5R,6S)-2-[7-[1-(3-azidopropyl)pyridinium-3-yl] carbonylimidazo[5,1-b]thiazol-2-yl]-6-((1R)-1-hydroxyethyl)-1-methyl-1-carbapen-2-em-3-carboxylate trifluoromethanesulfonate was used as the starting compound. The reaction product was subjected to column chromatography on Cosmosil 40C$_{18}$-PREP (10% aqueous methanol solution). The fraction, which had been eluted earlier, was collected and was then ion exchanged by column chromatography (water) on Amberlyst (A-26) to give 38 mg of the title compound.

NMR (D$_2$O) δ (HOD=4.65 ppm): 1.09 (3H, d, J=7.1 Hz), 1.18 (3H, d, J=6.4 Hz), 2.46 (2H, m), 3.14 (2H, m), 3.32–3.41 (2H, m), 4.06 (1H, dd, J$_1$=9.0 Hz, J$_2$=2.6 Hz), 4.13 (1H, m), 7.91 (1H, s), 8.08 (1H, s), 8.14 (1H, m), 8.98 (1H, m), 9.12 (1H, m), 9.67 (1H, s)

Compound Nos. 32, 62, 64, 70, 82, 86, 87, 90, 91, 99, 103, 121, 129, 130, 131, 135, 136, 137, 141, 142, 144, 146, 147, 149, 150, 151, 152, 154, 155, 156, 157, 158, 159, 161, 162, 163, 164, 170, 171, 174, and 175 were synthesized in the same manner as in Example 4.

Example 5

(1S,5R,6S)-2-[7-[1-(3-Aminopropyl)-1,4,5,6-tetrahydropyridin-3-yl]carbonylimidazo[5,1-b] thiazol-2-yl]-6-((1R)-1-hydroxyethyl)-1-methyl-1-carbapen-2-em-3-carboxylate (Compound No. 5)

In the column chromatography on Cosmosil 40C$_{18}$-PREP (10% aqueous methanol solution) in step b) of Example 4, the fraction, which had been eluted later, was collected to give 14 mg of the title compound.

NMR (D$_2$O) δ (HOD=4.65 ppm): 1.13 (3H, d, J=7.3 Hz), 1.21 (3H, d, J=6.3 Hz), 1.78 (2H, m), 1.95 (2H, m), 2.23 (2H, m), 2.95 (2H, m), 3.19 (2H, m), 3.34 (2H, m), 3.38–3.50 (2H, m), 4.13–4.21 (2H, m), 7.82 (1H, s), 7.97 (1H, s), 8.25 (1H, s)

Example 6

(1S,5R,6S)-6-((1R)-1-Hydroxyethyl)-1-methyl-2-[7-(1-methylpyridinium-3-yl)carbonylimidazo[5,1-b]-thiazol-2-yl]-1-carbapen-2-em-3-carboxylate (intramolecular salt) (Compound No. 6)

a) 4-Nitrobenzyl (1S,5R,6S)-6-((1R)-1-hydroxyethyl)-1-methyl-2-[7-(1-methylpyridinium-3-yl)carbonylimidazo-[5,1-b]thiazol-2-yl]-1-carbapen-2-em-3-carboxylate trifluoromethanesulfonate 4-Nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate (240 mg) was suspended in 10 ml of dichloromethane to prepare a suspension. Methyl trifluoromethanesulfonate (0.047 ml) was added to the suspension, and the mixture was stirred at room temperature for 20 min. The reaction solution was concentrated under the reduced pressure to give 333 mg of 4-nitrobenzyl (1S,5R,6S)-6-((1R)-1-hydroxyethyl)-1-methyl-2-[7-(1-methylpyridinium-3-yl)carbonylimidazo-[5,1-b]thiazol-2-yl]-1-carbapen-2-em-3-carboxylate trifluoromethanesulfonate.

NMR (DMSO-d$_6$) δ: 1.19 (3H, d, J=6.4 Hz), 1.25 (3H, d, J=7.1 Hz), 3.47 (1H, dd, J$_1$=6.0 Hz, J$_2$=3.0 Hz), 3.79 (1H, m), 4.06 (1H, m), 4.38 (1H, dd, J$_1$=10 Hz, J$_2$=2.9 Hz), 4.47 (3H, s), 5.17 (1H, d, J=5.1 Hz), 5.42 (1H, d, J=13.6 Hz), 5.55

(1H, d, J=13.6 Hz), 7.76 (2H, d, J=9.1 Hz), 8.22 (2H, d, J=9.1 Hz), 8.32 (1H, m), 8.56 (1H, s), 8.67 (1H, s), 9.16 (1H, m), 9.47 (1H, m), 9.78 (1H, s)

b) (1S,5R,6S)-6-((1R)-1-Hydroxyethyl)-1-methyl-2-[7-(1-methylpyridinium-3-yl)carbonylimidazo[5,1-b]thiazol-2-yl]-1-carbapen-2-em-3-carboxylate (intramolecular salt)

The title compound (36 mg) was prepared in the same manner as in step b) of Example 1, except that 333 mg of 4-nitrobenzyl (1S,5R,6S)-6-((1R)-1-hydroxyethyl)-1-methyl-2-[7-(1-methylpyridinium-3-yl)carbonylimidazo-[5,1-b]thiazol-2-yl]-1-carbapen-2-em-3-carboxylate trifluoromethanesulfonate was used as the starting compound.

NMR ($D_2O$) δ (HOD=4.65 ppm): 1.08 (3H, d, J=7.1 Hz), 1.20 (3H, d, J=6.3 Hz), 3.33–3.41 (2H, m), 4.08 (1H, dd, $J_1$=9.3 Hz, $J_2$=2.7 Hz), 4.14 (1H, m), 4.40 (3H, s), 7.87 (1H, s), 8.00 (1H, s), 8.03 (1H, s), 8.83 (1H, s), 9.02 (1H, s), 9.51 (1H, s)

Compound Nos. 39, 41, 51, 59, 112, and 127 were synthesized in the same manner as in Example 6.

Example 7

Sodium (1S,5R,6S)-6-((1R)-1-hydroxyethyl)-1-methyl-2-[7-(pyridin-4-yl)carbonylimidazo[5,1-b]thiazol-2-yl]-1-carbapen-2-em-3-carboxylate (Compound No. 7)

a) 4-Nitrobenzyl (1S,5R,6S)-6-((1R)-1-hydroxyethyl)-1-methyl-2-[7-(pyridin-4-yl)carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[7-(pyridin-4-yl)carbonylimidazo[5,1-b]thiazol-2-yl]-1-carbapen-2-em-3-carboxylate (1.23 g) was prepared in the same manner as in step a) of Example 1, except that 1.33 g of 4-nitrobenzyl (1R,3R,5R,6S)-6-((1R)-1-hydroxyethyl)-1-methyl-2-oxo-1-carbapenam-3-carboxylate and 2.00 g of 7-(pyridin-4-yl)carbonyl-2-(tri-n-butylstannyl)imidazo[5,1-b]thiazole were used as the starting compounds.

NMR ($CDCl_3$) δ: 1.34 (3H, d, J=7.2 Hz), 1.41 (3H, d, J=6.3 Hz), 3.41 (1H, dd, $J_1$=6.6 Hz, $J_2$=3.0 Hz), 3.5–3.6 (1H, m), 4.3–4.4 (1H, m), 4.40 (1H, dd, $J_1$=9.6 Hz, $J_2$=3.0 Hz), 5.29 (1H, d, J=13.5 Hz), 5.54 (1H, d, J=13.5 Hz), 7.69 (2H, d, J=8.7 Hz), 8.09 (1H, s), 8.25 (2H, d, J=8.7 Hz), 8.3–8.35 (2H, m), 8.57 (1H, s), 8.8–8.85 (2H, m)

b) Sodium (1S,5R,6S)-6-((1R)-1-hydroxyethyl)-1-methyl-2-[7-(pyridin-4-yl)carbonylimidazo[5,1-b]thiazol-2-yl]-1-carbapen-2-em-3-carboxylate The title compound (74.4 mg) was prepared in the same manner as in step b) of Example 1, except that 290 mg of 4-nitrobenzyl (1S,5R,6S)-6-((1R)-1-hydroxyethyl)-1-methyl-2-[7-(pyridin-4-yl)carbonylimidazo[5,1-b]thiazol-2-yl]-1-carbapen-2-em-3-carboxylate was used as the starting compound.

NMR ($D_2O$) δ (HOD=4.80 ppm): 1.16 (3H, d, J=6.3 Hz), 1.34 (3H, d, J=6.3 Hz), 3.4–3.6 (2H, m), 4.2–4.35 (2H, m), 7.7–7.8 (2H, m), 7.96 (1H, s), 8.11 (1H, s), 8.5–8.6 (2H, m)

Example 8

(1S,5R,6S)-2-[7-(1-Carbamoylmethylpyridinium-4-yl)(hydroxy)methylimidazo[5,1-b]thiazol-2-yl]-6-((1R)-1-hydroxyethyl)-1-methyl-1-carbapen-2-em-3-carboxylate (intramolecular salt) (a mixture of diastereomers) (Compound No. 8)

a) 4-Nitrobenzyl (1S,5R,6S)-2-[7-(1-carbamoylmethylpyridinium-4-yl)carbonylimidazo[5,1-b]thiazol-2-yl]-6-((1R)-1-hydroxyethyl)-1-methyl-1-carbapen-2-em-3-carboxylate iodide 4-Nitrobenzyl (1S,5R,6S)-2-[7-(1-carbamoylmethylpyridinium-4-yl)carbonylimidazo[5,1-b]thiazol-2-yl]-6-((1R)-1-hydroxyethyl)-1-methyl-1-carbapen-2-em-3-carboxylate iodide (426 mg) was prepared in the same manner as in step a) of Example 2, except that 327 mg of 4-nitrobenzyl (1S,5R,6S)-6-((1R)-1-hydroxyethyl)-1-methyl-2-[7-(pyridin-4-yl)carbonylimidazo[5,1-b]thiazol 2-yl]-1-carbapen-2-em-3-carboxylate was used as the starting compound.

NMR (DMSO-$d_6$) δ: 1.20 (3H, d, J=6.3 Hz), 1.25 (3H, d, J=7.5 Hz), 3.4–3.5 (1H, m), 3.7–3.9 (1H, m), 4.0–4.1 (1H, m), 4.35–4.4 (1H, m), 5.42 (1H, d, J=13.5 Hz), 5.50 (2H, s), 5.55 (1H, d, J=13.5 Hz), 7.7–7.8 (3H, m), 8.08 (1H, s), 8.22 (2H, d, J=9.0 Hz), 8.54 (1H, s), 8.68 (1H, s), 8.8–8.9 (2H, m), 9.1–9.2 (2H, m)

b) (1S,5R,6S)-2-[7-(1-Carbamoylmethylpyridinium-4-yl)(hydroxy)methylimidazo[5,1-b]thiazol-2-yl]-6-((1R)-1-hydroxyethyl)-1-methyl-1-carbapen-2-em-3-carboxylate (intramolecular salt) (a mixture of diastereomers)

A reaction was carried out in the same manner as in step b) of Example 1, except that 426 mg of 4-nitrobenzyl (1S,5R,6S)-2-[7-(1-carbamoylmethylpyridinium-4-yl)carbonylimidazo[5,1-b]thiazol-2-yl]-6-((1R)-1-hydroxyethyl)-1-methyl-1-carbapen-2-em-3-carboxylate iodide was used as the starting compound. The reaction product was subjected to column chromatography on Cosmosil $40C_{18}$-PREP (5%–20% aqueous methanol solution). The fraction, which had been eluted earlier, was collected to give 67.6 mg of the title compound.

NMR ($D_2O$) δ (HOD=4.80 ppm): 1.1–1.25 (3H, m), 1.29 (3H, d, J=6.3 Hz), 3.4–3.6 (2H, m), 4.2–4.3 (2H, m), 5.51 (2H, s), 6.28 (1H, s), 7.87 (1H, s), 8.09 (1H, s), 8.1–8.2 (2H, m), 8.75–8.85 (2H, m)

Example 9

(1S,5R,6S)-2-[7-(1-Carbamoylmethyl-pyridinium-4-yl)carbonylimidazo[5,1-b]thiazol-2-yl]-6-((1R)-1-hydroxyethyl)-1-methyl-1-carbapen-2-em-3-carboxylate (intramolecular salt) (Compound No. 9)

In the column chromatography on Cosmosil $40C_{18}$-PREP (5%–20% aqueous methanol solution) in step b) of Example 8, the fraction, which had been eluted later, was collected to give 29.1 mg of the title compound.

NMR (DMSO-$d_6$) δ: 1.1–1.25 (6H, m), 3.1–3.2 (1H, m), 3.45–3.6 (1H, m), 3.9–4.0 (1H, m), 4.05–4.15 (1H, m), 5.05 (1H, d, J=5.7 Hz), 5.5–5.7 (2H, m), 7.75 (1H, s), 8.33 (1H, s), 8.38 (1H, s), 8.41 (1H, s), 8.98 (2H, d, J=6.6 Hz), 9.26 (2H, d, J=6.6 Hz)

Example 10

Sodium (1S,5R,6S)-6-((1R)-1-hydroxyethyl)-1-methyl-2-[7-(4-methylthiazol-5-yl)carbonylimidazo[5,1-b]thiazol-2-yl]-1-carbapen-2-em-3-carboxylate (Compound No. 10)

a) 4-Nitrobenzyl (1S,5R,6S)-6-((1R)-1-hydroxyethyl)-1-methyl-2-[7-(4-methylthiazol-5-yl)carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[7-(4-methylthiazol-5-yl)carbonylimidazo[5,1-b]thiazol-2-yl]-1-carbapen-2-em-3-carboxylate (92 mg) was prepared in the same manner as in step a) of Example 1, except that 112 mg of 4-nitrobenzyl (1R,3R,5R,6S)-6-((1R)-1-hydroxyethyl)-1-methyl-2-oxo-1-carbapenam-3-carboxylate and 165 mg of 7-(4-methylthiazol-5-yl)carbonyl-2-(tri-n-butylstannyl)imidazo[5,1-b]thiazole were used as the starting compounds.

NMR (DMSO-$d_6$) δ: 1.18 (3H, d, J=6.3 Hz), 1.23 (3H, d, J=7.3 Hz), 2.78 (3H, s), 3.43 (1H, dd, $J_1$=6.1 Hz, $J_2$=2.8 Hz), 3.76 (1H, m), 4.03 (1H, m), 4.35 (1H, dd, $J_1$=10 Hz, $J_2$=3.0 Hz), 5.15 (1H, d, J=5.1 Hz), 5.40 (1H, d, J=13.9 Hz), 5.53 (1H, d, J=13.9 Hz), 7.73 (2H, d, J=8.8 Hz), 8.21 (2H, d, J=8.8 Hz), 8.43 (1H, s), 8.60 (1H, s), 9.22 (1H, s)

b) Sodium (1S,5R,6S)-6-((1R)-1-hydroxyethyl)-1-methyl-2-[7-(4-methylthiazol-5-yl)carbonylimidazo[5,1-b]thiazol-2-yl]-1-carbapen-2-em-3-carboxylate The title compound (21 mg) was prepared in the same manner as in step b) of Example 1, except that 57 mg of 4-nitrobenzyl (1S,5R,6S)-6-((1R)-1-hydroxyethyl)-1-methyl-2-[7-(4-methylthiazol-5-yl)carbonylimidazo[5,1-b]thiazol-2-yl]-1-carbapen-2-em-3-carboxylate was used as the starting compound.

NMR ($D_2O$) δ (HOD=4.65 ppm): 1.05 (3H, d, J=7.3 Hz), 1.22 (3H, d, J=6.3 Hz), 2.49 (3H, s), 3.36 (1H, m), 3.42 (1H, m), 4.13–4.22 (2H, m), 7.77 (1H, s), 7.88 (1H, s), 8.71 (1H, s)

Example 11

Sodium (1S,5R,6S)-6-((1R)-1-hydroxyethyl)-1-methyl-2-[7-((2S)-pyrrolidin-2-yl)carbonylimidazo[5,1-b]thiazol-2-yl]-1-carbapen-2-em-3-carboxylate (Compound No. 11)

a) 4-Nitrobenzyl (1S,5R,6S)-6-((1R)-1-hydroxyethyl)-1-methyl-2-[7-[(2S)-1-(4-nitrobenzyloxycarbonyl)-pyrrolidin-2-yl]carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[7-[(2S)-1-(4-nitrobenzyloxycarbonyl)-pyrrolidin-2-yl]carbonylimidazo[5,1-b]thiazol-2-yl]-1-carbapen-2-em-3-carboxylate (1.40 g) was prepared in the same manner as in step a) of Example 1, except that 926 mg of 4-nitrobenzyl (1R,3R,5R,6S)-6-((1R)-1-hydroxyethyl)-1-methyl-2-oxo-1-carbapenam-3-carboxylate and 1.85 g of 7-[(2S)-1-(4-nitrobenzyloxycarbonyl)-pyrrolidin-2-yl]carbonyl-2-(tri-n-butylstannyl)imidazo[5,1-b]thiazole were used as the starting compounds.

NMR ($CDCl_3$) δ: 1.25–1.35 (3H, m), 1.35–1.45 (3H, m), 1.85–2.5 (4H, m), 3.35–3.8 (4H, m), 4.25–4.5 (2H, m), 4.8–5.6 (5H, m), 7.2–8.3 (9H, m), 8.50 (1H, s)

b) Sodium (1S,5R,6S)-6-((1R)-1-hydroxyethyl)-1-methyl-2-[7-((2S)-pyrrolidin-2-yl)carbonylimidazo[5,1-b]thiazol-2-yl]-1-carbapen-2-em-3-carboxylate The title compound (169 mg) was prepared in the same manner as in step b) of Example 1, except that 451 mg of 4-nitrobenzyl (1S,5R,6S)-6-((1R)-1-hydroxyethyl)-1-methyl-2-[7-[(2S)-1-(4-nitrobenzyloxycarbonyl)-pyrrolidin-2-yl]carbonylimidazo[5,1-b]thiazol-2-yl]-1-carbapen-2-em-3-carboxylate was used as the starting compound.

NMR ($D_2O$) δ (HOD=4.80 ppm): 1.24 (3H, d, J=6.9 Hz), 1.35 (3H, d, J=6.3 Hz), 2.5–2.2 (3H, m), 2.6–2.75 (1H, m), 3.4–3.65 (4H, m), 4.2–4.4 (2H, m), 5.05–5.2 (1H, m), 8.05 (1H, s), 8.17 (1H, s)

Example 12

Sodium (1S,5R,6S)-6-((1R)-1-hydroxyethyl)-1-methyl-2-[7-(pyrimidin-5-yl)carbonylimidazo[5,1-b]thiazol-2-yl]-1-carbapen-2-em-3-carboxylate (Compound No. 12)

a) 4-Nitrobenzyl (1S,5R,6S)-6-((1R)-1-hydroxyethyl)-1-methyl-2-[7-(pyrimidin-5-yl)carbonylimidazo[5,1-b]-thiazol-2-yl]-1-carbapen-2-em-3-carboxylate 4-Nitrobenzyl (1S,5R,6S)-6-((1R)-1-hydroxyethyl)-1-methyl-2-[7-(pyrimidin-5-yl)carbonylimidazo[5,1-b]-thiazol-2-yl]-1-carbapen-2-em-3-carboxylate (144 mg) was prepared in substantially the same manner as in step a) of Example 1, except that 180 mg of 4-nitrobenzyl (1R,3R,5R,6S)-6-((1R)-1-hydroxyethyl)-1-methyl-2-oxo-1-carbapenam-3-carboxylate and 176 mg of 7-(pyrimidin-5-yl)carbonyl-2-(tri-n-butylstannyl)imidazo[5,1-b]thiazole were used as the starting compounds.

NMR ($CDCl_3$) δ: 1.34 (3H, d, J=7.3 Hz), 1.41 (3H, d, J=6.3 Hz), 3.41 (1H, dd, $J_1$=6.4 Hz, $J_2$=2.9 Hz), 3.56 (1H, m), 4.34 (1H, m), 4.43 (1H, dd, $J_1$=9.8 Hz, $J_2$=2.9 Hz), 5.30 (1H, d, J=13.6 Hz), 5.53 (1H, d, J=13.6 Hz), 7.69 (2H, d, J=9.0 Hz), 8.10 (1H, d), 8.20 (2H, d, J=9.0 Hz), 8.58 (1H, s), 9.37 (1H, s), 9.81 (2H, s)

b) Sodium (1S,5R,6S)-6-((1R)-1-hydroxyethyl)-1-methyl-2-[7-(pyrimidin-5-yl)carbonylimidazo[5,1-b]thiazol-2-yl]-1-carbapen-2-em-3-carboxylate The title compound (6.9 mg) was prepared in substantially the same manner as in step b) of Example 1, except that 57.4 mg of 4-nitrobenzyl (1S,5R,6S)-6-((1R)-1-hydroxyethyl)-1-methyl-2-[7-(pyrimidin-5-yl)carbonylimidazo[5,1-b]thiazol-2-yl]-1-carbapen-2-em-3-carboxylate was used as the starting compound.

NMR (DMSO-$d_6$) δ: 1.11 (3H, d, J=5.9 Hz), 1.13 (3H, d, J=6.6 Hz), 3.24 (1H, m), 3.56 (1H, m), 3.92 (1H, m), 4.15 (1H, dd, $J_1$=9.8 Hz, $J_2$=2.9 Hz), 5.02 (1H, br s), 8.37 (1H, s), 8.44 (1H, s), 9.31 (1H, s), 9.56 (2H, s); MS (m/z) 440 (M+H)$^+$

Example 13

Sodium (1S,5R,6S)-6-((1R)-1-hydroxyethyl)-1-methyl-2-[7-(thiophen-2-yl)carbonylimidazo[5,1-b]thiazol-2-yl]-1-carbapen-2-em-3-carboxylate (Compound No. 13)

a) 4-Nitrobenzyl (1S,5R,6S)-6-((1R)-1-hydroxyethyl)-1-methyl-2-[7-(thiophen-2-yl)carbonylimidazo[5,1-b]-thiazol-2-yl]-1-carbapen-2-em-3-carboxylate 4-Nitrobenzyl (1S,5R,6S)-6-((1R)-1-hydroxyethyl)-1-methyl-2-[7-(thiophen-2-yl)carbonylimidazo[5,1-b]-thiazol-2-yl]-1-carbapen-2-em-3-carboxylate (815 mg) was prepared in the same manner as in step a) of Example 1, except that 640 mg of 4-nitrobenzyl (1R,3R,5R,6S)-6-((1R)-1-hydroxyethyl)-1-methyl-2-oxo-1-carbapenam-3-carboxylate and 923 mg of 7-(thiophen-2-yl)carbonyl-2-(tri-n-butylstannyl)imidazo[5,1-b]thiazole were used as the starting compounds.

NMR (DMSO-$d_6$) δ: 1.18 (3H, d, J=6.3 Hz), 1.23 (3H, d, J=7.3 Hz), 3.43 (1H, dd, $J_1$=6.1 Hz, $J_2$=3 Hz), 3.75 (1H, m), 4.03 (1H, m), 4.35 (1H, dd, $J_1$=10 Hz, $J_2$=2.9 Hz), 5.13 (1H, d, J=5.1 Hz), 5.40 (1H, d, J=13.9 Hz), 5.53 (1H, d, J=13.9 Hz), 7.28 (1H, m), 7.77 (2H, d, J=8.8 Hz), 8.00 (1H, m), 8.21 (2H, d, J=8.8 Hz), 8.44 (1H, s), 8.60 (1H, m)

b) Sodium (1S,5R,6S)-6-((1R)-1-hydroxyethyl)-1-methyl-2-[7-(thiophen-2-yl)carbonylimidazo[5,1-b]thiazol-2-yl]-1-carbapen-2-em-3-carboxylate The title compound (95 mg) was prepared in the same manner as in step b) of Example 1, except that 170 mg of 4-nitrobenzyl (1S,5R,6S)-6-((1R)-1-hydroxyethyl)-1-methyl-2-[7-(thiophen-2-yl)carbonylimidazo[5,1-b]-thiazol-2-yl]-1-carbapen-2-em-3-carboxylate was used as the starting compound.

NMR ($D_2O$) δ (HOD=4.65 ppm): 1.01 (3H, d, J=7.3 Hz), 1.21 (3H, d, J=6.3 Hz), 3.27–3.36 (2H, m), 4.06–4.18 (2H, m), 6.93 (1H, m), 7.60 (1H, m), 7.68 (1H, s), 7.74 (1H, s), 7.87 (1H, m)

Example 14

Sodium (1S,5R,6S)-6-((1R)-1-hydroxyethyl)-2-[7-[5-(hydroxymethyl)pyridin-3-yl]carbonylimidazo[5,1-b]thiazol-2-yl]-1-methyl-1-carbapen-2-em-3-carboxylate (Compound No. 14)

a) 4-Nitrobenzyl (1S,5R,6S)-2-[7-[5-(t-butyldimethylsilyloxymethyl)pyridin-3-yl]carbonylimidazo

[5,1-b]-thiazol-2-yl]-6-((1R)-1-hydroxyethyl)-1-methyl-1-carbapen-2-em-3-carboxylate 4-Nitrobenzyl (1S,5R,6S)-2-[7-[5-(t-butyldimethylsilyloxymethyl)pyridin-3-yl]carbonylimidazo[5,1-b]-thiazol-2-yl]-6-((1R)-1-hydroxyethyl)-1-methyl-1-carbapen-2-em-3-carboxylate (707 mg) was prepared in the same manner as in step a) of Example 1, except that 509 mg of 4-nitrobenzyl (1R,3R,5R,6S)-6-((1R)-1-hydroxyethyl)-1-methyl-2-oxo-1-carbapenam-3-carboxylate and 926 mg of 7-[5-(t-butyldimethylsilyloxymethyl)pyridin-3-yl]carbonyl-2-(tri-n-butylstannyl)imidazo[5,1-b]thiazole were used as the starting compounds.

NMR (CDCl$_3$) δ: 0.01 (6H, s), 0.81 (9H, s), 1.19 (3H, d, J=7.3 Hz), 1.27 (3H, d, J=6.1 Hz), 3.26 (1H, dd, J$_1$=6.6 Hz, J$_2$=2.9 Hz), 3.42 (1H, m), 4.19 (1H, m), 4.29 (1H, dd, J$_1$=9.7 Hz, J$_2$=2.9 Hz), 4.73 (2H, s), 5.15 (1H, d, J=13.6 Hz), 5.39 (1H, d, J=13.6 Hz), 7.55 (2H, d, J=8.8 Hz), 7.94 (1H, s), 8.11 (2H, d, J=8.8 Hz), 8.43 (1H, S), 8.61 (1H, m), 8.66 (1H, m), 9.49 (1H, m)

b) 4-Nitrobenzyl (1S,5R,6S)-6-((1R)-1-hydroxyethyl)-2-[7-[5-(hydroxymethyl)pyridin-3-yl]carbonylimidazo[5,1-b] thiazol-2-yl]-1-methyl-1-carbapen-2-em-3-carboxylate Under ice cooling, 0.092 ml of acetic acid and 0.799 ml of a 1 M tetra-n-butylammonium fluoride/THF solution were added to a solution of 563 mg of 4-nitrobenzyl (1S,5R,6S)-2-[7-[5-(t-butyldimethylsilyloxymethyl)pyridin-3-yl]carbonylimidazo[5,1-b]thiazol-2-yl]-6-((1R)-1-hydroxyethyl)-1-methyl-1-carbapen-2-em-3-carboxylate in 8 ml of THF, and the mixture was stirred for 6 hr. Water was added to the reaction solution, and the mixture was extracted with ethyl acetate, followed by washing with brine. The organic layer was dried over anhydrous magnesium sulfate, and the solvent was then removed by distillation. The residue was purified by column chromatography (dichloromethane:methanol=1:1) on Sephadex LH-20 to give 435 mg of 4-nitrobenzyl (1S,5R,6S)-6-((1R)-1-hydroxyethyl)-2-[7-[5-(hydroxymethyl)pyridin-3-yl]carbonylimidazo[5,1-b]thiazol-2-yl]-1-methyl-1-carbapen-2-em-3-carboxylate.

NMR (DMSO-d$_6$) δ: 1.18 (3H, d, j=6.3 Hz), 1.23 (3H, d, J=7.1 Hz), 3.45 (1H, m), 3.77 (1H, m), 4.03 (1H, m), 4.36 (1H, m), 4.64 (2H, d, J=5.9 Hz), 5.15 (1H, d, J=5.1 Hz), 5.40 (1H, d, J=13.9 Hz), 5.46 (1H, t, J=5.9 Hz), 5.54 (1H, d, J=13.9 Hz), 7.73 (2H, d, J=8.8 Hz), 8.21 (2H, d, J=8.8 Hz), 8.47 (1H, s), 8.63 (1H, s), 8.66 (1H, m), 8.71 (1H, m), 9.47 (1H, m)

c) Sodium (1S,5R,6S)-6-((1R)-1-hydroxyethyl)-2-[7-[5-(hydroxymethyl)pyridin-3-yl]carbonylimidazo[5,1-b]-thiazol-2-yl]-1-methyl-1-carbapen-2-em-3-carboxylate The title compound (15 mg) was prepared in the same manner as in step b) of Example 1, except that 48 mg of 4-nitrobenzyl (1S,5R,6S)-6-((1R)-1-hydroxyethyl)-2-[7-[5-(hydroxymethyl)pyridin-3-yl]carbonylimidazo[5,1-b]-thiazol-2-yl]-1-methyl-1-carbapen-2-em-3-carboxylate was used as the starting compound.

NMR (D$_2$O) δ (HOD=4.65 ppm): 1.06 (3H, d, J=7.0 Hz), 1.20 (3H, d, J=6.3 Hz), 3.38 (1H, m), 3.47 (1H, m), 4.13–4.21 (2H, m), 7.86 (1H, s), 8.03 (1H, s), 8.17 (1H, s), 8.42 (1H, s), 8.78 (1H, s)

Example 15

Sodium (1S,5R,6S)-6-((1R)-1-hydroxyethyl)-1-methyl-2-[7-(6-methylpyridin-3-yl)carbonylimidazo[5,1-b]thiazol-2-yl]-1-carbapen-2-em-3-carboxylate (Compound No. 15)

a) 4-Nitrobenzyl (1S,5R,6S)-6-((1R)-1-hydroxyethyl)-1-methyl-2-[7-(6-methylpyridin-3-yl)carbonylimidazo[5,1-b] thiazol-2-yl]-1-carbapen-2-em-3-carboxylate 4-Nitrobenzyl (1S,5R,6S)-6-((1R)-1-hydroxyethyl)-1-methyl-2-[7-(6-methylpyridin-3-yl)carbonylimidazo[5,1-b] thiazol-2-yl]-1-carbapen-2-em-3-carboxylate (499 mg) was prepared in the same manner as in step a) of Example 1, except that 398 mg of 4-nitrobenzyl (1R,3R,5R,6S)-6-((1R)-1-hydroxyethyl)-1-methyl-2-oxo-1-carbapenam-3-carboxylate and 923 mg of 7-(6-methylpyridin-3-yl)carbonyl-2-(tri-n-butylstannyl)imidazo[5,1-b]thiazole were used as the starting compounds.

NMR (DMSO-d$_6$) δ: 1.18 (3H, d, J=6.4 Hz), 1.23 (3H, d, J=7.3 Hz), 2.57 (3H, s), 3.44 (1H, dd, J$_1$=6.0 Hz, J$_2$=2.9 Hz), 3.76 (1H, m), 4.03 (1H, m), 4.35 (1H, dd, J$_1$=10 Hz, J$_2$=2.7 Hz), 5.15 (1H, d, J=5.2 Hz), 5.40 (1H, d, J=13.7 Hz), 5.53 (1H, d, J=13.7 Hz), 7.44 (1H, m), 7.73 (2H, d, J=8.8 Hz), 8.20 (2H, d, J=8.8 Hz), 8.45 (1H, s), 8.61 (1H, s), 8.63 (1H, m), 9.48 (1H, m)

b) Sodium (1S,5R,6S)-6-((1R)-1-hydroxyethyl)-1-methyl-2-[7-(6-methylpyridin-3-yl)carbonylimidazo[5,1-b]thiazol 2-yl]-1-carbapen-2-em-3-carboxylate The title compound (23 mg) was prepared in the same manner as in step b) of Example 1, except that 75 mg of 4-nitrobenzyl (1S,5R,6S)-6-((1R)-1-hydroxyethyl)-1-methyl-2-[7-(6-methylpyridin-3-yl)carbonylimidazo[5,1-b] thiazol-2-yl]-1-carbapen-2-em-3-carboxylate was used as the starting compound.

NMR (D$_2$O) δ (HOD=4.65 ppm): 1.04 (3H, d, J=7.1 Hz), 1.21 (3H, d, J=6.1 Hz), 2.37 (3H, s), 3.37 (1H, m), 3.45 (1H, m), 4.14–4.21 (2H, m), 7.13 (1H, m), 7.82 (1H, s), 8.00 (1H, s), 8.08 (1H, m), 8.68 (1H, s)

Example 16

Sodium (1S,5R,6S)-6-((1R)-1-hydroxyethyl)-1-methyl-2-[7-(5-methylthiopyridin-3-yl) carbonylimidazo-[5,1-b]thiazol-2-yl]-1-carbapen-2-em-3-carboxylate (Compound No. 16)

a) 4-Nitrobenzyl (1S,5R,6S)-6-((1R)-1-hydroxyethyl)-1-methyl-2-[7-(5-methylthiopyridin-3-yl)carbonylimidazo-[5,1-b]thiazol-2-yl]-1-carbapen-2-em-3-carboxylate 4-Nitrobenzyl (1S,5R,6S)-6-((1R)-1-hydroxyethyl)-1-methyl-2-[7-(5-methylthiopyridin-3-yl)carbonylimidazo[5,1-b]thiazol-2-yl]-1-carbapen-2-em-3-carboxylate (100 mg) was prepared in substantially the same manner as in step a) of Example 1, except that 169 mg of 4-nitrobenzyl (1R,3R,5R,6S)-6-((1R)-1-hydroxyethyl)-1-methyl-2-oxo-1-carbapenam-3-carboxylate and 179 mg of 7-(5-methylthiopyridin-3-yl)carbonyl-2-(tri-n-butylstannyl) imidazo[5,1-b]thiazole were used as the starting compounds.

NMR (CDCl$_3$) δ: 1.15 (3H, d, J=7.3 Hz), 1.22 (3H, d, J=7.1 Hz), 2.60 (3H, s), 3.44 (1H, m), 3.76 (1H, m), 4.01 (1H, m), 4.35 (1H, dd, J$_1$=6.9 Hz, J$_2$=3.2 Hz), 5.15 (1H, d, J=5.2 Hz), 5.40 (1H, d, J=13.7 Hz), 5.52 (1H, d, J=13.7 Hz), 7.72 (2H, d, J=9.0 Hz), 8.20 (2H, d, J=9.0 Hz), 8.30 (1H, s), 8.47 (1H, s), 8.57 (1H, s), 8.68 (1H, s), 9.30 (1H, s)

b) Sodium (1S,5R,6S)-6-((1R)-1-hydroxyethyl)-1-methyl-2-[7-(5-methylthiopyridin-3-yl)carbonylimidazo[5,1-b] thiazol-2-yl]-1-carbapen-2-em-3-carboxylate The title compound (11.6 mg) was prepared in substantially the same manner as in step b) of Example 1, except that 93 mg of 4-nitrobenzyl (1S,5R,6S)-6-((1R)-1-hydroxyethyl)-1-methyl-2-[7-(5-methylthiopyridin-3-yl) carbonylimidazo[5,1-b]thiazol-2-yl]-1-carbapen-2-em-3-carboxylate was used as the starting compound.

NMR (DMSO-d$_6$) δ: 1.15 (3H, d, J=7.1 Hz), 1.18 (3H, d, J=6.3 Hz), 2.60 (3H, s), 3.15 (1H, m), 3.44 (1H, m), 3.95 (1H, m), 4.07 (1H, dd, J$_1$=6.7 Hz, J$_2$=2.7 Hz), 5.01 (1H, d, J=5.4 Hz), 8.29 (1H, s), 8.32 (1H, s), 8.56 (1H, s), 8.65 (1H, s), 9.28 (1H, s); MS (m/z) 507 (M+Na+H)$^+$

Example 17

Sodium (1S,5R,6S)-6-((1R)-1-hydroxyethyl)-1-methyl-2-[7-(quinolin-3-yl)carbonylimidazo[5,1-b]thiazol-2-yl]-1-carbapen-2-em-3-carboxylate
(Compound No. 17)

a) 4-Nitrobenzyl (1S,5R,6S)-6-((1R)-1-hydroxyethyl)-1-methyl-2-[7-(quinolin-3-yl)carbonylimidazo[5,1-b]-thiazol-2-yl]-1-carbapen-2-em-3-carboxylate 4-Nitrobenzyl (1S,5R,6S)-6-((1R)-1-hydroxyethyl)-1-methyl-2-[7-(quinolin-3-yl)carbonylimidazo[5,1-b]-thiazol-2-yl]-1-carbapen-2-em-3-carboxylate (86 mg) was prepared in substantially the same manner as in step a) of Example 1, except that 180 mg of 4-nitrobenzyl (1R,3R,5R,6S)-6-((1R)-1-hydroxyethyl)-1-methyl-2-oxo-1-carbapenam-3-carboxylate and 185 mg of 7-(quinolin-3-yl)carbonyl-2-(tri-n-butylstannyl)imidazo[5,1-b]thiazole were used as the starting compounds.

NMR (CDCl$_3$) δ: 1.12 (3H, d, J=6.3 Hz), 1.19 (3H, d, J=7.1 Hz), 3.41 (1H, dd, J$_1$=6.6 Hz, J$_2$=2.9 Hz), 3.58 (1H, m), 4.35 (1H, m), 4.43 (1H, dd, J$_1$=9.6 Hz, J$_2$=3.0 Hz), 5.30 (1H, d, J=13.6 Hz), 5.54 (1H, d, J=13.6 Hz), 7.63 (1H, t, J=7.1 Hz), 7.70 (2H, d, J=9.0 Hz), 7.83 (1H, t, J=7.2 Hz), 8.04 (1H, d, J=7.3 Hz), 8.14 (1H, s), 8.18 (1H, d, J=8.3 Hz), 8.24 (2H, d, J=8.9 Hz), 8.61 (1H, s), 9.63 (1H, s), 9.84 (1H, s)

b) Sodium (1S,5R,6S)-6-((1R)-1-hydroxyethyl)-1-methyl-2-[7-(quinolin-3-yl)carbonylimidazo[5,1-b]thiazol-2-yl]-1-carbapen-2-em-3-carboxylate The title compound (6.5 mg) was prepared in substantially the same manner as in step b) of Example 1, except that 84 mg of 4-nitrobenzyl (1S,5R,6S)-6-((1R)-1-hydroxyethyl)-1-methyl-2-[7-(quinolin-3-yl)carbonylimidazo[5,1-b]thiazol-2-yl]-1-carbapen-2-em-3-carboxylate was used as the starting compound.

NMR (DMSO-d$_6$) δ: 1.09 (3H, d, J=7.3 Hz), 1.11 (3H, d, J=6.4 Hz), 3.14 (1H, m), 3.47 (1H, m), 3.95 (1H, m), 4.09 (1H, dd, J$_1$=9.8 Hz, J$_2$=2.9 Hz), 5.02 (1H, br s), 7.71 (1H, t, J=6.8 Hz), 7.90 (1H, t, J=8.5 Hz), 8.11 (1H, d, J=9.0 Hz), 8.21 (1H, d, J=7.8 Hz), 8.31 (1H, s), 8.37 (1H, s), 9.47 (1H, s), 9.73 (1H, s); MS (m/z) 511 (M+Na+H)$^+$

Example 18

(1S,5R,6S)-2-[7-(1-Carbamoylmethyl-6-methylpyridinium-3-yl)carbonylimidazo[5,1-b]thiazol-2-yl]-6-((1R)-1-hydroxyethyl)-1-methyl-1-carbapen-2-em-3-carboxylate (intramolecular salt)
(Compound No. 18)

a) 4-Nitrobenzyl (1S,5R,6S)-2-[7-(1-carbamoylmethyl-6-methylpyridinium-3-yl)carbonylimidazo[5,1-b]thiazol-2-yl]-6-((1R)-1-hydroxyethyl)-1-methyl-1-carbapen-2-em-3-carboxylate Iodide A crude product (119 mg) of 4-nitrobenzyl (1S,5R,6S)-2-[7-(1-carbamoylmethyl-6-methylpyridinium-3-yl)carbonylimidazo[5,1-b]thiazol-2-yl]-6-((1R)-1-hydroxyethyl)-1-methyl-1-carbapen-2-em-3-carboxylate iodide was prepared in the same manner as in step a) of Example 2, except that 112 mg of 4-nitrobenzyl (1S,5R,6S)-6-((1R)-1-hydroxyethyl)-1-methyl-2-[7-(6-methylpyridin-3-yl)-carbonylimidazo[5,1-b]thiazol-2-yl]-1-carbapen-2-em-3-carboxylate and 495 mg of 2-iodoacetamide were used as the starting compounds.

b) (1S,5R,6S)-2-[7-(1-Carbamoylmethyl-6-methylpyridinium-3-yl)carbonylimidazo[5,1-b]thiazol-2-yl]-6-((1R)-1-hydroxyethyl)-1-methyl-1-carbapen-2-em-3-carboxylate (intramolecular salt)

The title compound (23 mg) was prepared in the same manner as in step b) of Example 1, except that 119 mg of the crude product of 4-nitrobenzyl (1S,5R,6S)-2-[7-(1-carbamoylmethyl-6-methylpyridinium-3-yl)carbonylimidazo[5,1-b]thiazol-2-yl]-6-((1R)-1-hydroxyethyl)-1-methyl-1-carbapen-2-em-3-carboxylate iodide was used as the starting compound.

NMR (D$_2$O) δ (HOD=4.65 ppm): 1.04 (3H, d, J=7.1 Hz), 1.21 (3H, d, J=6.1 Hz), 2.68 (3H, s), 3.23–3.35 (2H, m), 4.03 (1H, m), 4.13 (1H, m), 5.47 (2H, s), 7.69 (1H, s), 7.80–7.84 (2H, m), 8.84 (1H, m), 9.34 (1H, s)

Example 19

Sodium (1S,5R,6S)-6-((1R)-1-hydroxyethyl)-1-methyl-2-[7-([3,3']bipyridinyl-5-yl)carbonylimidazo[5,1-b]thiazol-2-yl]-1-carbapen-2-em-3-carboxylate
(Compound No. 19)

a) 4-Nitrobenzyl (1S,5R,6S)-6-((1R)-1-hydroxyethyl)-1-methyl-2-[7-([3,3']bipyridinyl-5-yl)carbonylimidazo[5,1-b]thiazol-2-yl]-1-carbapen-2-em-3-carboxylate 7-([3,3']Bipyridinyl-5-yl)carbonyl-2-(tri-n-butylstannyl)imidazo[5,1-b]thiazole was synthesized in substantially the same manner as in step c) of Synthesis Example 1, except that 263 mg of 7-([3,3']bipyridinyl-5-yl)carbonylimidazo[5,1-b]thiazole, 0.316 ml of tri-n-butylstannyl chloride, and 1.72 ml of a 1.0 N lithium bis(trimethylsilyl)amide/THF solution were used as the starting compounds and, due to the unstable nature of the tin compound, the purification by column chromatography on silica gel was not carried out. 4-Nitrobenzyl (1S,5R,6S)-6-((1R)-1-hydroxyethyl)-1-methyl-2-[7-([3,3']bipyridinyl-5-yl)carbonylimidazo[5,1-b]-thiazol-2-yl]-1-carbapen-2-em-3-carboxylate (80 mg) was prepared in substantially the same manner as in step a) of Example 1, except that 270 mg of 4-nitrobenzyl (1R,3R,5R,6S)-6-((1R)-1-hydroxyethyl)-1-methyl-2-oxo-1-carbapenam-3-carboxylate and 7-([3,3']bipyridinyl-5-yl)carbonyl-2-(tri-n-butylstannyl)imidazo[5,1-b]thiazole were used as the starting compounds.

NMR (CDCl$_3$) δ: 1.33 (3H, d, J=7.3 Hz), 1.37 (3H, d, J=6.3 Hz), 3.37 (1H, m), 3.64 (1H, m), 4.24 (1H, m), 4.41 (1H, dd, J$_1$=9.6 Hz, J$_2$=3.0 Hz), 5.32 (1H, d, J=13.6 Hz), 5.53 (1H, d, J=13.4 Hz), 7.52 (1H, m), 7.69 (2H, t, J=8.7 Hz), 8.06 (1H, m), 8.15 (1H, s), 8.24 (2H, d, J=8.7 Hz), 8.67 (1H, m), 8.92 (1H, s), 8.99 (1H, s), 9.07 (1H, s), 9.71 (1H, s)

b) Sodium (1S,5R,6S)-6-((1R)-1-hydroxyethyl)-1-methyl-2-[7-([3,3']bipyridinyl-5-yl)carbonylimidazo[5,1-b]-thiazol-2-yl]-1-carbapen-2-em-3-carboxylate The title compound (16.7 mg) was prepared in substantially the same manner as in step b) of Example 1, except that 47 mg of 4-nitrobenzyl (1S,5R,6S)-6-((1R)-1-hydroxyethyl)-1-methyl-2-[7-([3,3']bipyridinyl-5-yl)carbonylimidazo[5,1-b]thiazol-2-yl]-1-carbapen-2-em-3-carboxylate was used as the starting compound.

NMR (DMSO-d$_6$) δ: 1.18 (6H, d, J=7.3 Hz), 3.23 (1H, m), 3.57 (1H, m), 3.97 (1H, m), 4.15 (1H, m), 5.06 (1H, d, J=5.4 Hz), 7.46–7.57 (3H, m), 7.79 (1H, br s), 7.82 (1H, br s), 8.40 (1H, br s), 8.95 (1H, br s), 9.08 (1H, br s), 9.49 (1H, br s); MS (m/z) 538 (M+Na+H)$^+$

Example 20

Sodium (1S,5R,6S)-6-((1R)-1-hydroxyethyl)-1-methyl-2-[7-(5-phenylpyridin-3-yl)carbonylimidazo[5,1-b]thiazol-2-yl]-1-carbapen-2-em-3-carboxylate
(Compound No. 20)

a) 4-Nitrobenzyl (1S,5R,6S)-6-((1R)-1-hydroxyethyl)-1-methyl-2-[7-(5-phenylpyridin-3-yl)carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[7-(5-phenylpyridin-3-yl)carbonylimidazo[5,1-b]thiazol-2-yl]-1-carbapen-2-em-3-carboxylate (47 mg) was prepared in substantially the same manner as in step a) of Example 1, except that 270 mg of 4-nitrobenzyl (1R,3R,5R,6S)-6-((1R)-1-hydroxyethyl)-1-methyl-2-oxo-1-carbapenam-3-carboxylate and 293 mg of 7-(5-phenylpyridin-3-yl)carbonyl-2-(tri-n-butylstannyl)imidazo[5,1-b]thiazole were used as the starting compounds.

NMR (CDCl$_3$) δ: 1.33 (3H, d, J=7.3 Hz), 1.37 (3H, d, J=6.1 Hz), 3.38 (1H, m), 3.57 (1H, m), 4.23 (1H, m), 4.41 (1H, dd, J$_1$=9.6 Hz, J$_2$=2.9 Hz), 5.34 (1H, d, J=13.6 Hz), 5.53 (1H, d, J=13.4 Hz), 7.45–7.55 (3H, m), 7.68–7.73 (4H, m), 8.15 (1H, s), 8.24 (2H, d, J=9.2 Hz), 8.55 (1H, s), 8.97–9.02 (2H, m), 9.65 (1H, S)

b) Sodium (1S,5R,6S)-6-((1R)-1-hydroxyethyl)-1-methyl-2-[7-(5-phenylpyridin-3-yl)carbonylimidazo[5,1-b]thiazol-2-yl]-1-carbapen-2-em-3-carboxylate The title compound (29.7 mg) was prepared in substantially the same manner as in step b) of Example 1, except that 80 mg of 4-nitrobenzyl (1S,5R,6S)-6-((1R)-1-hydroxyethyl)-1-methyl-2-[7-(5-phenylpyridin-3-yl)carbonylimidazo[5,1-b]thiazol-2-yl]-1-carbapen-2-em-3-carboxylate was used as the starting compound.

NMR (DMSO-d$_6$) δ: 1.16 (3H, d, J=6.8 Hz), 1.19 (3H, d, J=6.4 Hz), 3.14 (1H, dd, J$_1$=6.8 Hz, J$_2$=2.8 Hz), 3.45 (1H, m), 3.96 (1H, m), 4.15 (1H, dd, J$_1$=9.4 Hz, J$_2$=2.4 Hz), 5.02 (1H, d, J=5.2 Hz), 7.46–7.58 (3H, m), 7.79–7.83 (2H, m), 8.31 (1H, s), 8.34 (1H, s), 8.94 (1H, br s), 9.07 (1H, d, J=2.0 Hz), 9.48 (1H, d, J=2.0 Hz); MS (m/z) 537 (M+Na+H)$^+$

Example 21

Sodium (1S,5R,6S)-6-((1R)-1-hydroxyethyl)-1-methyl-2-[7-(thiazol-5-yl)carbonylimidazo[5,1-b]thiazol-2-yl]-1-carbapen-2-em-3-carboxylate (Compound No. 21)

a) 4-Nitrobenzyl (1S,5R,6S)-6-((1R)-1-hydroxyethyl)-1-methyl-2-[7-(thiazol-5-yl)carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[7-(thiazol-5-yl)carbonylimidazo[5,1-b]thiazol-2-yl]-1-carbapen-2-em-3-carboxylate (244 mg) was prepared in the same manner as in step a) of Example 1, except that 179 mg of 4-nitrobenzyl (1R,3R,5R,6S)-6-((1R)-1-hydroxyethyl)-1-methyl-2-oxo-1-carbapenam-3-carboxylate and 260 mg of 7-(thiazol-5-yl)carbonyl-2-(tri-n-butylstannyl)imidazo[5,1-b]thiazole were used as the starting compounds.

NMR (DMSO-d$_6$) δ: 1.18 (3H, d, J=6.3 Hz), 1.23 (3H, d, J=7.3 Hz), 3.43 (1H, dd, J$_1$=6.0 Hz, J$_2$=3.0 Hz), 3.76 (1H, m), 4.03 (1H, m), 4.35 (1H, dd, J$_1$=10 Hz, J$_2$=2.9 Hz), 5.15 (1H, d, J=5.1 Hz), 5.39 (1H, d, J=13.6 Hz), 5.53 (1H, d, J=13.6 Hz), 7.73 (2H, d, J=8.8 Hz), 8.20 (2H, d, J=8.8 Hz), 8.48 (1H, s), 8.62 (1H, s), 9.12 (1H, s), 9.40 (1H, S)

b) Sodium (1S,5R,6S)-6-((1R)-1-hydroxyethyl)-1-methyl-2-[7-(thiazol-5-yl)carbonylimidazo[5,1-b]thiazol-2-yl]-1-carbapen-2-em-3-carboxylate The title compound (47 mg) was prepared in the same manner as in step b) of Example 1, except that 114 mg of 4-nitrobenzyl (1S,5R,6S)-6-((1R)-1-hydroxyethyl)-1-methyl-2-[7-(thiazol-5-yl)carbonylimidazo[5,1-b]thiazol-2-yl]-1-carbapen-2-em-3-carboxylate was used as the starting compound.

NMR (D$_2$O) δ (HOD=4.65 ppm): 1.06 (3H, d, J=7.3 Hz), 1.22 (3H, d, J=6.3 Hz), 3.37 (1H, dd, J$_1$=6.1 Hz, J$_2$=2.9 Hz), 3.43 (1H, m), 4.14–4.22 (2H, m), 7.77 (1H, s), 7.90 (1H, s), 8.45 (1H, s), 8.98 (1H, s)

Example 22

(1S,5R,6S)-2-[7-(1,6-Dimethylpyridinium-3-yl)carbonylimidazo[5,1-b]thiazol-2-yl]-6-((1R)-1-hydroxyethyl)-1-methyl-1-carbapen-2-em-3-carboxylate (intramolecular salt) (Compound No. 22)

a) 4-Nitrobenzyl (1S,5R,6S)-2-[7-(1,6-dimethylpyridinium-3-yl)carbonylimidazo[5,1-b]thiazol-2-yl]-6-((1R)-1-hydroxyethyl)-1-methyl-1-carbapen-2-em-3-carboxylate trifluoromethanesulfonate Under ice cooling, 92 mg of 4-nitrobenzyl (1S,5R,6S)-6-((1R)-1-hydroxyethyl)-1-methyl-2-[7-(6-methylpyridin-3-yl)carbonylimidazo[5,1-b]thiazol-2-yl]-1-carbapen-2-em-3-carboxylate was dissolved in 4 ml of dichloromethane to prepare a solution, and 0.018 ml of methyl trifluoromethanesulfonate was added to the solution. The mixture was stirred at that temperature for 30 min. The reaction solution was then concentrated under the reduced pressure to give 110 mg of 4-nitrobenzyl (1S,5R,6S)-2-[7-(1,6-dimethylpyridinium-3-yl)carbonylimidazo[5,1-b]thiazol-2-yl]-6-((1R)-1-hydroxyethyl)-1-methyl-1-carbapen-2-em-3-carboxylate trifluoromethanesulfonate.

NMR (DMSO-d$_6$) δ: 1.18 (3H, d, J=6.3 Hz), 1.23 (3H, d, J=7.1 Hz), 2.86 (3H, s), 3.45 (1H, m), 3.77 (1H, m), 4.03 (1H, m), 4.34 (3H, s), 4.38 (1H, m), 5.15 (1H, d, J=5.1 Hz), 5.40 (1H, d, J=13.6 Hz), 5.53 (1H, d, J=13.6 Hz), 7.73 (2H, d, J=8.8 Hz), 8.20 (2H, d, J=8.8 Hz), 8.54 (1H, S), 8.65 (1H, s), 9.33 (1H, m), 9.76 (1H, m)

b) (1S,5R,6S)-2-[7-(1,6-Dimethylpyridinium-3-yl)carbonylimidazo[5,1-b]thiazol-2-yl]-6-((1R)-1-hydroxyethyl)-1-methyl-1-carbapen-2-em-3-carboxylate (intramolecular salt)

The title compound (16 mg) was prepared in the same manner as in step b) of Example 1, except that 110 mg of 4-nitrobenzyl (1S,5R,6S)-2-[7-(1,6-dimethylpyridinium-3-yl)carbonylimidazo[5,1-b]thiazol-2-yl]-6-((1R)-1-hydroxyethyl)-1-methyl-1-carbapen-2-em-3-carboxylate trifluoromethanesulfonate was used as the starting compound.

NMR (D$_2$O) δ (HOD=4.65 ppm): 1.08 (3H, d, J=7.3 Hz), 1.20 (3H, d, J=6.1 Hz), 2.73 (3H, s), 3.30–3.40 (2H, m), 4.07–4.18 (2H, m), 4.22 (3H, s), 7.78 (1H, s), 7.80 (1H, s), 7.88 (1H, s), 8.77 (1H, m), 9.40 (1H, m)

Example 23

(1S,5R,6S)-6-((1R)-1-Hydroxyethyl)-2-[7-((2S,4R)-4-hydroxypyrrolidin-2-yl)carbonylimidazo[5,1-b]thiazol-2-yl]-1-methyl-1-carbapen-2-em-3-carboxylate (Compound No. 23)

a) 4-Nitrobenzyl (1S,5R,6S)-2-[7-[(2S,4R)-4-t-butyldimethylsilyloxy-1-(4-nitrobenzyloxycarbonyl)pyrrolidin-2-yl]carbonylimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[7-[(2S,4R)-4-t-butyldimethylsilyloxy-1-(4-nitrobenzyloxycarbonyl)pyrrolidin-2-yl]carbonylimidazo[5,1-b]thiazol-2-yl]-6-((1R)-1-hydroxyethyl)-1-methyl-1-carbapen-2-em-3-carboxylate (369 mg) was prepared in the same manner as in step a) of Example 1, except that 312 mg of 4-nitrobenzyl (1R,3R,5R,6S)-6-((1R)-1-hydroxyethyl)-1-methyl-2-oxo-1-carbapenam-3-carboxylate and 707 mg of 7-[(2S,4R)-4-t-butyldimethylsilyloxy-1-(4-nitrobenzyloxycarbonyl)pyrrolidin-2-yl]carbonyl-2-(tri-n-butylstannyl)imidazo[5,1-b]thiazole were used as the starting compounds.

NMR (CDCl$_3$) δ: 0.07, 0.08 (total 6H, s each), 0.88, 0.89 (total 9H, s each), 1.25–1.35 (3H, m), 1.35–1.45 (3H, m), 2.1–2.2 (1H, m), 2.35–2.45 (1H, m), 3.35–3.6 (3H, m), 3.8–3.9 (1H, m), 4.25–4.6 (3H, m), 4.8–5.6 (5H, m), 7.2–8.3 (9H, m), 8.48, 8.50 (total 1H, s each)

b) 4-Nitrobenzyl (1S,5R,6S)-2-[7-[(2S,4R)-4-hydroxy-1-(4-nitrobenzyloxycarbonyl)pyrrolidin-2-yl]carbonylimidazo[5,1-b]thiazol-2-yl]-6-((1R)-1-hydroxyethyl)-1-methyl-1-carbapen-2-em-3-carboxylate Acetic acid (0.219 ml) and 1.27 ml of a 1 M tetra-n-butylammonium fluoride/THF solution were added to a solution of 369 mg of 4-nitrobenzyl (1S,5R,6S)-2-[7[(2S,4R)-4-t-butyldimethylsilyloxy-1-(4-nitrobenzyloxycarbonyl)pyrrolidin-2-yl]carbonylimidazo[5,1-b]thiazol-2-yl]-6-((1R)-1-hydroxyethyl)-1-methyl-1-carbapen-2-em-3-carboxylate in 10 ml of THF, and the mixture was stirred at room temperature for 7 hr. Brine was added to the reaction solution. The mixture was adjusted to pH 8.2 by the addition of a saturated sodium hydrogencarbonate solution and was then extracted twice with ethyl acetate. The organic layers were combined, and the combined organic layers were washed with brine and were dried over anhydrous magnesium sulfate. The solvent was then removed by distillation under the reduced pressure. The residue was purified by column chromatography on silica gel (dichloromethane:methanol=10:1) to give 239 mg of 4-nitrobenzyl (1S,5R,6S)-2-[7-[(2S,4R)-4-hydroxy-1-(4-nitrobenzyloxycarbonyl)pyrrolidin-2-yl]carbonylimidazo[5,1-b]thiazol-2-yl]-6-((1R)-1-hydroxyethyl)-1-methyl-1-carbapen-2-em-3-carboxylate.

NMR (CDCl$_3$) δ: 1.25–1.35 (3H, m), 1.35–1.45 (3H, m), 2.15–2.25 (1H, m), 2.45–2.55 (1H, m), 3.35–3.9 (4H, m), 4.3–4.65 (3H, m), 4.8–5.6 (5H, m), 7.2–8.3 (9H, m), 8.47, 8.50 (total 1H, s each)

c) (1S,5R,6S)-6-((1R)-1-Hydroxyethyl)-2-[7-((2S,4R)-4-hydroxypyrrolidin-2-yl)carbonylimidazo[5,1-b]thiazol-2-yl]-1-methyl-1-carbapen-2-em-3-carboxylate The title compound (76.3 mg) was prepared in the same manner as in step b) of Example 1, except that 239 mg of 4-nitrobenzyl (1S,5R,6S)-2-[7-[(2S,4R)-4-hydroxy-1-(4-nitrobenzyloxycarbonyl)pyrrolidin-2-yl]carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.80 ppm): 1.24 (3H, d, J=6.9 Hz), 1.32 (3H, d, J=6.3 Hz), 2.1–2.25 (1H, m), 2.65–2.75 (1H, m), 3.4–3.6 (4H, m), 4.2–4.35 (2H, m), 4.7–4.8 (1H, m), 5.2–5.3 (1H, m), 8.00 (1H, s), 8.08 (1H, s)

Example 24

(1S,5R,6S)-6-((1R)-1-Hydroxyethyl)-1-methyl-2-[7-(1-methylquinolinium-3-yl)carbonylimidazo[5,1-b]thiazol-2-yl]-1-carbapen-2-em-3-carboxylate (intramolecular salt) (Compound No. 24)

4-Nitrobenzyl (1S,5R,6S)-6-((1R)-1-hydroxyethyl)-1-methyl-2-[7-(quinolin-3-yl)carbonylimidazo[5,1-b]-thiazol-2-yl]-1-carbapen-2-em-3-carboxylate (93 mg) was dissolved in acetonitrile (2.25 ml)/chloroform (0.75 ml) to prepare a solution. Methyl iodide (0.063 ml) was added to the solution at room temperature, and the mixture was stirred at 40° C. for 3 days. The reaction solution was poured into diethyl ether to produce a powder which was filtered to give an N-quaternarized compound. The title compound (7.7 mg) was prepared in substantially the same manner as in step b) of Example 1, except that this compound was used as the starting compound.

NMR (DMSO-d$_6$) δ: 1.16 (3H, d, J=8.3 Hz), 1.18 (3H, d, J=6.4 Hz), 3.13 (1H, m), 3.49 (1H, m), 3.94 (1H, m), 4.09 (1H, dd, J$_1$=9.6 Hz, J$_2$=3.0 Hz), 4.75 (3H, s), 5.02 (1H, d, J=5.2 Hz), 8.13 (1H, t, J=7.6 Hz), 8.31 (1H, s), 8.39 (1H, m), 8.45 (1H, s), 8.58 (1H, d, J=9.0 Hz), 8.71 (1H, d, J=7.6 Hz), 10.15–10.28 (2H, m); MS (m/z) 503 (M+H)$^+$

Example 25

Sodium (1S,5R,6S)-6-((1R)-1-hydroxyethyl)-1-methyl-2-[7-[5-(morpholin-4-yl)methylpyridin-3-yl]-carbonylimidazo[5,1-b]thiazol-2-yl]-1-carbapen-2-em-3-carboxylate (Compound No. 25)

a) 4-Nitrobenzyl (1S,5R,6S)-6-((1R)-1-hydroxyethyl)-1-methyl-2-[7-[5-(morpholin-4-yl)methylpyridin-3-yl]-carbonylimidazo[5,1-b]thiazol-2-yl]-1-carbapen-2-em-3-carboxylate 7-[5-(Morpholin-4-yl)methylpyridin-3-yl]carbonylimidazo[5,1-b]thiazole (312 mg) was prepared in substantially the same manner as in step b) of Synthesis Example 1, except that 384 mg of 7-(hydroxy)[5-(morpholin-4-yl)methylpyridin-3-yl]methylimidazo[5,1-b]-thiazole and 200 mg of manganese dioxide were used as the starting compounds. A corresponding tin compound was synthesized in substantially the same manner as in step c) of Synthesis Example 1, except that 407 mg of this compound, 0.450 ml of tri-n-butylstannyl chloride, and 2.46 ml of a 1.0 N lithium bis(trimethylsilyl)amide/THF solution were used as the starting materials and, due to the unstable nature of the tin compound, the purification by column chromatography on silica gel was not carried out. 4-Nitrobenzyl (1S,5R,6S)-6-((1R)-1-hydroxyethyl)-1-methyl-2-[7-[5-(morpholin-4-yl)methylpyridin-3-yl]carbonylimidazo[5,1-b]thiazol-2-yl]-1-carbapen-2-em-3-carboxylate (250 mg) was prepared in substantially the same manner as in step a) of Example 1, except that 400 mg of 4-nitrobenzyl (1R,3R,5R,6S)-6-((1R)-1-hydroxyethyl)-1-methyl-2-oxo-1-carbapenam-3-carboxylate and the tin compound were used as the starting compounds.

NMR (CDCl$_3$) δ: 1.33 (3H, d, J=7.3 Hz), 1.41 (3H, d, J=6.1 Hz), 2.50 (4H, br s), 3.40 (1H, dd, J=6.6 Hz, 2.9 Hz), 3.56 (1H, m), 3.63 (2H, s), 3.72 (4H, t, J=4.6 Hz), 4.33 (1H, m), 4.43 (1H, dd, J$_1$=9.6 Hz, J$_2$=3.0 Hz), 5.29 (1H, d, J=13.6 Hz), 5.53 (1H, d, J=13.4 Hz), 7.69 (2H, d, J=9.0 Hz), 8.09 (1H, s), 8.24 (2H, d, J=8.8 Hz), 8.71 (1H, br s), 8.73 (1H, br s), 9.65 (1H, br s)

b) Sodium (1S,5R,6S)-6-((1R)-1-hydroxyethyl)-1-methyl-2-[7-[5-(morpholin-4-yl)methylpyridin-3-yl]carbonylimidazo[5,1-b]thiazol-2-yl]-1-carbapen-2-em-3-carboxylate The title compound (40.4 mg) was prepared in substantially the same manner as in step b) of Example 1, except that 101 mg of 4-nitrobenzyl (1S,5R,6S)-6-((1R)-1-hydroxyethyl)-1-methyl-2-[7-[5-(morpholin-4-yl)methylpyridin-3-yl]carbonylimidazo[5,1-b]thiazol-2-yl]-1-carbapen-2-em-3-carboxylate was used as the starting compound.

NMR (DMSO-d$_6$) δ: 1.15 (3H, d, J=6.8 Hz), 1.18 (3H, d, J=6.3 Hz), 2.40 (4H, br s), 3.14 (1H, dd, J$_1$=7.1 Hz, J$_2$=2.7 Hz), 3.43 (1H, m), 3.52 (4H, t, J=4.6 Hz), 3.54 (2H, s), 3.94 (1H, m), 4.08 (1H, dd, J$_1$=9.3 Hz, J$_2$=2.7 Hz), 5.02 (1H, d, J=5.1 Hz), 8.30 (1H, s), 8.33 (1H, s), 8.58 (1H, s), 8.67 (1H, s), 9.48 (1H, s); MS (m/z) 560 (M+Na+H)$^+$

Example 26

(1S,5R,6S)-6-((1R)-1-Hydroxyethyl)-1-methyl-2-[7-(1-methyl-5-phenylpyridinium-3-yl)carbonylimidazo[5,1-b]thiazol-2-yl]-1-carbapen-2-em-3-carboxylate (intramolecular salt) (Compound No. 26)

An N-quaternarized compound (84 mg) was prepared in substantially the same manner as in Example 24, except that 97 mg of 4-nitrobenzyl (1S,5R,6S)-6-((1R)-1-hydroxyethyl)-1-methyl-2-[7-(5-phenylpyridin-3-yl)carbonylimidazo[5,1-b]thiazol-2-yl]-1-carbapen-2-em-3-carboxylate and 0.063 ml of methyl iodide were used as the starting compounds. The title compound (20.3 mg) was prepared in substantially the same manner as in step c) of Example 1, except that this compound was used as the starting compound.

NMR (DMSO-$d_6$) δ: 1.15 (3H, d, J=7.1 Hz), 1.18 (3H, d, J=6.3 Hz), 3.13 (1H, m), 3.43 (1H, m), 3.94 (1H, m), 4.07 (1H, m), 4.46 (3H, s), 5.03 (1H, d, J=5.1 Hz), 7.59–7.68 (3H, m), 7.94 (2H, d, J=8.0 Hz), 8.29 (1H, br s), 8.40 (1H, br s), 9.57 (1H, br s), 9.70 (2H, br s); MS (m/z) 529 (M+H)$^+$

Example 27

(1S,5R,6S)-2-[7-(1-Carbamoylmethyl-5-phenylpyridinium-3-yl)carbonylimidazo[5,1-b]thiazol-2-yl]-6-((1R)-1-hydroxyethyl)-1-methyl-1-carbapen-2-em-3-carboxylate (intramolecular salt) (Compound No. 27)

An N-quaternarized compound (91 mg) was prepared in substantially the same manner as in Example 24, except that 97 mg of 4-nitrobenzyl (1S,5R,6S)-6-((1R)-1-hydroxyethyl)-1-methyl-2-[7-(5-phenylpyridin-3-yl)carbonylimidazo[5,1-b]thiazol-2-yl]-1-carbapen-2-em-3-carboxylate and 185 mg of 2-iodoacetamide were used as the starting compounds. The title compound (16.7 mg) was prepared in substantially the same manner as in step c) of Example 1, except that this compound was used as the starting compound.

NMR (DMSO-$d_6$) δ: 1.15 (3H, d, J=7.6 Hz), 1.19 (3H, d, J=6.2 Hz), 3.14 (1H, dd, $J_1$=7.2 Hz, $J_2$=2.4 Hz), 3.37 (1H, m), 3.94 (1H, m), 4.09 (1H, dd, $J_1$=8.6 Hz, $J_2$=2.7 Hz), 5.02 (1H, d, J=5.2 Hz), 5.58 (2H, s), 7.62–7.69 (3H, m), 7.92 (2H, d, J=7.6 Hz), 8.31 (1H, s), 8.40 (1H, s), 9.57 (1H, br s), 9.69 (1H, br s), 9.82 (1H, br s); MS (m/z) 572 (M+H)$^+$

Example 28

Sodium (1S,5R,6S)-2-[7-[5-(2-aminoethylthio)pyridin-3-yl]carbonylimidazo[5,1-b]-thiazol-2-yl]-6-((1R)-1-hydroxyethyl)-1-methyl-1-carbapen-2-em-3-carboxylate (Compound No. 28)

a) 4-Nitrobenzyl (1S,5R,6S)-2-[7-[5-(2-azidoethylthio)pyridin-3-yl]carbonylimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[7-[5-(2-azidoethylthio)pyridin-3-yl]carbonylimidazo[5,1-b]thiazol-2-yl]-6-((1R)-1-hydroxyethyl)-1-methyl-1-carbapen-2-em-3-carboxylate (370 mg) was prepared in the same manner as in step a) of Example 1, except that 485 mg of 4-nitrobenzyl (1R,3R,5R,6S)-6-((1R)-1-hydroxyethyl)-1-methyl-2-oxo-1-carbapenam-3-carboxylate and 857 mg of 7-[5-(2-azidoethylthio)pyridin-3-yl]carbonyl-2-(tri-n-butylstannyl)imidazo[5,1-b]thiazole were used as the starting compounds.

NMR (CDCl$_3$) δ: 1.34 (3H, d, J=7.3 Hz), 1.42 (3H, d, J=6.4 Hz), 3.19 (2H, t, J=7.0 Hz), 3.41 (1H, dd, $J_1$=6.0 Hz, $J_2$=3.0 Hz), 3.52–3.60 (3H, m), 4.33 (1H, m), 4.43 (1H, dd, $J_1$=9.7 Hz, $J_2$=2.9 Hz), 5.30 (1H, d, J=13.6 Hz), 5.54 (1H, d, J=13.6 Hz), 7.69 (2H, d, J=8.8 Hz), 8.09 (1H, s), 8.25 (2H, d, J=8.8 Hz), 8.56 (1H, s), 8.78 (1H, m), 8.90 (1H, m), 9.56 (1H, m)

b) Sodium (1S,5R,6S)-2-[7-[5-(2-aminoethylthio)pyridin-3-yl]carbonylimidazo[5,1-b]thiazol-2-yl]-6-((1R)-1-hydroxyethyl)-1-methyl-1-carbapen-2-em-3-carboxylate The title compound (40 mg) was prepared in the same manner as in step b) of Example 1, except that 128 mg of 4-nitrobenzyl (1S,5R,6S)-2-[7-[5-(2-azidoethylthio)pyridin-3-yl]carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.65 ppm): 1.01 (3H, d, J=7.0 Hz), 1.19 (3H, d, J=6.4 Hz), 3.18 (4H, m), 3.30–3.37 (2H, m), 4.06–4.16 (2H, m), 7.67 (1H, s), 7.80 (1H, s), 8.04 (1H, s), 8.21 (1H, s), 8.50 (1H, s)

Example 29

(1S,5R,6S)-2-[7-((2S,4S)-4-Aminopyrrolidin-2-yl)carbonylimidazo[5,1-b]thiazol-2-yl]-6-((1R)-1-hydroxyethyl)-1-methyl-1-carbapen-2-em-3-carboxylate (Compound No. 29)

a) 4-Nitrobenzyl (1S,5R,6S)-2-[7-[(2S,4S)-4-azido-1-(4-nitrobenzyloxycarbonyl)pyrrolidin-2-yl]carbonylimidazo[5,1-b]thiazol-2-yl]-6-((1R)-1-hydroxyethyl)-1-methyl-1-carbapen-2-em-3-carboxylate A crude compound (261 mg) of 4-nitrobenzyl (1S,5R,6S)-2-[7-[(2S,4S)-4-azido-1-(4-nitrobenzyloxycarbonyl)pyrrolidin-2-yl]carbonylimidazo[5,1-b]thiazol-2-yl]-6-((1R)-1-hydroxyethyl)-1-methyl-1-carbapen-2-em-3-carboxylate was prepared in the same manner as in Example, except that 157 mg of 4-nitrobenzyl (1R,3R,5R,6S)-6-((1R)-1-hydroxyethyl)-1-methyl-2-oxo-1-carbapenam-3-carboxylate and 321 mg of 7-[(2S,4S)-4-azido-1-(4-nitrobenzyloxycarbonyl)pyrrolidin-2-yl]carbonyl-2-(tri-n-butylstannyl)imidazo[5,1-b]thiazole were used as the starting compounds.

b) (1S,5R,6S)-2-[7-((2S,4S)-4-Aminopyrrolidin-2-yl)carbonylimidazo[5,1-b]thiazol-2-yl]-6-((1R)-1-hydroxyethyl)-1-methyl-1-carbapen-2-em-3-carboxylate The title compound (23 mg) was prepared in the same manner as in step b) of Example 1, except that 130 mg of the crude compound of 4-nitrobenzyl (1S,5R,6S)-2-[7-[(2S,4S)-4-azido-1-(4-nitrobenzyloxycarbonyl)pyrrolidin-2-yl]carbonyl-imidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.65 ppm): 1.11 (3H, d, J=7.1 Hz), 1.21 (3H, d, J=6.4 Hz), 2.13 (1H, m), 2.97 (1H, m), 3.31 (1H, m), 3.40 (2H, m), 3.60 (1H, m), 4.07 (1H, m), 4.17 (2H, m), 4.92 (1H, m), 7.89 (1H, s), 8.06 (1H, s)

Example 30

Sodium (1S,5R,6S)-2-[7-[5-(2-aminoethanesulfonyl)pyridin-3-yl]carbonylimidazo[5,1-b]thiazol-2-yl]-6-((1R)-1-hydroxyethyl)-1-methyl-1-carbapen-2-em-3-carboxylate (Compound No. 30)

a) 4-Nitrobenzyl (1S,5R,6S)-2-[7-[5-(2-azidoethanesulfonyl)pyridin-3-yl]carbonylimidazo[5,1-b]thiazol-2-yl]-6-((1R)-1-hydroxyethyl)-1-methyl-1-carbapen-2-em-3-carboxylate Under ice cooling, 123 mg of m-chloroperbenzoic acid was added to 5 ml of a solution of 112 mg of 4-nitrobenzyl (1S,5R,6S)-2-[7-[5-(2-azidoethylthio)pyridin-3-yl]carbonylimidazo[5,1-b]thiazol-2-yl]-6-((1R)-1-hydroxyethyl)-1-methyl-1-carbapen-2-em-3-carboxylate in dichloromethane, and the mixture was stirred for 4 hr. An aqueous sodium thiosulfate solution was added to the reaction solution, and the mixture was extracted with dichloromethane, followed by washing with brine. The organic layer was dried over anhydrous magnesium sulfate, and the solvent was then removed by distillation. The residue was purified by column chromatography (dichloromethane:methanol=1:1) on Sephadex LH-20 to give 70 mg of 4-nitrobenzyl (1S,5R,6S)-2-[7-[5-(2-azidoethanesulfonyl)pyridin-3-yl]carbonylimidazo[5,1-b]thiazol-2-yl]-6-((1R)-1-hydroxyethyl)-1-methyl-1-carbapen-2-em-3-carboxylate.

NMR (CDCl$_3$) δ: 1.33 (3H, d, J=7.3 Hz), 1.38 (3H, d, J=6.3 Hz), 3.56 (2H, t, J=5.5 Hz), 3.59 (1H, m), 3.81–3.89 (3H, m), 4.23 (1H, m), 4.42 (1H, dd, J$_1$=9.7 Hz, J$_2$=2.9 Hz), 5.32 (1H, d, J=13.6 Hz), 5.53 (1H, d, J=13.6 Hz), 7.69 (2H, d, J=9.0), 8.14 (1H, s), 8.24 (2H, d, J=9.0 Hz), 8.52 (1H, s), 9.27 (1H, m), 9.44 (1H, m), 9.92 (1H, m)

b) Sodium (1S,5R,6S)-2-[7-[5-(2-aminoethanesulfonyl)pyridin-3-yl]carbonylimidazo[5,1-b]thiazol-2-yl]-6-((1R)-1-hydroxyethyl)-1-methyl-1-carbapen-2-em-3-carboxylate The title compound (10 mg) was prepared in the same manner as in step b) of Example 1, except that 69 mg of 4-nitrobenzyl (1S,5R,6S)-2-[7-[5-(2-azidoethanesulfonyl)pyridin-3-yl]carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.65 ppm): 1.10 (3H, d, J=7.3 Hz), 1.21 (3H, d, J=6.3 Hz), 3.38–3.50 (4H, m), 3.83 (2H, t, J=7.0 Hz), 4.13–4.22 (2H, m), 7.88 (1H, s), 8.03 (1H, s), 8.83 (1H, m), 9.04 (1H, m), 9.26 (1H, m)

Example 31

(1S,5R,6S)-2-[7-[5-(2-Aminoethylthio)-1-carbamoylmethylpyridinium-3-yl]carbonylimidazo[5,1-b]-thiazol-2-yl]-6-((1R)-1-hydroxyethyl)-1-methyl-1-carbapen-2-em-3-carboxylate (intramolecular salt, hydrochloride) (Compound No. 31)

a) 4-Nitrobenzyl (1S,5R,6S)-2-[7-[5-(2-azidoethylthio)-1-carbamoylmethylpyridinium-3-yl]carbonylimidazo[5,1-b]-thiazol-2-yl]-6-((1R)-1-hydroxyethyl)-1-methyl-1-carbapen-2-em-3-carboxylate iodide 4-Nitrobenzyl (1S,5R,6S)-2-[7-[5-(2-azidoethylthio)-1-carbamoylmethylpyridinium-3-yl]carbonylimidazo[5,1-b]thiazol-2-yl]-6-((1R)-1-hydroxyethyl)-1-methyl-1-carbapen-2-em-3-carboxylate iodide (140 mg) was prepared in the same manner as in step a) of Example 2, except that 114 mg of 4-nitrobenzyl (1S,5R,6S)-2-[7-[5-(2-azidoethylthio)pyridin-3-yl]carbonylimidazo[5,1-b]-thiazol-2-yl]-6-((1R)-1-hydroxyethyl)-1-methyl-1-carbapen-2-em-3-carboxylate and 312 mg of 2-iodoacetamide were used as the starting compounds.

NMR (DMSO-d$_6$) δ: 1.19 (3H, d, J=6.1 Hz), 1.24 (3H, d, J=7.3 Hz), 3.46 (1H, dd, J$_1$=6.0 Hz, J$_2$=2.9 Hz), 3.51 (2H, t, J=6.4 Hz), 3.73 (2H, t, J=6.4 Hz), 3.78 (1H, m), 4.04 (1H, m), 4.37 (1H, dd, J$_1$=10.0 Hz, J$_2$=2.9 Hz), 5.16 (1H, d, J=5.1 Hz), 5.41 (1H, d, J=13.6 Hz), 5.48 (2H, s), 5.54 (1H, d, J=13.6 Hz), 7.71–7.77 (3H, m), 8.04 (1H, br s), 8.21 (2H, d, J=8.8 Hz), 8.55 (1H, s), 8.68 (1H, s), 9.21 (1H, m), 9.46 (1H, m), 9.51 (1H, m)

b) (1S,5R,6S)-2-[7-[5-(2-Aminoethylthio)-1-carbamoylmethylpyridinium-3-yl]carbonylimidazo[5,1-b]thiazol-2-yl]-6-((1R)-1-hydroxyethyl)-1-methyl-1-carbapen-2-em-3-carboxylate (intramolecular salt, hydrochloride)

The title compound (13 mg) was prepared in the same manner as in step b) of Example 4, except that 140 mg of 4-nitrobenzyl (1S,5R,6S)-2-[7-[5-(2-azidoethylthio)-1-carbamoylmethylpyridinium-3-yl]carbonylimidazo[5,1-b]thiazol-2-yl]-6-((1R)-1-hydroxyethyl)-1-methyl-1-carbapen-2-em-3-carboxylate iodide was used as the starting compound.

NMR (D$_2$O) δ (HOD=4.65 ppm): 1.08 (3H, d, J=7.1 Hz), 1.19 (3H, d, J=6.1 Hz), 3.29 (2H, d, J=6.5 Hz), 3.33–3.55 (4H, m), 4.05 (1H, m), 4.13 (1H, m), 5.49 (2H, s), 7.86 (1H, s), 7.97 (1H, s), 8.84 (1H, s), 9.11 (1H, s), 9.30 (1H, s)

Example 32

Sodium (1S,5R,6S)-6-((1R)-1-hydroxyethyl)-2-[7-(isoquinolin-4-yl)carbonylimidazo[5,1-b]thiazol-2-yl]-1-methyl-1-carbapen-2-em-3-carboxylate (Compound No. 34)

4-Nitrobenzyl (1S,5R,6S)-6-((1R)-1-hydroxyethyl)-2-[7-(isoquinolin-4-yl)carbonylimidazo[5,1-b]thiazol-2-yl]-1-methyl-1-carbapen-2-em-3-carboxylate was synthesized in substantially the same manner as in Example 1, except that 324 mg of 4-nitrobenzyl (1R,3R,5R,6S)-6-((1R)-1-hydroxyethyl)-1-methyl-2-oxo-1-carbapenam-3-carboxylate and 358 mg of 7-(isoquinolin-4-yl)carbonyl-2-(tri-n-butylstannyl)imidazo[5,1-b]thiazole were used as the starting compounds. The title compound (22.3 mg) was synthesized from 72.8 mg of this compound.

NMR (DMSO-d$_6$) δ: 1.09 (3H, d, J=7.0 Hz), 1.12 (3H, d, J=6.1 Hz), 3.07 (1H, dd, J$_1$=6.8 Hz, J$_2$=2.7 Hz), 3.36 (1H, m), 3.87 (1H, m), 4.01 (1H, dd, J$_1$=9.3 Hz, J$_2$=2.4 Hz), 4.95 (1H, d, J=5.1 Hz), 7.68 (1H, t, J=7.8 Hz), 7.76 (1H, m), 8.16–8.19 (3H, m), 8.21 (1H, s), 8.96 (1H, s), 9.39 (1H, s)

Example 33

Sodium (1S,5R,6S)-2-[7-(1-carbamoylmethyldihydroisoquinolin-4-yl)carbonylimidazo-[5,1-b]thiazol-2-yl]-6-((1R)-1-hydroxyethyl)-1-methyl-1-carbapen-2-em-3-carboxylate (Compound No. 35)

The title compound (19.9 mg) was synthesized in substantially the same manner as in Example 2, except that 93.0 mg of 4-nitrobenzyl (1S,5R,6S)-6-((1R)-1-hydroxyethyl)-2-[7-(isoquinolin-4-yl)carbonylimidazo-[5,1-b]thiazol-2-yl]-1-methyl-1-carbapen-2-em-3-carboxylate was used as the starting compound.

NMR (DMSO-d$_6$) δ: 1.07 (3H, d, J=7.1 Hz), 1.11 (3H, d, J=6.1 Hz), 3.07 (1H, m), 3.31 (1H, m), 3.86 (1H, m), 4.02 (1H, m), 4.94 (1H, d, J=5.4 Hz), 5.51 (2H, s), 6.96 (1H, m), 6.98 (1H, m), 7.22 (1H, s), 7.56 (1H, s), 8.06–8.23 (3H, m), 8.51 (1H, d, J=8.3 Hz), 9.11 (1H, s)

Example 34

(1S,5R,6S)-2-[7-(1-Carbamoylmethyl-5-methylthiopyridium-3-yl)carbonylimidazo[5,1-b]thiazol-2-yl]-6-((1R)-1-hydroxyethyl)-1-methyl-1-carbapen-2-em-3-carboxylate (intramolecular salt) (Compound No. 40)

The title compound (38.0 mg) was synthesized in substantially the same manner as in Example 2, except that 155 mg of 4-nitrobenzyl (1S,5R,6S)-6-((1R)-1-hydroxyethyl)-1-methyl-2-[7-(5-methylthiopyridin-3-yl)carbonylimidazo[5,1-b]thiazol-2-yl]-1-carbapen-2-em-3-carboxylate was used as the starting compound.

NMR (DMSO-d$_6$) δ: 1.09 (3H, d, J=7.0), 1.11 (3H, d, J=6.1 Hz), 2.67 (3H, s), 3.08 (1H, m), 3.35 (1H, m), 3.87 (1H, m), 4.01 (1H, dd, J$_1$=9.5 Hz, J$_2$=2.7 Hz), 4.96 (1H, d, J=5.1 Hz), 5.43 (2H, s), 7.67 (1H, br s), 8.03 (1H, br s), 8.23 (1H, s), 8.31 (1H, s), 8.99 (1H, br s), 9.30 (1H, br s), 9.41 (1H, br s)

Example 35

(1S,5R,6S)-2-[7-[1-((2R)-3-Amino-2-hydroxypropyl)pyridinium-3-yl]carbonylimidazo[5,1-b]thiazol-2-yl]-6-((1R)-1-hydroxyethyl)-1-methyl-1-carbapen-2-em-3-carboxylate (intramolecular salt, hydrochloride) (Compound No. 48)

a) 4-Nitrobenzyl (1S,5R,6S)-2-[7-[1-((2R)-3-azido-2-triethylsilyloxypropyl)pyridinium-3-yl]carbonylimidazo[5, 1-b]thiazol-2-yl]-6-((1R)-1-hydroxyethyl)-1-methyl-1-carbapen-2-em-3-carboxylate trifluoromethanesulfonate A crude compound (398 mg) of 4-nitrobenzyl (1S,5R,6S)-2-[7-[1-((2R)-3-azido-2-triethylsilyloxypropyl)pyridinium-3-yl]carbonylimidazo[5,1-b]thiazol-2-yl]-6-((1R)-1-hydroxyethyl)-1-methyl-1-carbapen-2-em-3-carboxylate trifluoromethanesulfonate was prepared in the same manner as in step a) of Example 4, except that 255 mg of 4-nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate and (2R)-3-azido-2-triethylsilyloxypropanol were used as the starting compounds.

b) (1S,5R,6S)-2-[7-[1-((2R)-3-Amino-2-hydroxypropyl)pyridinium-3-yl]carbonylimidazo[5,1-b]thiazol-2-yl]-6-((1R)-1-hydroxyethyl)-1-methyl-1-carbapen-2-em-3-carboxylate (intramolecular salt, hydrochloride)

The crude product (398 mg) of 4-nitrobenzyl (1S,5R,6S)-2-[7-[1-((2R)-3-azido-2-triethylsilyloxypropyl)pyridinium-3-yl]carbonylimidazo[5,1-b]thiazol-2-yl]-6-((1R)-1-hydroxyethyl)-1-methyl-1-carbapen-2-em-3-carboxylate trifluoromethanesulfonate was dissolved in 12 ml of THF and 12 ml of water to prepare a solution. The solution was adjusted to pH 2.2 by the addition of 1 N hydrochloric acid and was stirred for 24 hr. The solution was adjusted to pH 5 by the addition of a 5% aqueous sodium hydrogencarbonate solution, and a reaction was then carried out in the same manner as in step b) of Example 4. Thus, 56 mg of the title compound was prepared.

NMR (D$_2$O) δ (HOD=4.65 ppm): 1.04 (3H, d, J=7.3 Hz), 1.18 (3H, d, J=6.4 Hz), 3.08 (1H, m), 3.23–3.39 (3H, m), 4.02 (1H, dd, J$_1$=9.0 Hz, J$_2$=2.4 Hz), 4.13 (1H, m), 4.43 (1H, m), 4.55 (1H, m), 4.94 (1H, m), 7.77 (1H, s), 7.90 (1H, s), 8.08 (1H, m), 8.89 (1H, m), 9.18 (1H, m), 9.58 (1H, s)

Example 36

Sodium (1S,5R,6S)-6-((1R)-1-hydroxyethyl)-1-methyl-2-[7-(piperidin-4-yl)carbonylimidazo[5,1-b]-thiazol-2-yl]-1-carbapen-2-em-3-carboxylate (Compound No. 53)

a) 4-Nitrobenzyl (1S,5R,6S)-6-((1R)-1-hydroxyethyl)-1-methyl-2-[7-[1-(4-nitrobenzyloxycarbonyl)piperidin-4-yl]carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[7-[1-(4-nitrobenzyloxycarbonyl)piperidin-4-yl]carbonylimidazo[5,1-b]thiazol-2-yl]-1-carbapen-2-em-3-carboxylate (1.16 g) was prepared in the same manner as in step a) of Example 1, except that 938 mg of 4-nitrobenzyl (1R,3R,5R,6S)-6-((1R)-1-hydroxyethyl)-1-methyl-2-oxo-1-carbapenam-3-carboxylate and 1.91 g of 7-[1-(4-nitrobenzyloxycarbonyl)piperidin-4-yl]carbonyl-2-(tri-n-butylstannyl)imidazo[5,1-b]thiazole were used as the starting compounds.

NMR (CDCl$_3$) δ: 1.30 (3H, d, J=7.2 Hz), 1.40 (3H, d, J=6.3 Hz), 1.7–2.1 (4H, m), 3.0–3.2 (2H, m), 3.35–3.4 (1H, m), 3.4–3.6 (1H, m), 3.6–3.7 (1H, m), 4.2–4.4 (3H, m), 4.41 (1H, dd, J$_1$=9.9 Hz, J$_2$=2.7 Hz), 5.24 (2H, s), 5.27 (1H, d, J=13.5 Hz), 5.52 (1H, d, J=13.5 Hz), 7.52 (2H, d, J=8.7 Hz), 7.67 (2H, d, J=9.0 Hz), 8.01 (1H, s), 8.2–8.3 (4H, m), 8.51 (1H, s)

b) Sodium (1S,5R,6S)-6-((1R)-1-hydroxyethyl)-1-methyl-2-[7-(piperidin-4-yl)carbonylimidazo[5,1-b]thiazol-2-yl]-1-carbapen-2-em-3-carboxylate The title compound (142 mg) was prepared in the same manner as in step b) of Example 1, except that 344 mg of 4-nitrobenzyl (1S,5R,6S)-6-((1R)-1-hydroxyethyl)-1-methyl-2-[7-[1-(4-nitrobenzyloxycarbonyl)piperidin-4-yl]carbonylimidazo[5,1-b]thiazol-2-yl]-1-carbapen-2-em-3-carboxylate was used as the starting compound.

NMR (D$_2$O) δ (HOD=4.80 ppm): 1.21 (3H, d, J=6.9 Hz), 1.33 (3H, d, J=6.3 Hz), 1.8–2.0 (2H, m), 2.05–2.2 (2H, m), 3.1–3.25 (2H, m), 3.25–3.6 (5H, m), 4.2–4.35 (2H, m), 7.92 (1H, s), 8.02 (1H, s)

Example 37

(1S,5R,6S)-2-[7-[5-(2-Aminoethyl)thio-1-carboxylmethylpyridinium-3-yl]carbonylimidazo[5,1-b]-thiazol-2-yl]-6-((1R)-1-hydroxyethyl)-1-methyl-1-carbapen-2-em-3-carboxylate (intramolecular salt) (Compound No. 54)

The title compound (12 mg) was prepared in the same manner as in steps a) and b) of Example 4, except that 3-azido-1-propanol and 4-nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate used in step a) of Example 4 were changed to 63 mg of 4-nitrobenzyl hydroxyacetate and 168 mg of 4-nitrobenzyl (1S,5R,6S)-2-[7-[5-(2-azidoethyl)thiopyridin-3-yl]carbonylimidazo[5,1-b]thiazol-2-yl]-6-((1R)-1-hydroxyethyl)-1-methyl-1-carbapen-2-em-3-carboxylate, respectively.

NMR (D$_2$O) δ (HOD=4.65 ppm): 1.07 (3H, d, J=7.3 Hz), 1.19 (3H, d, J=6.6 Hz), 3.25–3.37 (4H, m), 3.45 (2H, m), 4.04 (1H, dd, J$_1$=9.4 Hz, J$_2$=2.3 Hz), 4.13 (1H, m), 5.18 (2H, m), 7.80 (1H, s), 7.85 (1H, s), 8.76 (1H, s), 8.97 (1H, s), 9.19 (1H, s)

Example 38

Sodium (5R,6S)-6-((1R)-1-hydroxyethyl)-2-[7-(pyridin-3-yl)carbonylimidazo[5,1-b]thiazol-2-yl]-1-carbapen-2-em-3-carboxylate (Compound No. 58)

a) 4-Nitrobenzyl (5R,6S)-6-((1R)-1-hydroxyethyl)-2-[7-(pyridin-3-yl)carbonylimidazo[5,1-b]thiazol-2-yl]-1-carbapen-2-em-3-carboxylate 4-Nitrobenzyl (5R,6S)-6-((1R)-1-hydroxyethyl)-2-[7-(pyridin-3-yl)carbonylimidazo[5,1-b]thiazol-2-yl]-1-carbapen-2-em-3-carboxylate (469 mg) was prepared in the same manner as in step a) of Example 1, except that 400 mg of 4-nitrobenzyl (3R,5R,6S)-6-((1R)-1-hydroxyethyl)-2-oxo-1-carbapenam-3-carboxylate and 700 mg of 7-(pyridin-3-yl)carbonyl-2-(tri-n-butylstannyl)imidazo[5,1-b]thiazole were used as the starting compounds.

NMR (CDCl$_3$) δ: 1.41 (3H, d, J=6.3 Hz), 3.34–3.46 (3H, m), 4.29–4.43 (2H, m), 5.34 (1H, d, J=13.6 Hz), 5.57 (1H, d, J=13.6 Hz), 7.45 (1H, m), 7.72 (2H, d, J=8.8 Hz), 8.09 (1H, s), 8.26 (2H, d, J=8.8 Hz), 8.51 (1H, s), 8.72–8.85 (2H, m), 8.75–8.85 (1H, m), 9.72 (1H, m)

b) Sodium (5R,6S)-6-((1R)-1-hydroxyethyl)-2-[7-(pyridin-3-yl)carbonylimidazo[5,1-b]thiazol-2-yl]-1-carbapen-2-em-3-carboxylate The title compound (50 mg) was prepared in the same manner as in step b) of Example 1, except that 89 mg of 4-nitrobenzyl (5R,6S)-6-((1R)-1-hydroxyethyl)-2-[7-(pyridin-3-yl)carbonylimidazo[5,1-b]thiazol-2-yl]-1-carbapen-2-em-3-carboxylate was used as the starting compound.

NMR (D$_2$O) δ (HOD=4.65 ppm): 1.16 (3H, d, J=6.3 Hz), 2.95 (2H, m), 3.24 (1H, m), 4.01 (1H, m), 4.09 (1H, m), 7.24 (1H, m), 7.54 (1H, s), 7.84 (1H, s), 8.13 (1H, m), 8.36 (1H, m), 8.77 (1H, m)

Example 39

(5R,6S)-2-[7-(1-Carbamoylmethylpyridinium-3-yl)carbonylimidazo[5,1-b]thiazol-2-yl]-6-((1R)-1-hydroxyethyl)-1-carbapen-2-em-3-carboxylate (intramolecular salt) (Compound No. 60)

The title compound (32 mg) was prepared in the same manner as in steps a) and b) of Example 2, except that 111 mg of 4-nitrobenzyl (5R,6S)-6-((1R)-1-hydroxyethyl)-2-[7-(pyridin-3-yl)carbonylimidazo[5,1-b]thiazol-2-yl]-1-carbapen-2-em-3-carboxylate was used instead of 4-nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate in step a) of Example 2.

NMR ($D_2O$) δ (HOD=4.65 ppm): 1.15 (3H, d, J=6.4 Hz), 2.99 (2H, m), 3.28 (1H, m), 3.97 (1H, m), 4.09 (1H, m), 5.50 (2H, m), 7.58 (1H, s), 7.91 (1H, s), 8.03 (1H, m), 8.78 (1H, m), 9.06 (1H, m), 9.51 (1H, s)

Example 40

(1S,5R,6S)-2-[7-(1-Carboxylmethylpyridinium-3-yl) [5,1-b]thiazol-2-yl]-6-((1R)-1-hydroxyethyl)-1-methyl-1-carbapen-2-em-3-carboxylate (intramolecular salt) (Compound No. 63)

The title compound (25 mg) was prepared in the same manner as in steps a) and b) of Example 4, except that 185 mg of 4-nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate and 95 mg of 4-nitrobenzyl hydroxyacetate were used as the starting compounds.

NMR ($D_2O$) δ (HOD=4.65 ppm): 1.13 (3H, d, J=7.3 Hz), 1.20 (3H, d, J=6.3 Hz), 3.40 (1H, m), 3.49 (1H, m), 4.12–4.22 (2H, m), 5.24 (2H, s), 8.00 (1H, s), 8.09 (1H, m), 8.14 (1H, s), 8.82 (1H, m), 9.10 (1H, m), 9.52 (1H, s)

Example 41

Sodium (1S,5R,6S)-6-((1R)-1-hydroxyethyl)-1-methyl-2-[7-(pyrrolidin-1-yl)acetylimidazo[5,1b]thiazol-2-yl]-1-carbapen-2-em-3-carboxylate (Compound No. 67)

a) 4-Nitrobenzyl (1S,5R,6S)-2-(7-chloroacetylimidazo[5,1-b]thiazol-2-yl)-6-((1R)-1-hydroxyethyl)-1-methyl-1-carbapen-2-em-3-carboxylate 4-Nitrobenzyl (1S,5R,6S)-2-(7-chloroacetylimidazo-[5,1-b]thiazol-2-yl)-6-((1R)-1-hydroxyethyl)-1-methyl-1-carbapen-2-em-3-carboxylate (1.01 g) was prepared in the same manner as in step a) of Example 1, except that 2.85 g of 4-nitrobenzyl (1R,3R,5R,6S)-6-((1R)-1-hydroxyethyl)-1-methyl-2-oxo-1-carbapenam-3-carboxylate and 1.66 g of 7-chloroacetyl-2-(tri-n-butylstannyl)imidazo[5,1-b]thiazole were used as the starting compounds.

NMR (DMSO-$d_6$) δ: 1.19 (3H, d, J=6.3 Hz), 1.23 (3H, d, J=7.2 Hz), 3.4–3.45 (1H, m), 3.7–3.8 (1H, m), 3.95–4.1 (1H, m), 4.3–4.4 (1H, m), 4.92 (2H, s), 5.39 (1H, d, J=13.8 Hz), 5.52 (1H, d, J=13.8 Hz), 7.74 (2H, d, J=9.0 Hz), 8.21 (2H, d, J=9.0 Hz), 8.38 (1H, s), 8.60 (1H, s)

b) 4-Nitrobenzyl (1S,5R,6S)-6-((1R)-1-hydroxyethyl)-1-methyl-2-[7-(pyrrolidin-1-yl)acetylimidazo[5,1-b]thiazol-2-yl]-1-carbapen-2-em-3-carboxylate 4-Nitrobenzyl (1S,5R,6S)-2-(7-chloroacetylimidazo[5,1-b]thiazol-2-yl)-6-((1R)-1-hydroxyethyl)-1-methyl-1-carbapen-2-em-3-carboxylate (161 mg) was dissolved in 5 ml of acetone to prepare a solution. Sodium iodide (67 mg) was added to the solution, and the mixture was stirred at room temperature for 1.5 hr. Brine was added to the reaction solution, and the mixture was extracted with ethyl acetate. The extract was dried over anhydrous magnesium sulfate. The solvent was removed by distillation, and the residue was dissolved in 5 ml of N,N-dimethylformamide to prepare a solution. Pyrrolidine (0.03 ml) was added to the solution, and the mixture was stirred at room temperature for 2 hr. Brine was added to the reaction solution, and the mixture was extracted with ethyl acetate. The extract was dried over anhydrous magnesium sulfate. The solvent was removed by distillation, and the residue was washed with diethyl ether to give 4-nitrobenzyl (1S,5R,6S)-6-((1R)-1-hydroxyethyl)-1-methyl-2-[7-(pyrrolidin-1-yl)acetylimidazo[5,1-b]thiazol-2-yl]-1-carbapen-2-em-3-carboxylate.

NMR (DMSO-$d_6$) δ: 1.15–1.25 (6H, m), 1.7–1.8 (4H, m), 2.6–2.75 (4H, m), 3.4–3.45 (1H, m), 3.7–3.8 (1H, m), 3.85–4.1 (2H, m), 4.3–4.4 (1H, m), 5.39 (1H, d, J=13.8 Hz), 5.52 (1H, d, J=13.8 Hz), 7.72 (2H, d, J=8.7 Hz), 8.21 (2H, d, J=8.7 Hz), 8.32 (1H, s), 8.54 (1H, s)

c) Sodium (1S,5R,6S)-6-((1R)-1-hydroxyethyl)-1-methyl-2-[7-(pyrrolidin-1-yl)acetylimidazo[5,1-b]thiazol-2-yl]-1-carbapen-2-em-3-carboxylate The title compound (41.7 mg) was prepared in the same manner as in step b) of Example 1, except that 200 mg of 4-nitrobenzyl (1S,5R,6S)-6-((1R)-1-hydroxyethyl)-1-methyl-2-[7-(pyrrolidin-1-yl)acetylimidazo[5,1-b]thiazol-2-yl]-1-carbapen-2-em-3-carboxylate was used as the starting compound.

NMR ($D_2O$) δ (HOD=4.80 ppm): 1.23 (3H, d, J=6.9 Hz), 1.35 (3H, d, J=6.3 Hz), 2.1–2.2 (4H, m), 3.4–3.7 (6H, m), 4.25–4.4 (2H, m), 4.7–4.8 (2H, m), 7.93 (1H, s), 8.14 (1H, s)

Compound Nos. 55, 61, 72, 93, 95, 111, and 113 were synthesized in the same manner as in Example 41.

Example 42

Sodium (1S,5R,6S)-2-[7-[5-(2-aminoethyl) thiomethyl-pyridin-3-yl]carbonylimidazo[5,1-b] thiazol-2-yl]-6-((1R)-1-hydroxyethyl)-1-methyl-1-carbapen-2-em-3-carboxylate (Compound No. 68)

a) 4-Nitrobenzyl (1S,5R,6S)-2-[7-[5-(2-azidoethyl)-thiomethyl-pyridin-3-yl]carbonylimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[7-[5-(2-azidoethyl)-thiomethyl-pyridin-3-yl]carbonylimidazo[5,1-b]thiazol-2-yl]-6-((1R)-1-hydroxyethyl)-1-methyl-1-carbapen-2-em-3-carboxylate (457 mg) was prepared in the same manner as in step a) of Example 1, except that 461 mg of 4-nitrobenzyl (1R,3R,5R,6S)-6-((1R)-1-hydroxyethyl)-1-methyl-2-oxo-1-carbapenam-3-carboxylate and 856 mg of [7-[5-(2-azidoethyl)thiomethyl-pyridin-3-yl]carbonyl-2-(tri-n-butylstannyl)imidazo[5,1-b]thiazole were used as the starting compounds.

NMR ($CDCl_3$) δ: 1.34 (3H, d, J=7.3 Hz), 1.41 (3H, d, J=6.3 Hz), 2.62 (2H, t, J=6.7 Hz), 3.41 (1H, dd, $J_1$=6.6 Hz, $J_2$=3.0 Hz), 3.48 (2H, t, J=6.7 Hz), 3.57 (1H, m), 3.88 (2H, s), 4.34 (1H, m), 4.43 (1H, dd, $J_1$=9.7 Hz, $J_2$=2.9 Hz), 5.30 (1H, d, J=13.7 Hz), 5.54 (1H, d, J=13.7 Hz), 7.69 (2H, d, J=9.0 Hz), 8.10 (1H, s), 8.25 (2H, d, J=9.0 Hz), 8.58 (1H, s), 8.74 (1H, m), 8.81 (1H, m), 9.63 (1H, m)

b) Sodium (1S,5R,6S)-2-[7-[5-(2-aminoethyl) thiomethylpyridin-3-yl]carbonylimidazo[5,1-b]thiazol-2-yl]-6-((1R)-1-hydroxyethyl)-1-methyl-1-carbapen-2-em-3-carboxylate The title compound (19 mg) was prepared in the same manner as in step b) of Example 1, except that 96 mg of 4-nitrobenzyl (1S,5R,6S)-2-[7-[5-(2-azidoethyl)thiomethyl-pyridin-3-yl]carbonylimidazo[5,1-b]thiazol-2-yl]-6-((1R)-1-hydroxyethyl)-1-methyl-1-carbapen-2-em-3-carboxylate was used as the starting compound.

NMR ($D_2O$) δ (HOD=4.65 ppm): 0.99 (3H, d, J=7.1 Hz), 1.18 (3H, d, J=6.1 Hz), 2.67 (2H, t, J=6.7 Hz), 3.10 (2H, t, J=6.7 Hz), 3.28–3.35 (2H, m), 3.62 (2H, S), 4.05–4.16 (2H, m), 7.67 (1H, s), 7.81 (1H, s), 8.03 (1H, s), 8.22 (1H, s), 8.49 (1H, s)

Example 43

(1S,5R,6S)-2-[7-[5-(2-Aminoethyl)thiomethyl-1-carboxymethylpyridinium-3-yl]carbonylimidazo[5,1-b]thiazol-2-yl]-6-((1R)-1-hydroxyethyl)-1-methyl-1-carbapen-2-em-3-carboxylate (intramolecular salt) (Compound No. 69)

The title compound (9 mg) was prepared in the same manner as in steps a) and b) of Example 4, except that 105 mg of 4-nitrobenzyl (1S,5R,6S)-2-[7-[5-(2-azidoethyl)thiomethyl-pyridin-3-yl]carbonylimidazo[5,1-b]thiazol-2-yl]-6-((1R)-1-hydroxyethyl)-1-methyl-1-carbapen-2-em-3-carboxylate and 45 mg of 4-nitrobenzyl hydroxyacetate were used as the starting compounds.

NMR ($D_2O$) δ (HOD=4.65 ppm): 1.10 (3H, d, J=6.8 Hz), 1.18 (3H, d, J=6.3 Hz), 2.72 (2H, t, J=6.8 Hz), 3.09 (2H, t, J=6.8 Hz), 3.36–3.49 (2H, m), 3.99 (2H, s), 4.10–4.17 (2H, m), 5.19 (2H, s), 7.95 (1H, s), 8.08 (1H, s), 8.87 (1H, s), 9.11 (1H, s), 9.38 (1H, s)

Example 44

Sodium (1S,5R,6S)-6-((1R)-1-hydroxyethyl)-1-methyl-2-[7-[5-(piperazin-1-yl)methylpyridin-3-yl]carbonylimidazo[5,1-b]thiazol-2-yl]-1-carbapen-2-em-3-carboxylate (Compound No. 80)

a) 4-Nitrobenzyl (1S,5R,6S)-6-((1R)-1-hydroxyethyl)-1-methyl-2-[7-[5-[4-(4-nitrobenzyloxycarbonyl)piperazin-1-yl]methylpyridin-3-yl]carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[7-[5-[4-(4-nitrobenzyloxycarbonyl)piperazin-1-yl]methylpyridin-3-yl]carbonylimidazo[5,1-b]thiazol-2-yl]-1-carbapen-2-em-3-carboxylate (172 mg) was prepared in the same manner as in step a) of Example 1, except that 337 mg of 4-nitrobenzyl (1R,3R,5R,6S)-6-((1R)-1-hydroxyethyl)-1-methyl-2-oxo-1-carbapenam-3-carboxylate and 780 mg of 7-[5-[4-(4-nitrobenzyloxycarbonyl)-piperazin-1-yl]methylpyridin-3-yl]carbonyl-2-(tri-n-butylstannyl)imidazo[5,1-b]thiazole were used as the starting compounds.

NMR ($CDCl_3$) δ: 1.34 (3H, d, J=7.1 Hz), 1.41 (3H, d, J=6.3 Hz), 2.45 (4H, m), 3.41 (1H, dd, $J_1$=6.3 Hz, $J_2$=2.9 Hz), 3.54 (5H, m), 3.66 (2H, s), 4.33 (1H, m), 4.44 (1H, dd, $J_1$=9.7 Hz, $J_2$=2.9 Hz), 5.23 (2H, s), 5.30 (1H, d, J=13.3 Hz), 5.54 (1H, d, J=13.3 Hz), 7.50 (2H, d, J=8.8 Hz), 7.69 (2H, d, J=8.9 Hz), 8.09 (1H, s), 8.22 (2H, d, J=8.8 Hz), 8.25 (2H, d, J=8.9 Hz), 8.57 (1H, s), 8.69 (1H, dd, $J_1$=2.1 Hz, $J_2$=2.0 Hz), 8.74 (1H, d, J=2.1 Hz), 9.67 (1H, d, J=2.0 Hz)

b) Sodium (1S,5R,6S)-6-((1R)-1-hydroxyethyl)-1-methyl-2-[7-[5-(piperazin-1-yl)methylpyridin-3-yl]carbonyl imidazo[5,1-b]thiazol-2-yl]-1-carbapen-2-em-3-carboxylate The title compound (59 mg) was prepared in the same manner as in step b) of Example 1, except that 172 mg of 4-nitrobenzyl (1S,5R,6S)-6-((1R)-1-hydroxyethyl)-1-methyl-2-[7-[5-[4-(4-nitrobenzyloxycarbonyl)piperazin-1-yl]methylpyridin-3-yl]carbonylimidazo[5,1-b]thiazol-2-yl]-1-carbapen-2-em-3-carboxylate was used as the starting compound.

NMR ($D_2O$) δ (HOD=4.65 ppm): 1.03 (3H, d, J=7.1 Hz), 1.18 (3H, d, J=6.1 Hz), 2.66 (4H, m), 3.15 (4H, m), 3.33–3.43 (2H, m), 3.56 (2H, s), 4.09–4.16 (2H, m), 7.77 (1H, s), 7.89 (1H, s), 8.12 (1H, m), 8.30 (1H, m), 8.66 (1H, m)

Example 45

(1S,5R,6S)-2-[7-[5-(2-Aminoethyl)thiomethyl-1-carbamoylmethylpyridinium-3-yl]carbonylimidazo[5,1-b]-thiazol-2-yl]-6-((1R)-1-hydroxyethyl)-1-methyl-1-carbapen-2-em-3-carboxylate (intramolecular salt, hydrochloride) (Compound No. 81)

The title compound (9 mg) was prepared in the same manner as in steps a) and b) of Example 2, except that 114 mg of 4-nitrobenzyl (1S,5R,6S)-2-[7-[5-(2-azidoethyl)thiomethyl-pyridin-3-yl]carbonylimidazo[5,1-b]thiazol-2-yl]-6-((1R)-1-hydroxyethyl)-1-methyl-1-carbapen-2-em-3-carboxylate was used as the starting compound.

NMR ($D_2O$) δ (HOD=4.65 ppm): 1.10 (3H, d, J=7.3 Hz), 1.18 (3H, d, J=6.4 Hz), 2.72 (2H, t, J=6.6 Hz), 3.11 (2H, t, J=6.6 Hz), 3.37 (1H, m), 3.45 (1H, m), 4.01 (2H, s), 4.10–4.15 (2H, m), 5.51 (2H, s), 7.98 (1H, s), 8.11 (1H, s), 8.93 (1H, s), 9.19 (1H, s), 9.46 (1H, s)

Example 46

Sodium (1S,5R,6S)-2-[7-[3-(4-ethylpiperazin-1-yl)propionyl]imidazo[5,1-b]thiazol-2-yl]-6-((1R)-1-hydroxyethyl)-1-methyl-1-carbapen-2-em-3-carboxylate (Compound No. 83)

4-Nitrobenzyl (1S,5R,6S)-6-((1R)-1-hydroxyethyl)-1-methyl-2-[7-[3-(thiomorpholin-4-yl)propionyl]imidazo[5,1-b]thiazol-2-yl]-1-carbapen-2-em-3-carboxylate was synthesized in substantially the same manner as in Example 1, except that 2.52 g of 4-nitrobenzyl (1R,3R,5R,6S)-6-((1R)-1-hydroxyethyl)-1-methyl-2-oxo-1-carbapenam-3-carboxylate and 2.30 g of 7-[3(thiomorpholin-4-yl)propionyl]-2-(tri-n-butylstannyl)imidazo[5,1-b]thiazole were used as the starting compounds. This compound was treated with mCPBA and was then treated with ethylpiperazine to synthesize 4-nitrobenzyl (1S,5R,6S)-2-[7-[3-(4-ethylpiperazin-1-yl)propionyl]imidazo[5,1-b]thiazol-2-yl]-6-((1R)-1-hydroxyethyl)-1-methyl-1-carbapen-2-em-3-carboxylate. The title compound (33.4 mg) was synthesized from 164.9 mg of this compound.

NMR (DMSO-$d_6$) δ: 0.99 (3H, t, J=7.0 Hz), 1.07 (3H, d, J=7.3 Hz), 1.10 (3H, d, J=6.3 Hz), 2.43–2.60 (8H, m), 2.68 (4H, br s), 2.96 (2H, m), 3.00 (1H, m), 3.39 (1H, m), 3.85 (1H, m), 4.02 (1H, m), 4.97 (1H, d, J=5.4 Hz), 8.08 (1H, s), 8.15 (1H, s)

Compound Nos. 46 and 85 were synthesized in the same manner as in Example 46.

Example 47

(1S,5R,6S)-2-[7-[5-(3-Aminopropyl)thio-1-carbamoylmethylpyridinium-3-yl]carbonylimidazo[5,1-b]-thiazol-2-yl]-6-((1R)-1-hydroxyethyl)-1-methyl-1-carbapen-2-em-3-carboxylate (intramolecular salt, hydrochloride) (Compound No. 92)

The title compound (10 mg) was prepared in the same manner as in steps a) and b) of Example 2, except that 141 mg of 4-nitrobenzyl (1S,5R,6S)-2-[7-[5-(3-azidopropyl)thiopyridin-3-yl]carbonylimidazo[5,1-b]thiazol-2-yl]-6-((1R)-1-hydroxyethyl)-1-methyl-1-carbapen-2-em-3-carboxylate was used as the starting compound.

NMR ($D_2O$) δ (HOD=4.65 ppm): 1.09 (3H, d, J=7.3 Hz), 1.17 (3H, d, J=6.4 Hz), 2.00 (2H, m), 3.07 (2H, t, J=7.7 Hz), 3.22 (2H, t, J=7.2 Hz), 3.35–3.47 (2H, m), 4.07–4.17 (2H, m), 5.46 (2H, s), 7.94 (1H, s), 8.07 (1H, s), 8.75 (1H, s), 9.01 (1H, s), 9.28 (1H, s)

Example 48

Sodium (1S,5R,6S)-6-((1R)-1-hydroxyethyl)-1-methyl-2-[5-phenyl-7-(pyridin-3-yl)carbonylimidazo[5,1-b]thiazol-2-yl]-1-carbapen-2-em-3-carboxylate (Compound No. 94)

4-Nitrobenzyl (1S,5R,6S)-6-((1R)-1-hydroxyethyl)-1-methyl-2-[5-phenyl-7-(pyridin-3-yl)carbonylimidazo[5,1-b]

thiazol-2-b]thiazol-2-yl]-1-carbapen-2-em-3-carboxylate was synthesized in substantially the same manner as in Example 1, except that 480 mg of 4-nitrobenzyl (1R,3R,5R,6S)-6-((1R)-1-hydroxyethyl)-1-methyl-2-oxo-1-carbapenam-3-carboxylate and 417 mg of 5-phenyl-7-(pyridin-3-yl)carbonyl-2-(tri-n-butylstannyl)imidazo[5,1-b]thiazole were used as the starting compounds. The title compound (48.0 mg) was synthesized from 97.0 mg of this compound.

NMR (DMSO-d$_6$) δ: 1.07 (3H, d, J=7.1 Hz), 1.11 (3H, d, J=6.1 Hz), 3.09 (1H, m), 3.63 (1H, m), 3.91 (1H, m), 4.03 (1H, m), 4.96 (1H, d, J=5.6 Hz), 7.45 (1H, m), 7.52–7.55 (3H, m), 7.96 (2H, d, J=8.6 Hz), 8.40 (1H, s), 8.72 (1H, s), 8.73 (1H, s), 9.59 (1H, s)

Example 49

Sodium (1S,5R,6S)-2-[5-chloro-7-(pyridin-3-yl)carbonylimidazo[5,1-b]thiazol-2-yl]-6-((1R)-1-hydroxyethyl)-1-methyl-1-carbapen-2-em-3-carboxylate (Compound No. 100)

a) 4-Nitrobenzyl (1S,5R,6S)-2-[5-chloro-7-(pyridin-3-yl)carbonylimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[5-chloro-7-(pyridin-3-yl)carbonylimidazo[5,1-b]thiazol-2-yl]-6-((1R)-1-hydroxyethyl)-1-methyl-1-carbapen-2-em-3-carboxylate (712 mg) was prepared in the same manner as in step a) of Example 1, except that 474 mg of 4-nitrobenzyl (1R,3R,5R,6S)-6-((1R)-1-hydroxyethyl)-1-methyl-2-oxo-1-carbapenam-3-carboxylate and 730 mg of 5-chloro-7-(pyridin-3-yl)carbonyl-2-(tri-n-butylstannyl)imidazo[5,1-b]thiazole were used as the starting compounds.

NMR (CDCl$_3$) δ: 1.35 (3H, d, J=7.3 Hz), 1.41 (3H, d, J=6.3 Hz), 3.42 (1H, dd, J$_1$=6.6 Hz, J$_2$=3.0 Hz), 3.57 (1H, m), 4.34 (1H, m), 4.43 (1H, dd, J$_1$=9.7 Hz, J$_2$=2.7 Hz), 5.31 (1H, d, J=13.4 Hz), 5.56 (1H, d, J=13.4 Hz), 7.46 (1H, m), 7.69 (2H, d, J=8.7 Hz), 8.25 (2H, d, J=8.7 Hz), 8.34 (1H, s), 8.77–8.84 (2H, m), 9.68 (1H, m)

b) Sodium (1S,5R,6S)-2-[5-chloro-7-(pyridin-3-yl)carbonylimidazo[5,1-b]thiazol-2-yl]-6-((1R)-1-hydroxyethyl)-1-methyl-1-carbapen-2-em-3-carboxylate The title compound (49 mg) was prepared in the same manner as in step b) of Example 1, except that 91 mg of 4-nitrobenzyl (1S,5R,6S)-2-[5-chloro-7-(pyridin-3-yl)carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.65 ppm): 0.97 (3H, d, J=7.1 Hz), 1.19 (3H, d, J=6.4 Hz), 3.26–3.37 (2H, m), 4.07–4.17 (2H, m), 7.20 (1H, m), 7.57 (1H, s), 8.08 (1H, m), 8.37 (1H, m), 8.73 (1H, m)

Example 50

(1S,5R,6S)-2-[5-Chloro-7-(1-carbamoylmethylpyridinium-3-yl)carbonylimidazo[5,1-b]thiazol-2-yl]-6-((1R)-1-hydroxyethyl)-1-methyl-1-carbapen-2-em-3-carboxylate (intramolecular salt) (Compound No. 102)

The title compound (76 mg) was prepared in the same manner as in steps a) and b) of Example 2, except that 185 mg of 4-nitrobenzyl (1S,5R,6S)-2-[5-chloro-7-(pyridin-3-yl)carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.65 ppm): 0.89 (3H, d, J=6.5 Hz), 1.13 (3H, d, J=6.1 Hz), 3.05–3.23 (2H, m), 3.91 (1H, m), 4.05 (1H, m), 5.39 (2H, s), 7.42 (1H, s), 7.82 (1H, m), 8.66 (1H, m), 8.91 (1H, m), 9.14 (1H, s)

Example 51

(1S,5R,6S)-2-[7-(1-Carboxymethylpyridium-3-yl)carbonyl-5-phenylimidazo[5,1-b]thiazol-2-yl]-6-((1R)-1-hydroxyethyl)-1-methyl-1-carbapen-2-em-3-carboxylate (intramolecular salt) (Compound No. 104)

The title compound (47.0 mg) was synthesized in substantially the same manner as in steps a) and b) of Example 4, except that 130 mg of 4-nitrobenzyl (1S,5R,6S)-6-((1R)-1-hydroxyethyl)-1-methyl-2-[5-phenyl-7-(pyridin-3-yl)carbonylimidazo[5,1-b]thiazol-2-yl]-1-carbapen-2-em-3-carboxylate and 4-nitrobenzyl hydroxyacetate were used as the starting compounds.

NMR (DMSO-d$_6$) δ: 1.06 (3H, d, J=7.1 Hz), 1.16 (3H, d, J=6.3 Hz), 3.11 (1H, dd, J$_1$=6.6 Hz, J$_2$=2.4 Hz), 3.65 (1H, m), 3.94 (1H, m), 4.00 (1H, dd, J$_1$=9.5 Hz, J$_2$=2.7 Hz), 5.04 (1H, d, J=5.4 Hz), 5.64 (1H, d, J=15.8 Hz), 5.81 (1H, d, J=15.8 Hz), 7.49–7.58 (3H, m), 7.77 (1H, br s), 8.03 (2H, d, J=8.6 Hz), 8.30 (1H, s), 8.35 (1H, m), 8.44 (1H, br s), 9.14 (1H, d, J=6.1 Hz), 9.54 (1H, d, J=8.3 Hz), 9.95 (1H, s)

Example 52

Sodium (1S,5R,6S)-2-[5-(4-dimethylaminophenyl)-7-(pyridin-3-yl)carbonylimidazo[5,1-b]thiazol-2-yl]-6-((1R)-1-hydroxyethyl)-1-methyl-1-carbapen-2-em-3-carboxylate (Compound No. 105)

4-Nitrobenzyl (1S,5R,6S)-2-[5-(4-dimethylaminophenyl)-7-(pyridin-3-yl)carbonylimidazo[5,1-b]thiazol-2-yl]-6-((1R)-1-hydroxyethyl)-1-methyl-1-carbapen-2-em-3-carboxylate was synthesized in substantially the same manner as in Example 1, except that 486 mg of 4-nitrobenzyl (1R,3R,5R,6S)-6-((1R)-1-hydroxyethyl)-1-methyl-2-oxo-1-carbapenam-3-carboxylate and 348 mg of 5(4-dimethylaminophenyl)-7-(pyridin-3-yl)carbonyl-2-(tri-n-butylstannyl)imidazo[5,1-b]thiazole were used as the starting compounds. The title compound (44.0 mg) was synthesized from 104 mg of this compound.

NMR (DMSO-d$_6$) δ: 1.07 (3H, d, J=7.0 Hz), 1.11 (3H, d, J=6.4 Hz), 2.94 (6H, s), 3.09 (1H, dd, J$_1$=6.6 Hz, J$_2$=2.4 Hz), 3.59 (1H, m), 3.88 (1H, m), 4.01 (1H, dd, J$_1$=9.5 Hz, J$_2$=2.7 Hz), 4.96 (1H, d, J=5.6 Hz), 6.80 (2H, d, J=9.0 Hz), 7.57 (1H, m), 7.75 (2H, d, J=8.8 Hz), 8.34 (1H, m), 8.70–8.72 (2H, m), 9.59 (1H, s)

Example 53

(1S,5R,6S)-2-[7-(1-Carbamoylmethylpyridium-3-yl)carbonyl-5-(4-dimethylaminophenyl)imidazo[5,1-b]-thiazol-2-yl]-6-((1R)-1-hydroxyethyl)-1-methyl-1-carbapen-2-em-3-carboxylate (intramolecular salt) (Compound No. 106)

The title compound (35.0 mg) was synthesized in substantially the same manner as in Example 2, except that 138 mg of 4-nitrobenzyl (1S,5R,6S)-2-[5-(4-dimethylaminophenyl)-7-(pyridin-3-yl)carbonylimidazo[5,1-b]thiazol-2-yl]-6-((1R)-1-hydroxyethyl)-1-methyl-1-carbapen-2-em-3-carboxylate was used as the starting compound.

NMR (DMSO-d$_6$) δ: 1.05 (3H, d, J=7.0 Hz), 1.17 (3H, d, J=6.4 Hz), 3.01 (6H, s), 3.11 (1H, dd, J$_1$=6.6 Hz, J$_2$=2.7 Hz), 3.59 (1H, m), 3.92 (1H, m), 3.99 (1H, m), 5.02 (1H, d, J=5.4 Hz), 5.63 (1H, d, J=15.4 Hz), 5.86 (1H, d, J=15.4 Hz), 6.82 (2H, s), 7.78 (1H, br s), 7.81 (2H, d, J=8.8 Hz), 8.32 (1H, s), 8.53 (1H, br s), 9.13 (1H, d, J=6.1 Hz), 9.48 (1H, d, J=8.3 Hz), 9.98 (1H, s)

Example 54

(1S,5R,6S)-2-[7-[1-(3-Aminopropyl)piperidin-4-yl]carbonylimidazo[5,1-b]thiazol-2-yl]-6-((1R)-1-hydroxyethyl)-1-methyl-1-carbapen-2-em-3-carboxylic acid (hydrochloride) (Compound No. 109)

a) 4-Nitrobenzyl (1S,5R,6S)-2-[7-[1-(3-azidopropyl)piperidin-4-yl]carbonylimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[7-[1-(3-azidopropyl)piperidin-4-yl]carbonylimidazo[5,1-b]thiazol-2-yl]-6-((1R)-1-hydroxyethyl)-1-methyl-1-carbapen-2-em-3-carboxylate (862 mg) was prepared in the same manner as in step a) of Example 1, except that 658 mg of 4-nitrobenzyl (1R,3R,5R,6S)-6-((1R)-1-hydroxyethyl)-1-methyl-2-oxo-1-carbapenam-3-carboxylate and 1.16 g of 7-[1-(3-azidopropyl)piperidin-4-yl]carbonyl-2-(tri-n-butylstannyl)imidazo[5,1-b]thiazole were used as the starting compounds.

NMR (CDCl$_3$) δ: 1.30 (3H, d, J=6.3 Hz), 1.40 (3H, d, J=6.4 Hz), 1.78–2.02 (6H, m), 2.14 (2H, m), 2.45 (2H, t, J=7.1 Hz), 2.99 (2H, m), 3.35 (2H, t, J=6.9 Hz), 3.37–3.56 (3H, m), 4.32 (1H, m), 4.41 (1H, dd, J$_1$=9.8 Hz, J$_2$=2.7 Hz), 5.27 (1H, d, J=13.6 Hz), 5.51 (1H, d, J=13.6 Hz), 7.67 (2H, d, J=8.7 Hz), 8.00 (1H, s), 8.24 (2H, d, J=8.7 Hz), 8.51 (1H, s)

b) (1S,5R,6S)-2-[7-[1-(3-Aminopropyl)piperidin-4-yl]carbonylimidazo[5,1-b]thiazol-2-yl]-6-((1R)-1-hydroxyethyl)-1-methyl-1-carbapen-2-em-3-carboxylic acid (hydrochloride)

The title compound (94 mg) was prepared in the same manner as in step b) of Example 1, except that 862 mg of 4-nitrobenzyl (1S,5R,6S)-2-[7-[1-(3-azidopropyl)piperidin-4-yl]carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.80 ppm): 1.11 (3H, d, J=7.0 Hz), 1.19 (3H, d, J=6.3 Hz), 1.79 (2H, m), 2.06 (4H, m), 2.95–3.20 (6H, m), 3.36–3.65 (5H, m), 4.15 (1H, m), 4.20 (1H, dd, J$_1$=9.3 Hz, J$_2$=2.7 Hz), 7.86 (1H, s), 7.96 (1H, s)

Example 55

Sodium (1S,5R,6S)-6-((1R)-1-hydroxyethyl)-1-methyl-2-[5-methylthio-7-(pyridin-3-yl)carbonylimidazo[5,1-b]thiazol-2-yl]-1-carbapen-2-em-3-carboxylate (Compound No. 110)

a) 4-Nitrobenzyl (1S,5R,6S)-6-((1R)-1-hydroxyethyl)-1-methyl-2-[5-methylthio-7-(pyridin-3-yl)carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[5-methylthio-7-(pyridin-3-yl)carbonylimidazo[5,1-b]thiazol-2-yl]-1-carbapen-2-em-3-carboxylate (1.78 g) was prepared in the same manner as in step a) of Example 1, except that 1.10 g of 4-nitrobenzyl (1R,3R,5R,6S)-6-((1R)-1-hydroxyethyl)-1-methyl-2-oxo-1-carbapenam-3-carboxylate and 1.88 g of 5-methylthio-7-(pyridin-3-yl)carbonyl-2-(tri-n-butylstannyl)imidazo[5,1-b]thiazole were used as the starting compounds.

NMR (CDCl$_3$) δ: 1.34 (3H, d, J=7.3 Hz), 1.41 (3H, d, J=6.1 Hz), 2.75 (3H, s), 3.40 (1H, dd, J$_1$=6.5 Hz, J$_2$=2.8 Hz), 3.57 (1H, m), 4.33 (1H, m), 4.43 (1H, dd, J$_1$=9.7 Hz, J$_2$=2.8 Hz), 5.30 (1H, d, J=13.4 Hz), 5.56 (1H, d, J=13.4 Hz), 7.46 (1H, m), 7.69 (2H, d, J=8.8 Hz), 8.25 (2H, d, J=8.8 Hz), 8.33 (1H, s), 8.76–8.84 (2H, m), 9.83 (1H, m)

b) Sodium (1S,5R,6S)-6-((1R)-1-hydroxyethyl)-1-methyl-2-[5-methylthio-7-(pyridin-3-yl)carbonylimidazo[5,1-b]-thiazol-2-yl]-1-carbapen-2-em-3-carboxylate The title compound (37 mg) was prepared in the same manner as in step b) of Example 1, except that 108 mg of 4-nitrobenzyl (1S,5R,6S)-6-((1R)-1-hydroxyethyl)-1-methyl-2-[5-methylthio-7-(pyridin-3-yl)carbonylimidazo[5,1-b]thiazol-2-yl]-1-carbapen-2-em-3-carboxylate was used as the starting compound.

NMR (D$_2$O) δ (HOD=4.65 ppm): 0.99 (3H, d, J=7.0 Hz), 1.21 (3H, d, J=6.1 Hz), 2.42 (3H, s), 3.28–3.39 (2H, m), 4.10–4.19 (2H, m), 7.25 (1H, m), 7.56 (1H, s), 8.23 (1H, m), 8.37 (1H, m), 8.87 (1H, m)

Example 56

(1S,5R,6S)-2-[7-(1-Carbamoylmethylpyridinium-3-yl)carbonyl-5-methylthioimidazo[5,1-b]-thiazol-2-yl]-6-((1R)-1-hydroxyethyl)-1-methyl-1-carbapen-2-em-3-carboxylate (intramolecular salt) (Compound No. 114)

The title compound (9 mg) was prepared in the same manner as in steps a) and b) of Example 2, except that 162 mg of 4-nitrobenzyl (1S,5R,6S)-6-((1R)-1-hydroxyethyl)-1-methyl-2-[5-methylthio-7-(pyridin-3-yl)carbonylimidazo[5,1-b]thiazol-2-yl]-1-carbapen-2-em-3-carboxylate was used as the starting compound.

NMR (DMSO-d$_6$) δ: 1.13 (3H, d, J=6.8 Hz), 1.19 (3H, d, J=6.1 Hz), 2.67 (3H, s), 3.15 (1H, dd, J$_1$=6.8 Hz, J$_2$=2.7 Hz), 3.66 (1H, m), 3.97 (1H, m), 4.10 (1H, dd, J$_1$=9.3 Hz, J$_2$=2.7 Hz), 5.07 (1H, d, J=5.1 Hz), 5.60 (1H, d, J=15.7 Hz), 5.83 (1H, d, J=15.7 Hz), 7.20 (1H, s), 7.74 (1H, s), 8.34 (1H, m), 8.45 (1H, s), 9.14 (1H, m), 9.50 (1H, m), 9.87 (1H, s)

Example 57

Sodium (1S,5R,6S)-2-[5-formyl-7-(pyridin-3-yl)carbonylimidazo[5,1-b]thiazol-2-yl]-6-((1R)-1-hydroxyethyl)-1-methyl-1-carbapen-2-em-3-carboxylate (Compound No. 117)

a) 4-Nitrobenzyl (1S,5R,6S)-2-[5-formyl-7-(pyridin-3-yl)carbonylimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[5-formyl-7-(pyridin-3-yl)carbonylimidazo[5,1-b]thiazol-2-yl]-6-((1R)-1-hydroxyethyl)-1-methyl-1-carbapen-2-em-3-carboxylate (1.12 g) was prepared in the same manner as in step a) of Example 1, except that 1.04 g of 4-nitrobenzyl (1R,3R,5R,6S)-6-((1R)-1-hydroxyethyl)-1-methyl-2-oxo-1-carbapenam-3-carboxylate and 1.56 g of 5-formyl-7-(pyridin-3-yl)carbonyl-2-(tri-n-butylstannyl)imidazo[5,1-b]thiazole were used as the starting compounds.

NMR (CDCl$_3$) δ: 1.37 (3H, d, J=7.3 Hz), 1.41 (3H, d, J=6.3 Hz), 3.42 (1H, dd, J$_1$=6.4 Hz, J$_2$=3.0 Hz), 3.69 (1H, m), 4.34 (1H, m), 4.45 (1H, dd, J$_1$=9.7 Hz, J$_2$ =2.9 Hz), 5.33 (1H, d, J=13.4 Hz), 5.57 (1H, d, J=13.4 Hz), 7.51 (1H, m), 7.69 (2H, d, J=8.8 Hz), 8.25 (2H, d, J=8.7 Hz), 8.82–8.89 (2H, m), 8.92 (1H, s), 9.83 (1H, m), 9.88 (1H, s)

b) Sodium (1S,5R,6S)-2-[5-formyl-7-(pyridin-3-yl)carbonylimidazo[5,1-b]thiazol-2-yl]-6-((1R)-1-hydroxyethyl)-1-methyl-1-carbapen-2-em-3-carboxylate The title compound (54 mg) was prepared in the same manner as in step b) of Example 1, except that 209 mg of 4-nitrobenzyl (1S,5R,6S)-2-[5-formyl-7-(pyridin-3-yl) carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.65 ppm): 1.01 (3H, d, J=7.1 Hz), 1.21 (3H, d, J=6.3 Hz), 3.30–3.45 (2H, m), 4.10–4.19 (2H, m), 7.34 (1H, m), 8.12 (1H, S), 8.31 (1H, m), 8.48 (1H, m), 8.98 (1H, s), 9.40 (1H, s)

Example 58

(1S,5R,6S)-2-[7-[1-(3-Aminopropyl)-5-carboxypyridinium-3-yl]carbonylimidazo[5,1-b] thiazol-2-yl]-6-((1R)-1-hydroxyethyl)-1-methyl-1-carbapen-2-em-3-carboxylate (intramolecular salt, hydrochloride) (Compound No. 123)

a) 4-Nitrobenzyl (1S,5R,6S)-6-((1R)-1-hydroxyethyl)-1-methyl-2-[7-[5-(4-nitrobenzyloxycarbonyl)pyridin-3-yl]-carbonylimidazo[5,1-b]thiazol-2-yl]-1-carbapen-2-em-3-carboxylate 4-Nitrobenzyl (1S,5R,6S)-6-((1R)-1-hydroxyethyl)-1-methyl-2-[7-[5-(4-nitrobenzyloxycarbonyl)pyridin-3-yl] carbonylimidazo[5,1-b]thiazol-2-yl]-1-carbapen-2-em-3-carboxylate (97.2 mg) was prepared in the same manner as in step a) of Example 1, except that 98 mg of 4-nitrobenzyl (1R,3R,5R,6S)-6-((1R)-1-hydroxyethyl)-1-methyl-2-oxo-1-carbapenam-3-carboxylate and 198 mg of 7-[5-(4-nitrobenzyloxycarbonyl)pyridin-3-yl]carbonyl-2-(tri-n-butylstannyl)imidazo[5,1-b]thiazole were used as the starting compounds.

NMR (CDCl$_3$) δ: 1.34 (3H, d, J=7.2 Hz), 1.41 (3H, d, J=6.3 Hz), 3.41 (1H, dd, J$_1$=6.3 Hz, J$_2$=2.7 Hz), 3.5–3.65 (1H, m), 4.25–4.4 (1H, m), 4.44 (1H, dd, J$_1$=9.6 Hz, J$_2$=2.7 Hz), 5.29 (1H, d, J=13.5 Hz), 5.54 (1H, d, J=13.5 Hz), 5.54 (2H, s), 7.6–7.75 (4H, m), 8.11 (1H, s), 8.2–8.3 (4H, m), 8.57 (1H, m), 9.4–9.5 (2H, m), 9.9–9.95 (1H, m)

b) (1S,5R,6S)-2-[7-[1-(3-Aminopropyl)-5-carboxypyridinium-3-yl]carbonylimidazo[5,1-b]thiazol-2-yl]-6-((1R)-1-hydroxyethyl)-1-methyl-1-carbapen-2-em-3-carboxylate (intramolecular salt, hydrochloride)

The title compound (11.5 mg) was prepared in the same manner as in steps a) and b) of Example 4, except that 97.2 mg of 4-nitrobenzyl (1S,5R,6S)-6-((1R)-1-hydroxyethyl)-1-methyl-2-[7-[5-(4-nitrobenzyloxycarbonyl)pyridin-3-yl] carbonylimidazo[5,1-b]thiazol-2-yl]-1-carbapen-2-em-3-carboxylate and 27.0 mg of 3-azido-1-propanol were used as the starting compounds.

NMR (D$_2$O) δ (HOD=4.80 ppm): 1.07 (3H, d, J=7.5 Hz), 1.26 (3H, d, J=6.3 Hz), 2.5–2.7 (2H, m), 3.2–3.4 (4H, m), 4.0–4.3 (2H, m), 4.8–5.0 (2H, m), 7.82 (1H, s), 7.98 (1H, s), 9.15 (1H, s), 9.22 (1H, s), 9.69 (1H, s)

Example 59

Sodium (1S,5R,6S)-2-[5-acetyl-7-(pyridin-3-yl) carbonylimidazo[5,1-b]thiazol-2-yl]-6-((1R)-1-hydroxyethyl)-1-methyl-1-carbapen-2-em-3-carboxylate (Compound No. 125)

a) 4-Nitrobenzyl (1S,5R,6S)-2-[5-acetyl-7-(pyridin-3-yl) carbonylimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[5-acetyl-7-(pyridin-3-yl) carbonylimidazo[5,1-b]thiazol-2-yl]-6-((1R)-1-hydroxyethyl)-1-methyl-1-carbapen-2-em-3-carboxylate (112 mg) was prepared in the same manner as in step a) of Example 1, except that 269 mg of 4-nitrobenzyl (1R,3R,5R, 6S)-6-((1R)-1-hydroxyethyl)-1-methyl-2-oxo-1-carbapenam-3-carboxylate and 437 mg of 5-acetyl-7 (pyridin-3-yl)carbonyl-2-(tri-n-butylstannyl)imidazo-[5,1-b]thiazole were used as the starting compounds.

NMR (DMSO-d$_6$) δ: 1.15–1.25 (6H, m), 2.68 (3H, s), 3.45–3.5 (1H, m), 3.8–3.95 (1H, m), 4.0–4.1 (1H, m), 4.35–4.4 (1H, m), 5.38 (1H, d, J=13.8 Hz), 5.51 (1H, d, J=13.8 Hz), 7.6–7.75 (3H, m), 8.17 (2H, d, J=8.7 Hz), 8.75–8.9 (3H, m), 9.6–9.65 (1H, m)

b) Sodium (1S,5R,6S)-2-[5-acetyl-7-(pyridin-3-yl)-carbonylimidazo[5,1-b]thiazol-2-yl]-6-((1R)-1-hydroxyethyl)-1-methyl-1-carbapen-2-em-3-carboxylate The title compound (18.8 mg) was prepared in the same manner as in step b) of Example 1, except that 112 mg of 4-nitrobenzyl (1S,5R,6S)-2-[5-acetyl-7-(pyridin-3-yl) carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.80 ppm): 1.01 (3H, d, J=6.9 Hz), 1.34 (3H, d, J=6.3 Hz), 2.33 (3H, s), 3.2–3.4 (2H, m), 4.1–4.3 (2H, m), 7.25–7.35 (1H, m), 7.88 (1H, s), 8.25–8.3 (1H, m), 8.45–8.5 (1H, m), 8.98 (1H, s)

Example 60

(1S,5R,6S)-2-[5-Acetyl-7-(1-carbamoylmethylpyridinium-3-yl)carbonylimidazo [5,1-b]thiazol-2-yl]-6-((1R)-1-hydroxyethyl)-1-methyl-1-carbapen-2-em-3-carboxylate (intramolecular salt) (Compound No. 126)

The title compound (1.5 mg) was prepared in the same manner as in steps a) and b) of Example 2, except that 52.1 mg of 4-nitrobenzyl (1S,5R,6S)-2-[5-acetyl-7-(pyridin-3-yl) carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.80 ppm): 1.00 (3H, d, J=6.9 Hz), 1.31 (3H, d, J=6.6 Hz), 2.47 (3H, s), 3.2–3.4 (2H, m), 4.0–4.3 (2H, m), 5.66 (2H, s), 7.94 (1H, s), 8.15–8.25 (1H, m), 8.9–9.0 (1H, m), 9.3–9.4 (1H, m), 9.52 (1H, s)

Example 61

(1S,5R,6S)-6-((1R)-1-Hydroxyethyl)-1-methyl-2-[5-methylthio-7-[1-(3-sulfamoylaminopropyl) pyridinium-3-yl]carbonylimidazo[5,1-b]thiazol-2-yl]-1-carbapen-2-em-3-carboxylate (intramolecular salt) (Compound No. 132)

The title compound (41 mg) was prepared in the same manner as in steps a) and b) of Example 4, except that 222 mg of 4-nitrobenzyl (1S,5R,6S)-6-((1R)-1-hydroxyethyl)-1-methyl-2-[5-methylthio-7-(pyridin-3-yl)carbonylimidazo[5, 1-b]thiazol-2-yl]-1-carbapen-2-em-3-carboxylate and 166 mg of 3-(4-nitrobenzyloxycarbonylaminosulfonyl) aminopropanol were used as the starting compounds.

NMR (D$_2$O) δ (HOD=4.65 ppm): 1.00 (3H, d, J=7.1 Hz), 1.18 (3H, d, J=6.3 Hz), 2.14–2.27 (4H, m), 3.09 (2H, t, J=6.3 Hz), 3.23–3.35 (2H, m), 4.04 (1H, m), 4.13 (1H, m), 4.65 (2H, m), 7.49 (1H, s), 7.96 (1H, m), 8.83 (1H, m), 8.91 (1H, m), 9.51 (1H, s)

Example 62

(1S,5R,6S)-2-[5-Chloro-7-[1-(3-sulfamoylaminopropyl)pyridinium-3-yl] carbonylimidazo[5,1-b]thiazol-2-yl]-6-((1R)-1-hydroxyethyl)-1-methyl-1-carbapen-2-em-3-carboxylate (intramolecular salt) (Compound No. 133)

The title compound (64 mg) was prepared in the same manner as in steps a) and b) of Example 4, except that 218 mg of 4-nitrobenzyl (1S,5R,6S)-2-[5-chloro-7-(pyridin-3-yl)carbonylimidazo[5,1-b]thiazol-2-yl]-6-((1R)-1-hydroxyethyl)-1-methyl-1-carbapen-2-em-3-carboxylate and 160 mg of 3-(4-nitrobenzyloxycarbonylaminosulfonyl)aminopropanol were used as the starting compounds.

NMR (D$_2$O) δ (HOD=4.65 ppm): 1.07 (3H, d, J=7.1 Hz), 1.19 (3H, d, J=6.3 Hz), 2.24 (2H, m), 3.09 (2H, t, J=6.3 Hz), 3.29–3.41 (2H, m), 4.05–4.17 (2H, m), 4.72 (2H, m), 7.71 (1H, s), 7.99 (1H, m), 8.88 (1H, m), 9.00 (1H, m), 9.41 (1H, s)

Example 63

(1S,5R,6S)-2-[7-(1-Carboxymethylpyridium-3-yl)carbonyl-5-phenylimidazo[5,1-b]thiazol-2-yl]-6-((1R)-1-hydroxyethyl)-1-methyl-1-carbapen-2-em-3-carboxylate (intramolecular salt) (Compound No. 134)

The title compound (19.0 mg) was synthesized in substantially the same manner as in Example 4, except that 115 mg of nitrobenzyl (1S,5R,6S)-6-((1R)-1-hydroxyethyl)-1-methyl-2-[5-phenyl-7-(pyridin-3-yl)carbonylimidazo[5,1-b]thiazol-2-yl]-1-carbapen-2-em-3-carboxylate and 4-nitrobenzyl hydroxyacetate were used as the starting compounds.

NMR (DMSO-d6) δ: 1.12 (3H, d, J=6.8 Hz), 1.17 (3H, d, J=6.1 Hz), 3.14 (1H, dd, J$_1$=6.6 Hz, J$_2$=2.4 Hz), 3.71 (1H, m), 3.94 (1H, m), 4.07 (1H, dd, J$_1$=9.3 Hz, J$_2$=2.7 Hz), 5.01 (1H, d, J=5.4 Hz), 5.05 (2H, s), 7.51–7.59 (3H, m), 8.05 (2H, d, J=6.8 Hz), 8.23 (1H, m), 8.44 (1H, s), 9.00 (1H, d, J=6.1 Hz), 9.51 (1H, d, J=8.3 Hz), 9.70 (1H, s)

Example 64

(1S,5R,6S)-2-[5-Carbamoyl-7-(1-carbamoylmethylpyridinium-3-yl)carbonylimidazo[5,1-b]thiazol-2-yl]-6-((1R)-1-hydroxyethyl)-1-methyl-1-carbapen-2-em-3-carboxylate (intramolecular salt) (Compound No. 143)

a) 4-Nitrobenzyl (1S,5R,6S)-2-[5-carbamoyl-7-(pyridin-3-yl)carbonylimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[5-carbamoyl-7-(pyridin-3-yl)carbonylimidazo[5,1-b]thiazol-2-yl]-6-((1R)-1-hydroxyethyl)-1-methyl-1-carbapen-2-em-3-carboxylate (239 mg) was prepared in the same manner as in step a) of Example 1, except that 210 mg of 4-nitrobenzyl (1R,3R,5R,6S)-6-((1R)-1-hydroxyethyl)-1-methyl-2-oxo-1-carbapenam-3-carboxylate and 342 mg of 5-carbamoyl-7-(pyridin-3-yl)carbonyl-2-(tri-n-butylstannyl)imidazo[5,1-b]thiazole were used as the starting compounds.

NMR (DMSO-d$_6$) δ: 1.15–1.25 (6H, m), 3.45–3.5 (1H, m), 3.8–3.9 (1H, m), 4.0–4.1 (1H, m), 4.35–4.4 (1H, m), 5.16 (1H, d, J=4.8 Hz), 5.40 (1H, d, J=13.5 Hz), 5.53 (1H, d, J=13.5 Hz), 7.55–7.65 (1H, m), 7.72 (2H, d, J=9.0 Hz), 7.86 (1H, br s), 8.19 (2H, d, J=9.0 Hz), 8.34 (1H, br s), 8.8–8.85 (1H, m), 8.95–9.0 (1H, m), 9.65–9.7 (1H, m)

b) (1S,5R,6S)-2-[5-Carbamoyl-7-(1-carbamoylmethylpyridinium-3-yl)carbonylimidazo[5,1-b]thiazol-2-yl]-6-((1R)-1-hydroxyethyl)-1-methyl-1-carbapen-2-em-3-carboxylate (intramolecular salt)

The title compound (8.6 mg) was prepared in the same manner as in steps a) and b) of Example 2, except that 95 mg of 4-nitrobenzyl (1S,5R,6S)-2-[5-carbamoyl-7-(pyridin-3-yl)carbonylimidazo[5,1-b]thiazol-2-yl]-6-((1R)-1-hydroxyethyl)-1-methyl-1-carbapen-2-em-3-carboxylate was used as the starting compound.

NMR (D$_2$O) δ (HOD=4.80 ppm): 0.9–1.1 (3H, m), 1.25–1.35 (3H, m), 3.2–3.4 (2H, m), 4.0–4.3 (2H, m), 5.6–5.8 (2H, m), 7.7–7.8 (1H, m), 8.0–8.2 (1H, m), 8.8–9.0 (1H, m), 9.2–9.4 (2H, m), 9.4–9.5 (1H, m)

Example 65

(1S,5R,6S)-6-((1R)-1-Hydroxyethyl)-1-methyl-2-[7-[1-(2-sulfamoylaminoethyl)pyridinium-3-yl]]carbonylimidazo[5,1-b]thiazol-2-yl]-1-carbapen-2-em-3-carboxylate (intramolecular salt) (Compound No. 148)

The title compound (101 mg) was prepared in the same manner as in steps a) and b) of Example 4, except that 572 mg of 2-(4-nitrobenzyloxycarbonylaminosulfonyl)aminoethanol was used instead of 3-azido-1-propanol in step a) of Example 4 and 585 mg of 4-nitrobenzyl (1S,5R,6S)-6-((1R)-1-hydroxyethyl)-1-methyl-2-[7-(pyridin-3-yl)carbonylimidazo[5,1-b]thiazol-2-yl]-1-carbapen-2-em-3-carboxylate was used as the starting compound.

NMR (DMSO-d$_6$) δ: 1.14–1.21 (6H, m), 3.16 (1H, dd, J$_1$=6.0 Hz, J$_2$=2.6 Hz), 3.42–3.57 (3H, m), 3.95 (1H, m), 4.09 (1H, dd, J$_1$=9.5 Hz, J$_2$=2.7 Hz), 4.84 (2H, m), 5.07 (1H, d, J=4.2 Hz), 6.80 (2H, s), 7.29 (1H, brs), 8.27 (1H, s), 8.32 (1H, m), 8.35 (1H, s), 9.14 (1H, m), 9.52 (1H, s), 9.78 (1H, s)

Example 66

Sodium (1S,5R,6S)-2-[5-(2-aminoethyl)thio-7-(pyridin-3-yl)carbonylimidazo[5,1-b]thiazol-2-yl]-6-((1R)-1-hydroxyethyl)-1-methyl-1-carbapen-2-em-3-carboxylate (Compound No. 173)

a) 4-Nitrobenzyl (1S,5R,6S)-2-[5-(2-azidoethyl)thio-7-(pyridin-3-yl)carbonylimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[5-(2-azidoethyl)thio-7-(pyridin-3-yl)carbonylimidazo[5,1-b]thiazol-2-yl]-6-((1R)-1-hydroxyethyl)-1-methyl-1-carbapen-2-em-3-carboxylate (853 mg) was prepared in the same manner as in step a) of Example 1, except that 910 mg of 4-nitrobenzyl (1R,3R,5R,6S)-6-((1R)-1-hydroxyethyl)-1-methyl-2-oxo-1-carbapenam-3-carboxylate and 1.59 g of 5-(2-azidoethyl)thio-7-(pyridin-3-yl)carbonyl-2-(tri-n-butylstannyl)imidazo[5,1-b]thiazole were used as the starting compounds.

NMR (CDCl$_3$) δ: 1.34 (3H, d, J=7.3 Hz), 1.41 (3H, d, J=6.4 Hz), 3.35 (2H, t, J=6.5 Hz), 3.41 (1H, dd, J$_1$=6.6 Hz, J$_2$=2.7 Hz), 3.57 (1H, m), 3.68 (2H, t, J=6.5 Hz), 4.33 (1H, m), 4.43 (1H, dd, J$_1$=9.7 Hz, J$_2$=2.7 Hz), 5.31 (1H, d, J=13.4 Hz), 5.56 (1H, d, J=13.4 Hz), 7.47 (1H, m), 7.69 (2H, d, J=8.8 Hz), 8.25 (2H, d, J=8.8 Hz), 8.38 (1H, s), 8.76–8.88 (2H, m), 9.78 (1H, m)

b) Sodium (1S,5R,6S)-2-[5-(2-aminoethyl)thio-7-(pyridin-3-yl)carbonylimidazo[5,1-b]thiazol-2-yl]-6-((1R)-1-hydroxyethyl)-1-methyl-1-carbapen-2-em-3-carboxylate The title compound (42 mg) was prepared in the same manner as in step b) of Example 1, except that 110 mg of 4-nitrobenzyl (1S,5R,6S)-2-[5-(2-azidoethyl)thio-7-(pyridin-3-yl)carbonylimidazo[5,1-b]thiazol-2-yl]-6((1R)-1-hydroxyethyl)-1-methyl-1-carbapen-2-em-3-carboxylate was used as the starting compound.

NMR (D$_2$O) δ (HOD=4.65 ppm): 0.98 (3H, d, J=7.3 Hz), 1.22 (3H, d, J=6.1 Hz), 3.33–3.44 (6H, m), 4.13–4.22 (2H, m), 7.25 (1H, m), 7.70 (1H, s), 8.10 (1H, m), 8.19 (1H, m), 8.82 (1H, m)

Example 67

(1S,5R,6S)-2-[5-(2-Aminoethyl)thio-7-(1-carboxymethylpyridinium-3-yl)carbonylimidazo[5,1-b]thiazol-2-yl]-6-((1R)-1-hydroxyethyl)-1-methyl-1-carbapen-2-em-3-carboxylate (intramolecular salt) (Compound No. 169)

The title compound (63 mg) was prepared in the same manner as in steps a) and b) of Example 4, except that 220 mg of 4-nitrobenzyl (1S,5R,6S)-2-[5-(2-azidoethyl)-thio-7-(pyridin-3-yl)carbonylimidazo[5,1-b]thiazol-2-yl]-6-((1R)-1-hydroxyethyl)-1-methyl-1-carbapen-2-em-3-carboxylate and 85 mg of 4-nitrobenzyl hydroxyacetate were used as the starting compounds.
NMR (D$_2$O) δ (HOD=4.65 ppm): 1.06 (3H, d, J=7.3 Hz), 1.19 (3H, d, J=6.4 Hz), 3.32–3.46 (6H, m), 4.10–4.19 (2H, m), 5.24 (2H, s), 7.81 (1H, s), 8.00 (1H, m), 8.79 (1H, m), 8.98 (1H, m), 9.64 (1H, s)
Compound Nos. 1 to 175 have the following chemical structures.
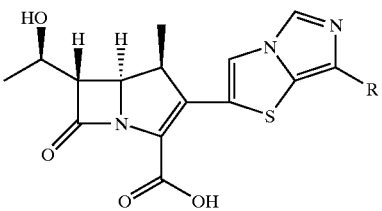
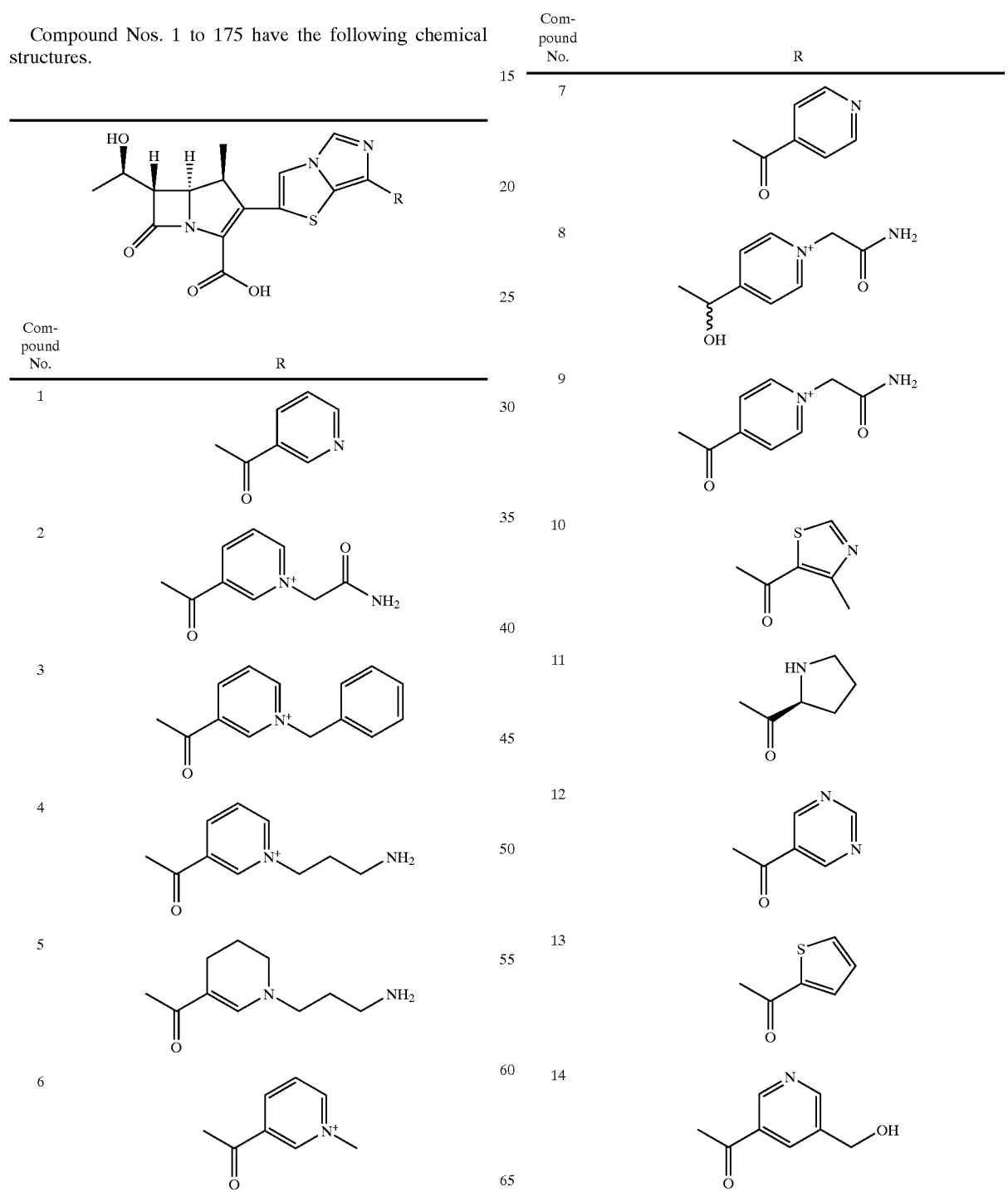

-continued
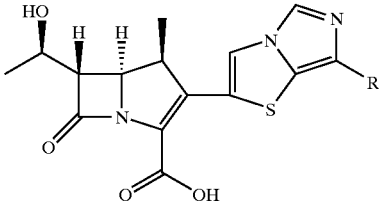
| Compound No. | R |
|---|---|
| 15 | 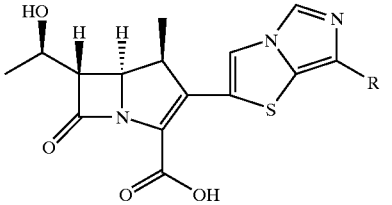 |
| 16 | 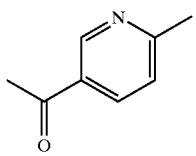 |
| 17 | 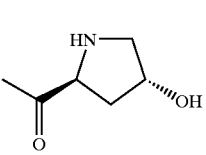 |
| 18 | 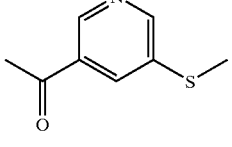 |
| 19 | 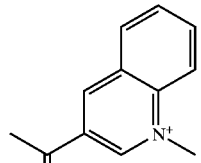 |
| 20 | 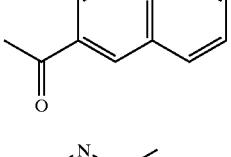 |
| 21 | 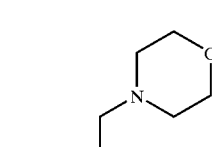 |
| 22 | 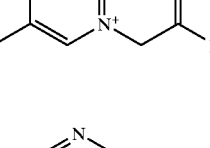 |
-continued
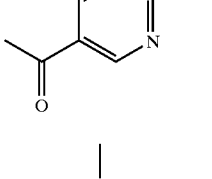
| Compound No. | R |
|---|---|
| 23 | 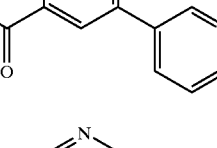 |
| 24 | 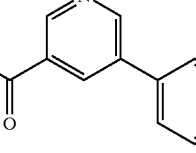 |
| 25 | 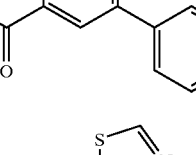 |
| 26 | 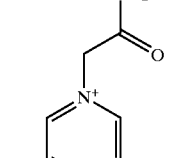 |
| 27 | 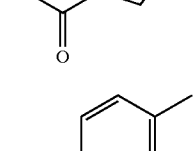 |
| 28 | 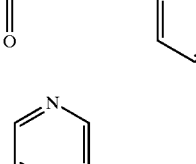 |

-continued
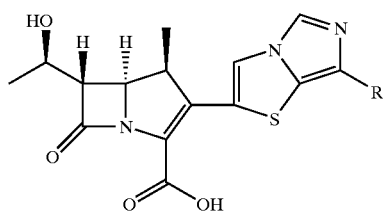
| Compound No. | R |
|---|---|
| 29 | 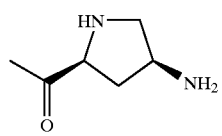 |
| 30 | 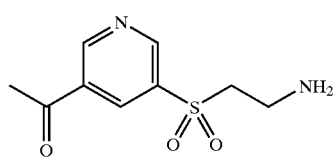 |
| 31 | 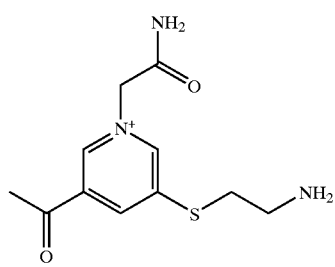 |
| 32 | 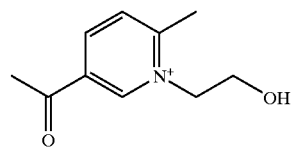 |
| 33 | 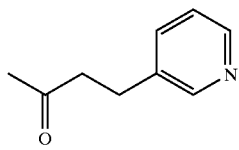 |
| 34 | 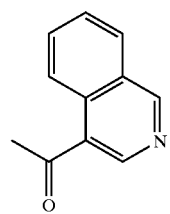 |
-continued
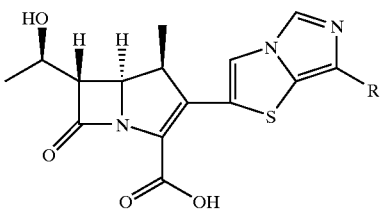
| Compound No. | R |
|---|---|
| 35 | 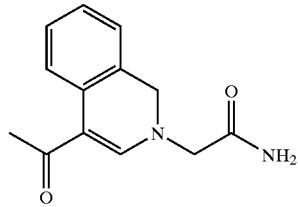 |
| 36 | 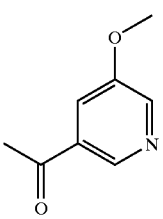 |
| 37 | 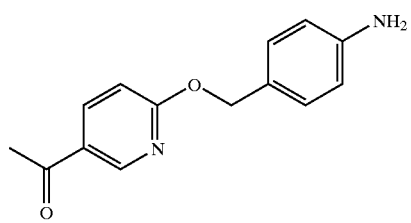 |
| 38 | 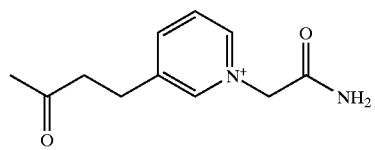 |
| 39 | 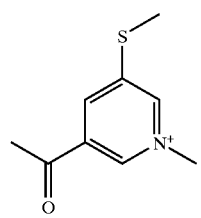 |
| 40 | 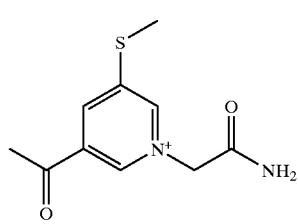 |

-continued
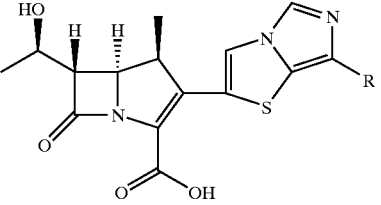
| Compound No. | R |
|---|---|
| 41 | 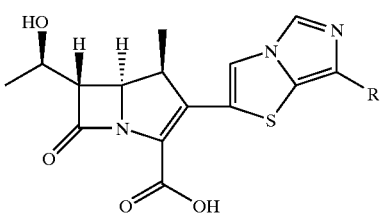 |
| 42 | 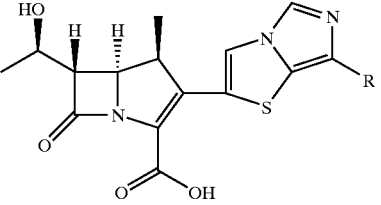 |
| 43 | 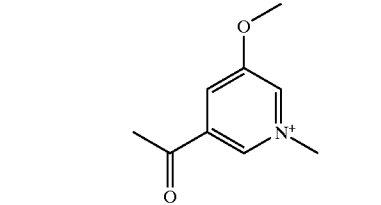 |
| 44 | 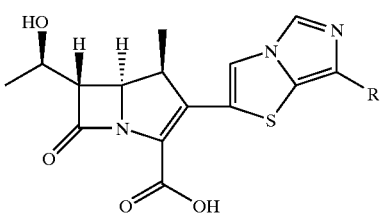 |
| 45 | 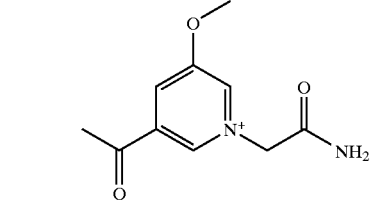 |
| 46 | 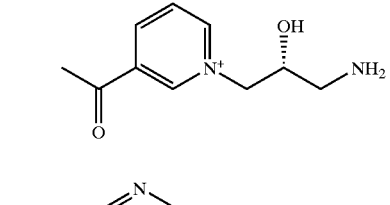 |
-continued
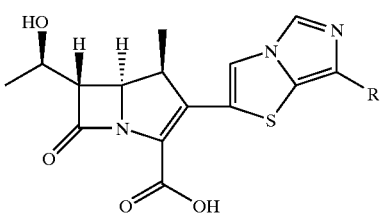
| Compound No. | R |
|---|---|
| 47 | 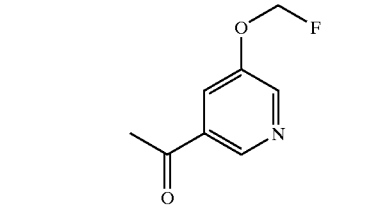 |
| 48 | 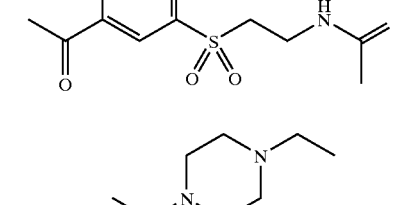 |
| 49 | 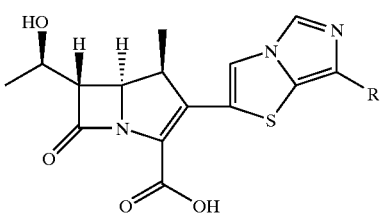 |
| 50 | 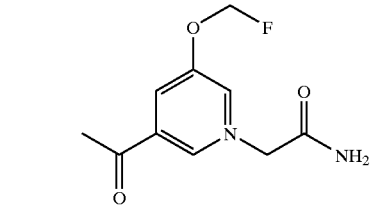 |
| 51 | 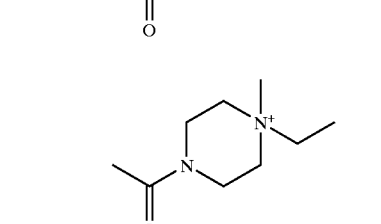 |
| 52 | 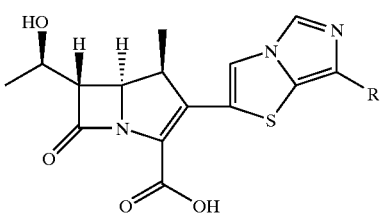 |
| 53 | 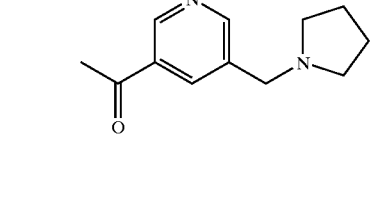 |

-continued

[Core structure: carbapenem with hydroxyethyl and methyl substituents, fused to imidazo-thiazole bearing R group]

| Compound No. | R |
|---|---|
| 54 | 3-acetyl-5-(2-aminoethylthio)-1-(carboxymethyl)pyridinium |
| 55 | 1-(2-oxopropyl)pyridinium |
| 56 | 3-acetyl-1-methyl-1H-indole |
| 57 | 1-(5-{[2-(acetimidoylamino)ethyl]thio}pyridin-3-yl)ethan-1-one |
| 61 | 2-(6,7-dihydroxyisoquinolin-2-ium-2-yl)-1-oxopropan-2-yl (2-(6,7-dihydroxyisoquinolinium)acetyl) |
| 62 | 3-acetyl-5-(methylthio)-1-(carboxymethyl)pyridinium |
| 63 | 3-acetyl-1-(carboxymethyl)pyridinium |
| 65 | 1-(1-carbamimidoylpiperidin-4-yl)ethan-1-one |
| 66 | 1-[(2S)-1-carbamimidoylpyrrolidin-2-yl]ethan-1-one |
| 67 | 1-(pyrrolidin-1-yl)propan-2-one |
| 68 | 1-{5-[(2-aminoethylthio)methyl]pyridin-3-yl}ethan-1-one |
| 69 | 3-acetyl-5-[(2-aminoethylthio)methyl]-1-(carboxymethyl)pyridinium |
| 70 | 3-acetyl-1-(2-ethoxy-2-oxoethyl)pyridinium |
| 71 | ethyl 2-(5-acetyl-3,6-dihydro-2H-pyridin-1-yl)acetate |

-continued
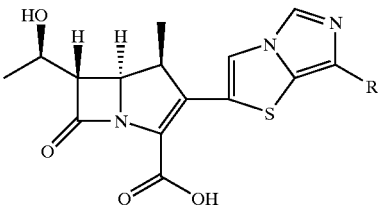
| Compound No. | R |
|---|---|
| 72 | 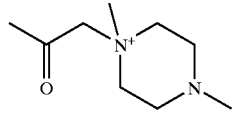 |
| 75 | 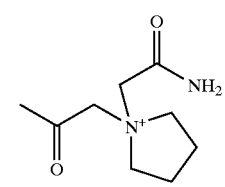 |
| 76 | 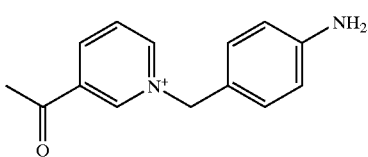 |
| 79 | 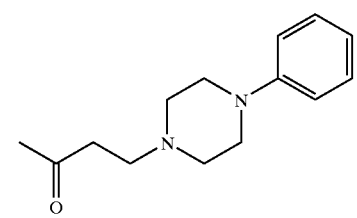 |
| 80 | 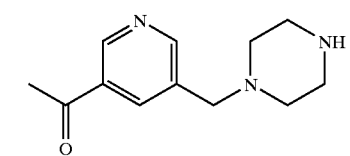 |
| 81 | 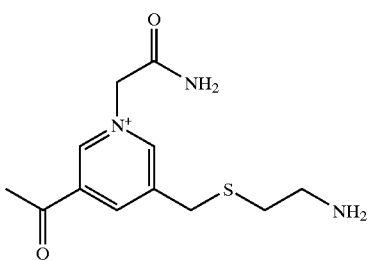 |
| 82 | 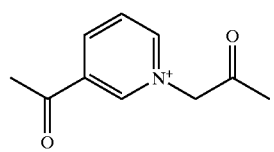 |
-continued
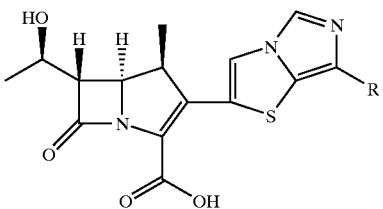
| Compound No. | R | |
|---|---|---|
| 83 | 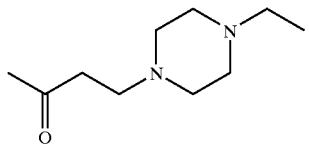 | |
| 84 | 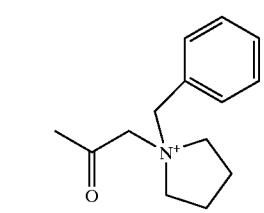 | |
| 85 | 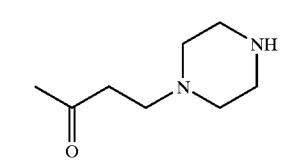 | |
| 86 | 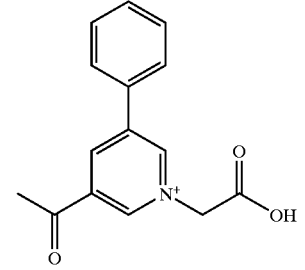 | |
| 87 | 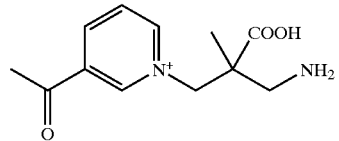 | |
| 88 | 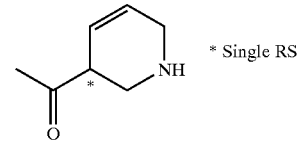 | * Single RS |
| 89 | 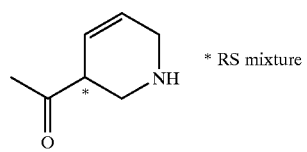 | * RS mixture |

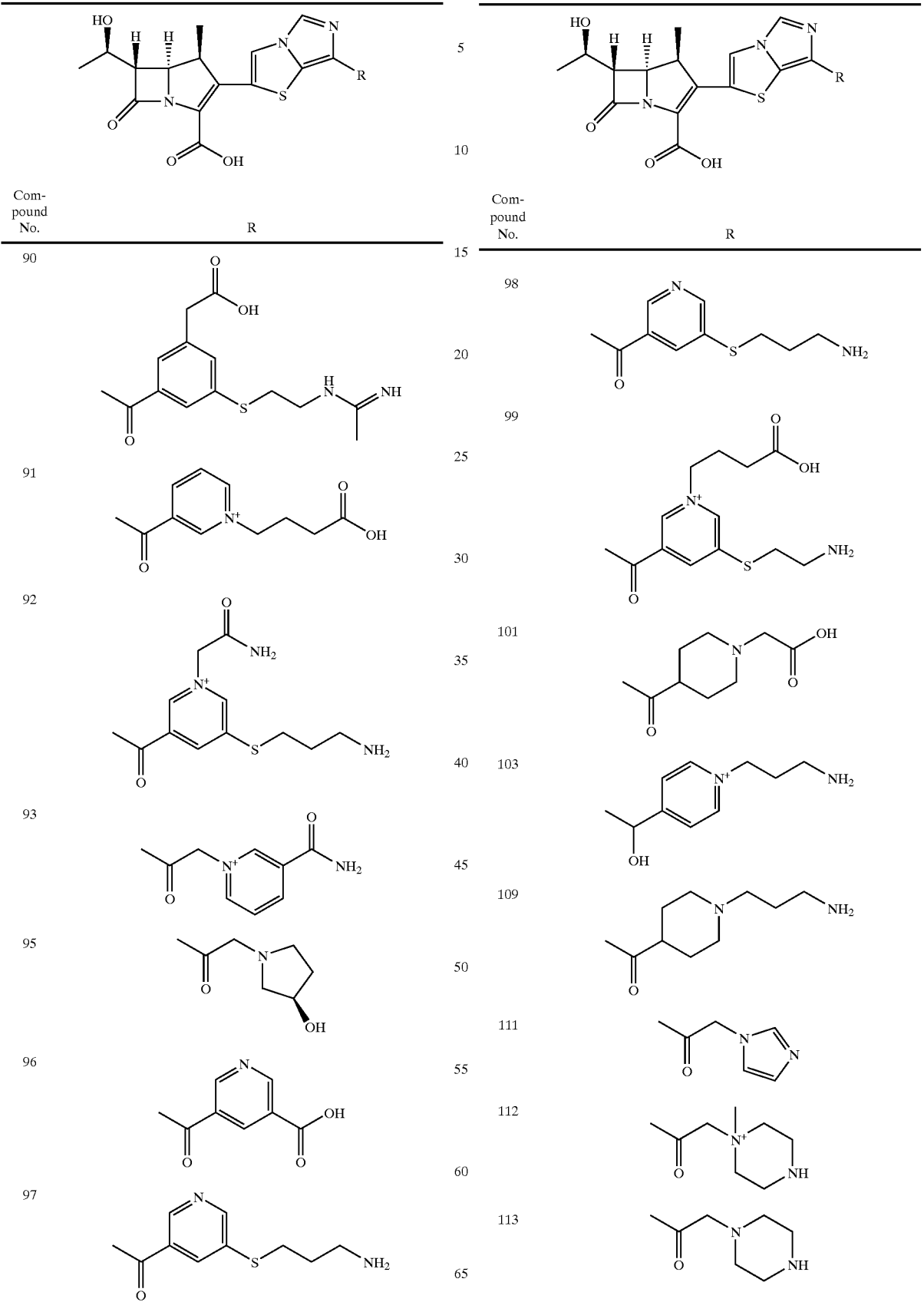

-continued
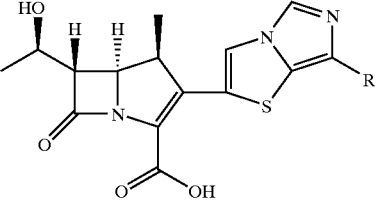
| Compound No. | R |
|---|---|
| 123 | 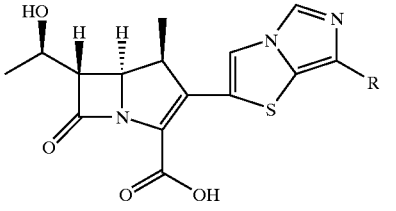 |
| 135 | 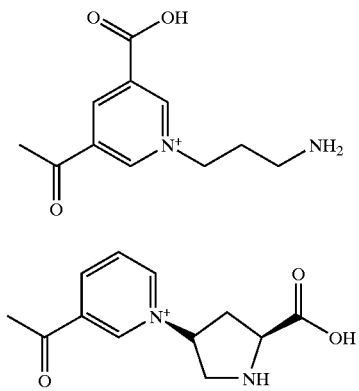 |
| 141 | 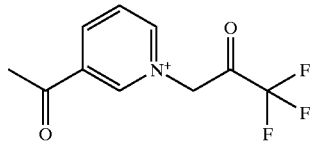 |
| 142 | 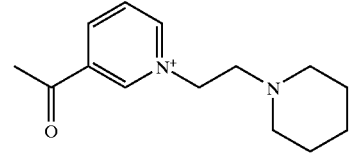 |
| 146 | 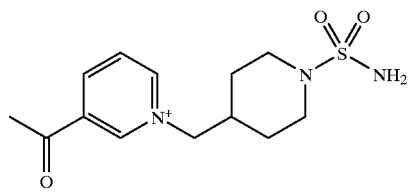 |
| 148 | 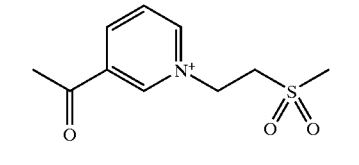 |
| 151 | 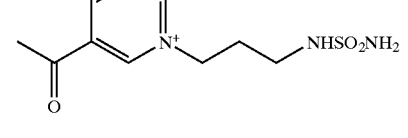 |
-continued
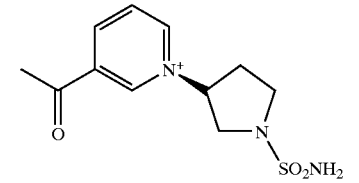
| Compound No. | R |
|---|---|
| 152 | 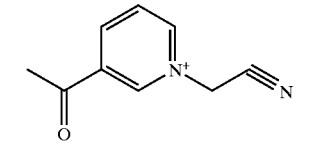 |
| 153 | 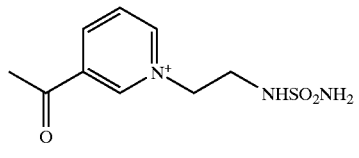 |
| 155 | 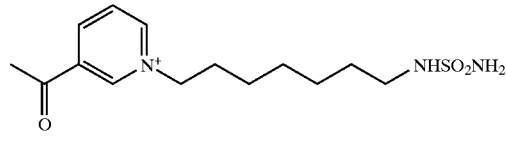 |
| 156 | 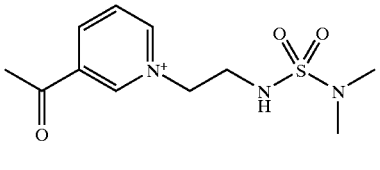 |
| 157 | 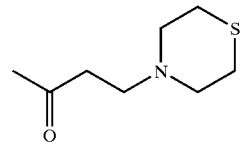 |
| 158 | 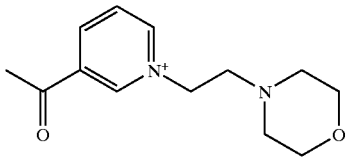 |
| 160 | |
| 162 | |

-continued
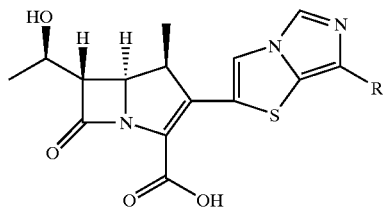
| Compound No. | R |
|---|---|
| 163 | 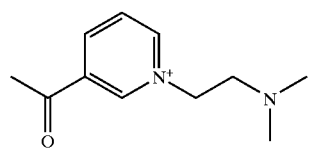 |
| 164 | 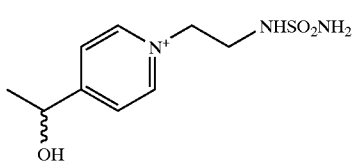 |
| 166 | 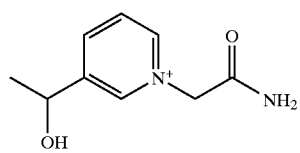 |
-continued
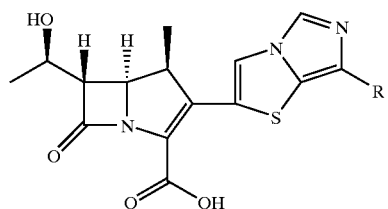
| Compound No. | R |
|---|---|
| 171 | 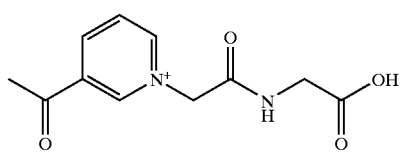 |
| 172 | 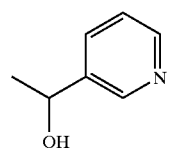 |
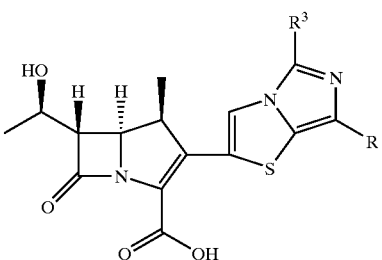
| Compound No. | R³ | R |
|---|---|---|
| 74 | CH3 | 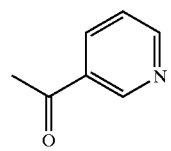 |

-continued

| Compound No. | R³ | R |
|---|---|---|
| 77 | CH3 | 3-acetylpyridinium-N-CH₂C(O)NH₂ |
| 94 | phenyl | 3-acetylpyridine |
| 100 | Cl | 3-acetylpyridine |
| 102 | Cl | 3-acetylpyridinium-N-CH₂C(O)NH₂ |
| 104 | phenyl | 3-acetylpyridinium-N-CH₂C(O)NH₂ |
| 105 | 4-(dimethylamino)phenyl | 3-acetylpyridine |
| 106 | 4-(dimethylamino)phenyl | 3-acetylpyridinium-N-CH₂C(O)NH₂ |
| 107 | morpholin-4-yl | 3-acetylpyridine |

-continued
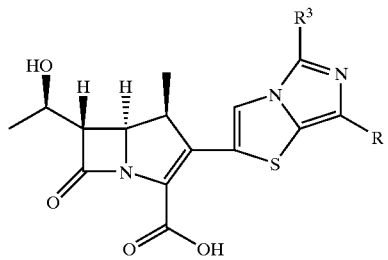
| Compound No. | R³ | R |
|---|---|---|
| 108 | 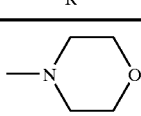 | 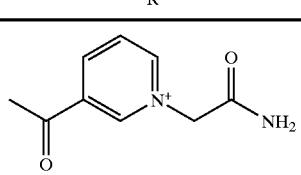 |
| 110 | SCH3 | 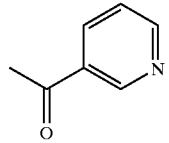 |
| 114 | SCH3 | 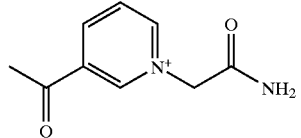 |
| 115 |  | 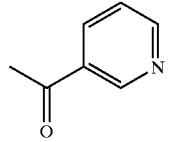 |
| 116 |  | 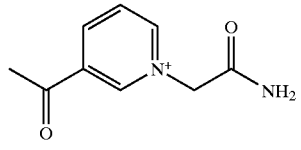 |
| 117 | CHO | 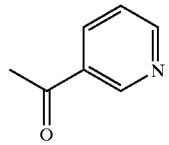 |
| 118 | SO2CH3 | 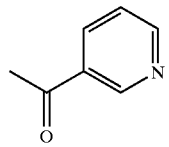 |
| 119 | CH2OH | 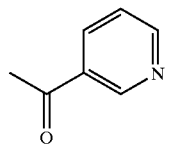 |

-continued
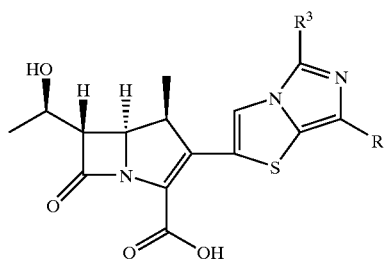
| Compound No. | R³ | R |
|---|---|---|
| 120 | CH2OH | 3-acetyl-1-(carbamoylmethyl)pyridinium |
| 121 | SCH3 | 3-acetyl-1-(carboxymethyl)pyridinium |
| 122 | SO2CH3 | 5-acetyl-1-(carbamoylmethyl)-3,4-dihydro-2H-pyridinium |
| 124 | COCH3 | 5-acetyl-3,4-dihydro-2H-pyridine |
| 125 | COCH3 | 3-acetylpyridine |
| 126 | COCH3 | 3-acetyl-1-(carbamoylmethyl)pyridinium |
| 127 | CHO | 3-acetyl-1-methylpyridinium |

-continued

| Compound No. | R³ | R |
|---|---|---|
| 128 | C2H5 | 3-acetyl-5-(methylthio)-1-(carbamoylmethyl)pyridinium |
| 129 | C2H5 | 3-acetyl-5-(methylthio)-1-(ethoxycarbonylmethyl)pyridinium |
| 130 | phenyl | 3-acetyl-5-(methylthio)-1-(carboxymethyl)pyridinium |
| 131 | cyclopropyl | 3-acetyl-1-(ethoxycarbonylmethyl)pyridinium |
| 132 | SCH3 | 3-acetyl-1-(2-(sulfamoylamino)ethyl)pyridinium |
| 133 | Cl | 3-acetyl-1-(2-(sulfamoylamino)ethyl)pyridinium |
| 134 | phenyl | 3-acetyl-1-(carboxymethyl)pyridinium |

-continued

| Compound No. | R³ | R |
|---|---|---|
| 136 | SCH3 | 3-acetyl-1-(2-(NHSO2NH2)ethyl)pyridinium |
| 137 | C2H5 | 3-acetyl-5-(SMe)-1-(carboxymethyl)pyridinium |
| 138 | C2H5 | 3-acetyl-1-(carbamoylmethyl)pyridinium |
| 139 | CHO | 3-acetyl-1-(carbamoylmethyl)pyridinium |
| 140 | Br | 3-acetyl-1-(carbamoylmethyl)pyridinium |
| 143 | CONH2 | 3-acetyl-1-(carbamoylmethyl)pyridinium |
| 145 | CH2OCH3 | 3-acetyl-1-(carbamoylmethyl)pyridinium |

-continued
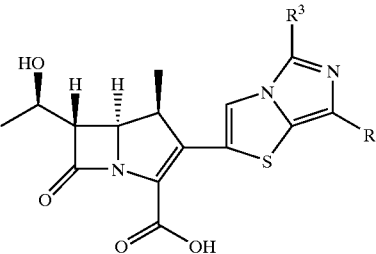
| Compound No. | R³ | R |
|---|---|---|
| 147 | Br |  |
| 154 | 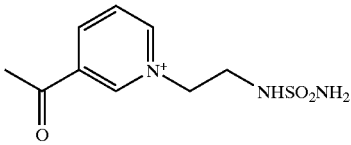 | 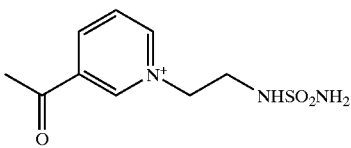 |
| 161 | Cl | 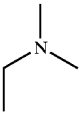 |
| 165 | 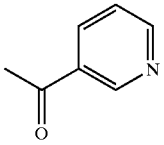 | 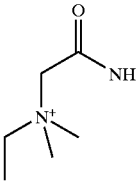 |
| 167 | 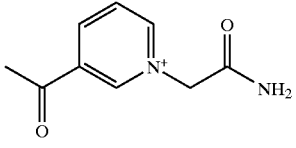 | 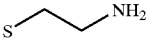 |
| 169 | 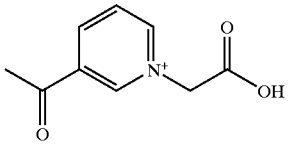 | 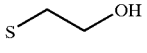 |
| 170 | 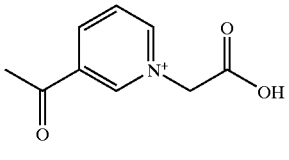 | 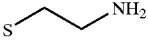 |
| 173 | 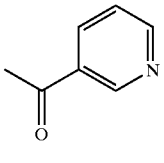 | |

-continued
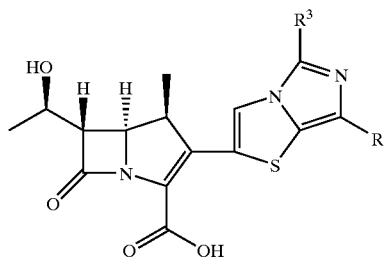
| Compound No. | R³ | R |
|---|---|---|
| 174 | S-CH₂CH₂-N₃ | 3-acetylpyridinium-CH₂-C(O)NH-CH₂-COOH |
| 175 | S-CH₂CH₂-NH₂ | 3-acetylpyridinium-CH₂-C(O)NH-CH₂-COOH |
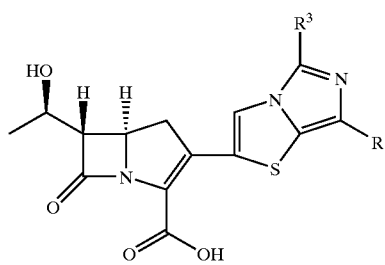
| Compound No. | R³ | R |
|---|---|---|
| 58 | H | 3-acetylpyridine |
| 59 | H | 3-acetyl-1-methylpyridinium |
| 60 | H | 3-acetyl-1-(carbamoylmethyl)pyridinium |

-continued

| Compound No. | R³ | R |
|---|---|---|
| 64 | H | 3-acetyl-1-(carboxymethyl)pyridinium |
| 73 | CH3 | 3-acetylpyridine |
| 78 | CH3 | 3-acetyl-1-(carbamoylmethyl)pyridinium |
| 144 | phenyl | 3-acetyl-1-(carboxymethyl)pyridinium |
| 149 | phenyl | 3-acetyl-1-(2-piperidinoethyl)pyridinium |
| 150 | H | 3-acetyl-1-(2-(sulfamoylamino)ethyl)pyridinium |
| 159 | H | 3-acetyl-1-(3-(sulfamoylamino)propyl)pyridinium |

-continued

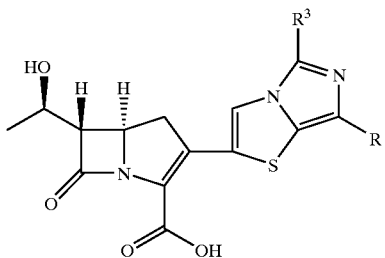

| Compound No. | R³ | R |
|---|---|---|
| 168 | (HO, H, H structure with methyl) | (pyridinium-carbonyl-CH₂-C(O)NH₂ structure) |

Preparation Example 1

Preparation for Injection

The compound of Example 1 was aseptically dispensed into vials in an amount of 1000 mg (titer) per vial to prepare injections.

Preparation Example 2

Soft Capsule for Rectal Administration

| | |
|---|---|
| Olive oil | 160 parts (titer) |
| Polyoxyethylene lauryl ether | 10 parts (titer) |
| Sodium hexamethanoate | 5 parts (titer) |

The compound of Example 1 in an amount of 250 parts (titer) was added to and homogeneously mixed with a homogeneous base consisting of the above ingredients and filled into soft capsules in an amount of 250 mg (titer) per capsule to prepare soft capsules for rectal administration.

Test Example 1

Antibiotic Activities

The minimum inhibiting concentrations (MIC, μg/ml) of representative compounds among the novel carbapenem derivatives according to the present invention to various pathogenic bacteria were measured in accordance with the method described in CHEMOTHERAPY, vol. 16, No. 1, 99, 1968. The results are shown in Table 1. The culture medium for measurement was Sensitivity Disk agar-N+5% Horse blood, and the amount of inoculants was $10^6$ CFU/ml.

TABLE 1

| Test organisms | Compound of Ex. 1 | Compound of Ex. 2 | Compound of Ex. 39 | Compound A | Compound B | Compound C |
|---|---|---|---|---|---|---|
| S. aureus 209P JC-1 | <0.008 | <0.008 | 0.008 | 0.016 | <0.006 | 0.008 |
| S. aureus M126* | 1 | 0.5 | 0.25 | 1 | 1.56 | 4 |
| S. aureus M126 HR* | 4 | 2 | 1 | 8 | 6.25 | 64 |
| S. pneumoniae PRC9** | 0.031 | 0.031 | 0.031 | 0.063 | 0.1 | 0.25 |
| B. catarrhalis W-0500 | 0.016 | 0.016 | 0.031 | 0.031 | <0.025 | 0.063 |
| H. influenzae PRC44 | 0.031 | 0.031 | 0.063 | 0.031 | 0.1 | 8 |
| E. coli NIHJ JC-2 | 1 | 0.031 | 0.031 | 0.125 | 3.13 | 0.125 |
| K. pneumoniae PCI602 | 1 | 0.063 | 0.031 | 0.25 | 3.13 | 0.25 |

*methicillin-hyperresistant strain
**penicillin-hyperresistant strain

Compound A: Sodium (1S,5R,6S)-2-(7-acetylimidazo[5,1-b]thiazol-2-yl)-6-((1R)-1-hydroxyethyl)-1-methyl-1-carbapen-2-em-3-carboxylate (compound of Example 134 in WO 98/32760)

Compound B: Sodium (1S,5R,6S)-2-(7-benzoylimidazo[5,1-b]thiazol-2-yl)-6-((1R)-1-hydroxyethyl)-1-methyl-1-carbapen-2-em-3-carboxylate (compound of Example 37 in WO 00/06581)

Compound C: Imipenem

The carbapenem derivatives which are compounds represented by formulae (I) and (II) according to the present invention have strong antibiotic activities against various pathogenic bacteria including MRSA, PRSP, Influenzavirus, and β-lactamase producing bacteria.

The carbapenem derivatives which are compounds represented by formulae (I) and (II) according to the present invention are clearly superior to compound A and compound B, which are carbapenem derivatives proposed in the prior application, particularly in antibiotic activity against methicillin-hyperresistant Staphylococcus aureus.

Test Example 2

Therapeutic Effect

The therapeutic effect of representative compounds among the novel carbapenem derivatives according to the present invention on mice subjected to general infection with MRSA were assayed by the following method, and the results are shown in Table 2. Specifically, cyclophosphamide (200 mg/kg) was administered intraperitoneally to mice (n=8), and, four days after the administration of cyclophosphamide, *Staphylococcus aureus* MF126 (MRSA) was inoculated intraperitoneally to infect the mice with MRSA. Cilastatin (1 mg/mouse) and the carbapenem compound in an indicated amount were subcutaneously administered two hours and four hours after the infection. $ED_{50}$ was calculated based on the survival rate on the seventh day after the infection.

TABLE 2

|  | $ED_{50}$, mg/mouse |
|---|---|
| Amount of inoculant: $2.5 \times 10^6$ CFU/mouse | |
| Compound of Example 37 | 0.139 |
| Amount of inoculant: $2.8 \times 10^6$ CFU/mouse | |
| Compound of Example 2 | 0.07 |
| Compound of Example 11 | 0.25 |
| Vancomycin | 0.50 |
| Amount of inoculant: $2.9 \times 10^6$ CFU/mouse | |
| Compound of Example 39 | 0.02 |
| Amount of inoculant: $5.9 \times 10^6$ CFU/mouse | |
| Compound of Example 65 | 0.32 |
| Vancomycin | 0.71 |

The carbapenem derivatives, which are compounds represented by formulae (I) and (II), according to the present invention had significantly better therapeutic effect in vivo than vancomycin as a conventional therapeutic agent for MRSA.

Test Example 3

Acute Toxicity Test

The compound of Example 1 was administered intravenously to mice (ICR, male, each group consisting of three mice) in an amount of 2,000 mg/kg. As a result, all of the mice survived.

Test Example 4

Acute Toxicity Test

The compound of Example 2 was administered intravenously to mice (ICR, male, each group consisting of three mice) in an amount of 1,000 mg/kg. As a result, all of the mice survived.

What is claimed is:

1. A compound represented by formula (I) or a pharmaceutically acceptable salt thereof:

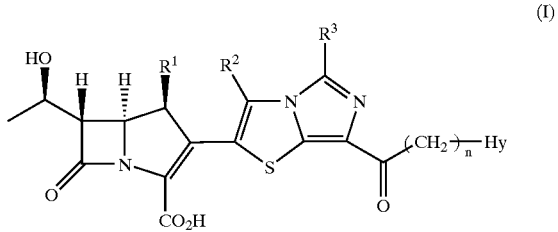

(I)

wherein $R^1$ represents a hydrogen atom or methyl, $R^2$ and $R^3$ represent a hydrogen atom, n is 0 (zero), and Hy represents pyridinium-3-yl which is substituted by carbamoyl lower alkyl, carboxyl lower alkyl, or aminosulfonylamino lower alkyl at its 1-position and is optionally substituted by amino lower alkylthio at other than the 1-position.

2. The compound according to claim 1, wherein $R^1$ represents methyl, $R^2$ and $R^3$ represent a hydrogen atom, n is 0 (zero), and Hy represents 1-carbamoylmethylpyridinium-3-yl.

3. The compound according to claim 1, wherein $R^1$, $R^2$ and $R^3$ represent a hydrogen atom, n is 0 (zero), and Hy represents 1-carbamoylmethylpyridinium-3-yl.

4. The compound according to claim 1, wherein $R^1$ represents methyl, $R^2$ and $R^3$ represent a hydrogen atom, n is 0 (zero), and Hy represents 1-carboxymethylpyridinium-3-yl.

5. The compound according to claim 1, wherein $R^1$ represents methyl, $R^2$ and $R^3$ represent a hydrogen atom, n is 0 (zero), and Hy represents 1-(2-aminosulfonylaminoethyl)pyridinium-3-yl.

6. A pharmaceutical composition comprising a therapeutically effective amount of the compound according to any one of claims 1 to 5 and a pharmaceutically acceptable carrier.

7. The pharmaceutical composition according to claim 6, which further comprises pharmaceutically acceptable adjuvants.

8. A method for treating bacterial infection, comprising the step of administering a therapeutically effective amount of the compound according to any one of claims 1 to 5 or a pharmaceutically acceptable salt thereof to a mammal in need thereof.

9. The method according to claim 8, wherein the mammal is a human.

* * * * *

UNITED STATES PATENT AND TRADEMARK OFFICE
CERTIFICATE OF CORRECTION

PATENT NO. : 6,908,913 B2  
APPLICATION NO. : 10/344729  
DATED : June 21, 2005  
INVENTOR(S) : Yuko Kano et al.

Page 1 of 1

It is certified that error appears in the above-identified patent and that said Letters Patent is hereby corrected as shown below:

on title page, Item (73):

Please correct Assignee's name from "Meiji Seik<u>i</u> Kaisha, Ltd." to --Meiji Seik<u>a</u> Kaisha, Ltd.--

Signed and Sealed this

Twenty-second Day of August, 2006

JON W. DUDAS  
*Director of the United States Patent and Trademark Office*